(12) United States Patent
Wang et al.

(10) Patent No.: US 9,751,875 B2
(45) Date of Patent: Sep. 5, 2017

(54) QUININE COMPOUNDS, AND OPTICAL ISOMERS, PREPARATION METHOD AND MEDICAL USE THEREOF

(71) Applicant: BEIJING FSWELCOME TECHNOLOGY DEVELOPMENT CO., LTD., Beijing (CN)

(72) Inventors: Chunjing Wang, Beijing (CN); Junyi Wang, Beijing (CN); Zejun Gao, Beijing (CN)

(73) Assignee: Beijing Fswelcome Technology Development Co., Ltd., Beijing (CN)

( * ) Notice: Subject to any disclaimer, the term of this patent is extended or adjusted under 35 U.S.C. 154(b) by 0 days.

(21) Appl. No.: 14/904,766

(22) PCT Filed: Jul. 11, 2014

(86) PCT No.: PCT/CN2014/000669
§ 371 (c)(1),
(2) Date: Apr. 25, 2016

(87) PCT Pub. No.: WO2015/007073
PCT Pub. Date: Jan. 22, 2015

(65) Prior Publication Data
US 2016/0244439 A1    Aug. 25, 2016

(30) Foreign Application Priority Data
Jul. 13, 2013 (CN) .......................... 2013 1 0297901

(51) Int. Cl.
*A61K 31/46* (2006.01)
*C07D 453/02* (2006.01)
*A61K 9/00* (2006.01)
*A61K 9/20* (2006.01)
*A61K 9/48* (2006.01)
*A61K 31/137* (2006.01)
*A61K 31/439* (2006.01)

(52) U.S. Cl.
CPC ............ *C07D 453/02* (2013.01); *A61K 9/007* (2013.01); *A61K 9/008* (2013.01); *A61K 9/0043* (2013.01); *A61K 9/20* (2013.01); *A61K 9/4808* (2013.01); *A61K 31/137* (2013.01); *A61K 31/439* (2013.01)

(58) Field of Classification Search
USPC .................... 514/253.04, 248, 305
See application file for complete search history.

(56) References Cited

FOREIGN PATENT DOCUMENTS

| CN | 1951938 A | 4/2007 |
|---|---|---|
| CN | 1976701 A | 6/2007 |
| WO | 2005104745 A2 | 11/2005 |

OTHER PUBLICATIONS

Berge; Journal of Pharmaceutical Sciences; Jan. 1977, vol. 66, No. 1.*
Peijin, Wu et al., "Synthesis Of Anticholinergies Of 2-(1-Naphthyl)-2-Cyclopentyl-2-Hydroxy Ethoxy Cyclic Amine compounds," Chinese J. of Medicinal Chemistry, v. 9, n. 2, Jun. 1999, pp. 102-105.
Jiang, Jun-Xia et al., "Characterization of bencycloquidium bromide, a novel muscarinic M3 receptor antagonist in guinea pig airways," Europan J. of Pharmacology 655, (2011), pp. 74-82.
Chinese Office Action dated Aug. 2, 2016 for Chinese Application No. 201480020342.8, 10 pgs.
Laine, D.I. et al., "Discovery of Novel 1-Azoniabicyclo[2.2.2\octane Muscarinic Acetylcholine Receptor Antagonists," J. Med. Chem. 2009, 52, pp. 2493-2505.

* cited by examiner

*Primary Examiner* — Pancham Bakshi
(74) *Attorney, Agent, or Firm* — Brooks Kushman P.C.

(57) ABSTRACT

The present invention discloses a class of quinine compounds and pharmaceutically acceptable salts, solvates, prodrugs or optical isomers thereof. Also disclosed in the present invention are that the above compounds have a selective antagonistic effect on the receptor subtypes of $M_1$ and $M_3$, but have no significant effect on $M_2$ receptor subtype, and the above compounds are characterized by rapid action, long-lasting efficacy, and low toxic and side-effects when used to treat rhinitis, post-cold rhinitis, chronic trachitis, airway hyperresponsiveness, asthma, chronic obstructive pulmonary diseases, cough, urinary incontinence, frequent urination, unstable bladder syndrome, bladder spasms, bladder inflammation and gastrointestinal diseases such as irritable bowel syndrome, spastic colitis, as well as duodenal and gastric ulcers.

24 Claims, No Drawings

QUININE COMPOUNDS, AND OPTICAL ISOMERS, PREPARATION METHOD AND MEDICAL USE THEREOF

CROSS-REFERENCE TO RELATED APPLICATION

This application is the U.S. national phase of PCT Appln. No. PCT/CN2014/000669 filed Jul. 11, 2014, which claims priority to Chinese application 201310297901.7 filed Jul. 13, 2013, the disclosures of which are incorporated in their entirety by reference herein.

TECHNICAL FIELD

The present invention relates to quinine compounds, optical isomers and manufacture methods thereof and compositions comprising these compounds for medicinal purposes, and in particular, to novel M receptor antagonists having a selective effect on subtypes of M receptor, which have a strong effect on receptor subtypes of $M_3$ and $M_1$, but have no significant effect on $M_2$ receptor subtype.

BACKGROUND OF THE RELATED ART

It is found in some patent documents that a compound comprising a quinine structure is used for anti-cholinergic effect. For example, a compound disclosed in Chinese invention patent CN200810112248.1 and Chinese invention patent CN200910223255.3 has a structure as below, wherein: R is methyl, ethyl, propyl, isopropyl, or cyclopropyl; and X represents halogen atom.

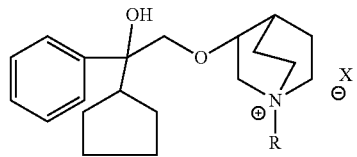

French patent FR2012964 disclosed a structure as below, wherein: R is H atom, hydroxyl or alkyl with 1-4 carbon atoms; $R_1$ is phenyl or thienyl; and $R_2$ is cyclohexyl, cyclopentyl or thienyl.

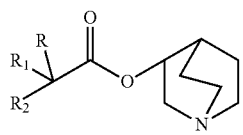

U.S. Pat. No. 5,654,314 disclosed a structure as below:

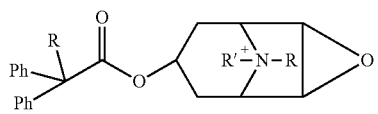

WO Patent WO01/04118 disclosed a structure as below:

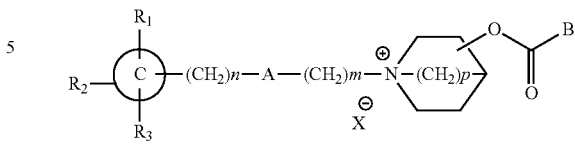

The above compounds have significant disadvantages, such as short-lasting efficacy, slow action, or significant toxic and side effects, or the like, in the treatment of rhinitis, post-cold rhinitis, chronic trachitis, airway hyperresponsiveness, asthma, chronic obstructive pulmonary diseases, cough, urinary incontinence, frequent urination, unstable bladder syndrome, bladder spasms, bladder inflammation and gastrointestinal diseases such as irritable bowel syndrome, spastic colitis, as well as duodenal and gastric ulcers.

The compounds of the present invention overcome the disadvantages of the above compounds, and in particular, are characterized by longer efficacy, rapid action, and lower toxic and side effects in the treatment of chronic trachitis, airway hyperresponsiveness, asthma, and chronic obstructive pulmonary diseases as compared with the compounds of prior art. Due to their good stability, the compounds of the present invention are suitable for manufacturing an inhalant that is administered once a day for treating chronic obstructive pulmonary diseases, and in particular, suitable for manufacturing a solution-type metered dose inhalation aerosol that is administered once a day. The present invention relates to the synthesis of said compound, the manufacture of a pharmaceutical composition comprising said compound and pharmaceutical uses thereof.

The compound of the present invention can also be used for treating the above respiratory diseases such as rhinitis, post-cold rhinitis, chronic trachitis, airway hyperresponsiveness, asthma, chronic obstructive pulmonary diseases, and the like, in combination with $\beta_2$ receptor agonists, steroid hormone, antiallergic drugs, anti-inflammatory drugs, anti-infective drugs, phospholipase iv antagonists and the like.

CONTENT OF THE INVENTION

A novel M receptor subtype selective antagonist compound of the present invention can be represented by the structure of formula (I):

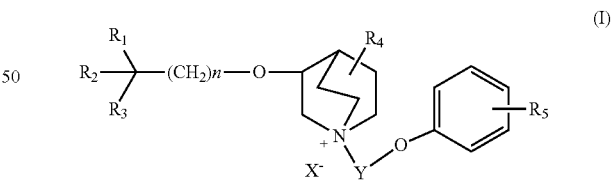

wherein in formula (I):

n is selected from 1~7, preferably 1~3, most preferably 1.

$R_1$ is a $C_3$-$C_7$ hydrocarbyl, which can be unsubstituted, or can further, without limitation, be optionally substituted by halogen, alkoxy, alkoxyhydrocarbyl, heterocyclyl, or aryl; preferably an unsubstituted cycloalkyl, and most preferably a cyclopentyl or cyclohexyl.

$R_2$ is an aryl, i.e., phenyl, heteroaryl containing one or more heteroatoms (the heteroatom may be N, O, or S), naphthyl, or biphenyl, which can be unsubstituted, or further be optionally substituted, wherein the substituent(s) can be one or more of halogen, hydroxyl, phenyl, —$OR_6$, —$SR_6$, —NR₆R₇, —NHCOR₆, —CONR₆R₇, —CN, —NO₂, —COOR₆, —CF₃ or linear or branched $C_1$-$C_4$ hydrocarbyl; unsubstituted phenyl, pyridyl, furyl and thieny are preferred; $R_6$ and $R_7$ can be a hydrogen atom, a linear or branched $C_1$-$C_4$ hydrocarbyl, or can form a cyclohydrocarbyl together.

$R_3$ is a hydroxyl, halogen, alkoxy or acyloxy, wherein the alkoxy or acyloxy can be unsubstituted, or can further, without limitation, be optionally substituted by halogen, hydroxyl, alkoxy, hydrocarbyl, alkoxyhydrocarbyl, cyclohydrocarbyl, heterocyclyl, or aryl; preferably a hydroxyl or methoxyl, and most preferably a hydroxyl.

$R_4$ and $R_5$ may be present or absent, and respectively may, without limitation, be a substituent such as halogen, hydroxyl, hydrocarbyloxy, hydrocarbyl, hydrocarbyloxyhydrocarbyl, heterocyclyl, aryl and the like, when present.

Y is a linear or branched $C_1$-$C_7$ alkyl or —(CH₂—O—CH₂)$_m$— (wherein m is equal to 1-3), which can be optionally substituted, preferably, be substituted by halogen, hydroxyl, alkoxy, alkoxyalkyl, unsaturated hydrocarbyl, cylcohydrocarbyl, or heterocyclyl; preferably a methyl, ethyl, propyl or —(CH₂—O—CH₂)—; and most preferably an ethyl or propyl.

$X^-$ is an acid radical or a hydroxide, preferably a pharmaceutically acceptable acid radical, examples of which include a salt derived from an inorganic acid, such as hydrochloride, bromide, iodide, nitrate, carbonate, bicarbonate, phosphate, hydrophosphate, dihydric phosphate, sulfate, disulfate, sulfite, hydrosulphite, or phosphite; and a salt derived from a relatively nontoxic organic acid, such as, but not limited to, acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

The compound represented by formula (I) may comprise one or more chiral centers, in which a single optical isomer or a mixture of various optical isomers falls within the scope claimed by the present invention.

The following compounds can specifically illustrate the content of the present invention but not limit the scope of the present invention.

1. (2S,3R)-3-[(2-cyclopentyl-2-hydroxyl-2-phenyl)ethoxyl]-1-(3-phenoxypropyl)-1-azabicyclo[2,2,2]octane bromide
2. (2S,3S)-3-[(2-cyclopentyl-2-hydroxyl-2-phenyl)ethoxyl]-1-(3-phenoxypropyl)-1-azabicyclo[2,2,2]octane bromide
3. (2R,3R)-3-[(2-cyclopentyl-2-hydroxyl-2-phenyl)ethoxyl]-1-(3-phenoxypropyl)-1-azabicyclo[2,2,2]octane bromide
4. (2R,3S)-3-[(2-cyclopentyl-2-hydroxyl-2-phenyl)ethoxyl]-1-(3-phenoxypropyl)-1-azabicyclo[2,2,2]octane bromide
5. (2S,3R),(2R,3S)-3-[(2-cyclopentyl-2-hydroxyl-2-phenyl)ethoxyl]-1-(3-phenoxypropyl)-1-azabicyclo[2,2,2]octane bromide
6. (2R,3R),(2S,3S)-3-[(2-cyclopentyl-2-hydroxyl-2-phenyl)ethoxyl]-1-(3-phenoxypropyl)-1-azabicyclo[2,2,2]octane bromide
7. (2S,3R)-3-[(2-cyclohexyl-2-hydroxyl-2-phenyl)ethoxyl]-1-(3-phenoxypropyl)-1-azabicyclo[2,2,2]octane bromide
8. (2S,3S)-3-[(2-cyclohexyl-2-hydroxyl-2-phenyl)ethoxyl]-1-(3-phenoxypropyl)-1-azabicyclo[2,2,2]octane bromide
9. (2R,3R)-3-[(2-cyclohexyl-2-hydroxyl-2-phenyl)ethoxyl]-1-(3-phenoxypropyl)-1-azabicyclo[2,2,2]octane bromide
10. (2R,3S)-3-[(2-cyclohexyl-2-hydroxyl-2-phenyl)ethoxyl]-1-(3-phenoxypropyl)-1-azabicyclo[2,2,2]octane bromide
11. (2R,3S),(2S,3R)-3-[(2-cyclohexyl-2-hydroxyl-2-phenyl)ethoxyl]-1-(3-phenoxypropyl)-1-azabicyclo[2,2,2]octane bromide
12. (2R,3R),(2S,3S)-3-[(2-cyclohexyl-2-hydroxyl-2-phenyl)ethoxyl]-1-(3-phenoxypropyl)-1-azabicyclo[2,2,2]octane bromide
13. (2S,3R)-3-[(2-cyclobutyl-2-hydroxyl-2-phenyl)ethoxyl]-1-(3-phenoxypropyl)-1-azabicyclo[2,2,2]octane bromide
14. (2S,3S)-3-[(2-cyclobutyl-2-hydroxyl-2-phenyl)ethoxyl]-1-(3-phenoxypropyl)-1-azabicyclo[2,2,2]octane bromide
15. (2R,3S)-3-[(2-cyclobutyl-2-hydroxyl-2-phenyl)ethoxyl]-1-(3-phenoxypropyl)-1-azabicyclo[2,2,2]octane bromide
16. (2R,3R)-3-[(2-cyclobutyl-2-hydroxyl-2-phenyl)ethoxyl]-1-(3-phenoxypropyl)-1-azabicyclo[2,2,2]octane bromide
17. (2R,3S),(2S,3R)-3-[(2-cyclobutyl-2-hydroxyl-2-phenyl)ethoxyl]-1-(3-phenoxypropyl)-1-azabicyclo[2,2,2]octane bromide
18. (2R,3R),(2S,3S)-3-[(2-cyclobutyl-2-hydroxyl-2-phenyl)ethoxyl]-1-(3-phenoxypropyl)-1-azabicyclo[2,2,2]octane bromide
19. (2S,3R)-3-[(2-cyclopropyl-2-hydroxyl-2-phenyl)ethoxyl]-1-(3-phenoxypropyl)-1-azabicyclo[2,2,2]octane bromide
20. (2R,3S)-3-[(2-cyclopropyl-2-hydroxyl-2-phenyl)ethoxyl]-1-(3-phenoxypropyl)-1-azabicyclo[2,2,2]octane bromide
21. (2S,3S)-3-[(2-cyclopropyl-2-hydroxyl-2-phenyl)ethoxyl]-1-(3-phenoxypropyl)-1-azabicyclo[2,2,2]octane bromide
22. (2R,3R)-3-[(2-cyclopropyl-2-hydroxyl-2-phenyl)ethoxyl]-1-(3-phenoxypropyl)-1-azabicyclo[2,2,2]octane bromide
23. (2R,3S),(2S,3R)-3-[(2-cyclopropyl-2-hydroxyl-2-phenyl)ethoxyl]-1-(3-phenoxypropyl)-1-azabicyclo[2,2,2]octane bromide
24. (2R,3R),(2S,3S)-3-[(2-cyclopropyl-2-hydroxyl-2-phenyl)ethoxyl]-1-(3-phenoxypropyl)-1-azabicyclo[2,2,2]octane bromide
25. (2S,3R)-3-[(2-cyclopentyl-2-hydroxyl-2-phenyl)ethoxyl]-1-(2-phenoxyethyl)-1-azabicyclo[2,2,2]octane bromide
26. (2R,3R)-3-[(2-cyclopentyl-2-hydroxyl-2-phenyl)ethoxyl]-1-(2-phenoxyethyl)-1-azabicyclo[2,2,2]octane bromide
27. (2R,3R)-3-[(2-cyclopentyl-2-hydroxyl-2-phenyl)ethoxyl]-1-phenoxymethyl-1-azabicyclo[2,2,2]octane bromide
28. (2R,3R)-3-[(2-cyclopentyl-2-hydroxyl-2-phenyl)ethoxyl]-1-phenoxymethoxymethyl-1-azabicyclo[2,2,2]octane chloride
29. (2R,3R)-3-[(2-cyclopentyl-2-hydroxyl-2-naphthyl)ethoxyl]-1-(3-phenoxypropyl)-1-azabicyclo[2,2,2]octane bromide
30. (2R,3R)-3-[(2-cyclopentyl-2-hydroxyl-2-(o-chlorophenyl))ethoxyl]-1-(3-phenoxypropyl)-1-azabicyclo[2,2,2]octane bromide
31. (2R,3R)-3-[(2-cyclopentyl-2-hydroxyl-2-(3-pyridyl))ethoxyl]-1-(3-phenoxypropyl)-1-azabicyclo[2,2,2]octane bromide 32. (2R,3R)-3-[(2-cyclopentyl-2-hydroxyl-2-(2-furyl))ethoxyl]-1-(3-phenoxypropyl)-1-azabicyclo[2,2,2]octane bromide
33. (2R,3R)-3-[(2-cyclopentyl-2-methoxyl-2-(3-pyridyl))ethoxyl]-1-(3-phenoxypropyl)-1-azabicyclo[2,2,2]octane bromide The present invention provides a process scheme for synthesizing the compound of structural formula (I) as follows:

Step 1: 1-$R_1$-1-$R_2$ oxirane was prepared according to the methods described in literatures[1-2] (1. Guangling Wen, Peijin Wu, Improvement on the synthesis method of 3-(2-phenyl-2-cyclopentylethoxy) quinuclidine hydrochloride, Bullet of the Academy of Military Medical Sciences, 1988: 470 turn to 402; 2. Peijin Wu, Liuhong Yun, Synthesis of anticholinergic drug of 2-(1-naphthyl)-2-cyclopentyl-2-hydroxylethoxy cyclohydrocarbyl amine compounds, Chinese Journal of Medicinal Chemistry 1999.6, 9(2), p 102-105.), and aryl hydrocarbyl ketone (some kinds of aryl hydrocarbyl ketone were generated by reacting aryl cyanide with a Grignard reagent prepared by reacting hydrocarbyl bromide with magnesium in THF, see formula (1) below) was reacted with dimethyl sulfate, dimethyl sulfide and sodium hydride to generate 1-aryl-1-hydrocarbyloxirane, i.e., intermediate 1 (see formula (2) below).

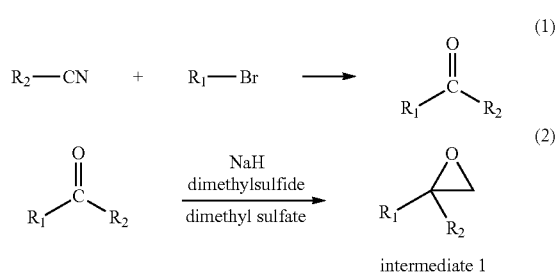

intermediate 1

Step 2: Preparation of 3-[(2-$R_1$-2-$R_2$-2-hydroxyl)ethoxyl]-1-azabicyclo[2,2,2]octane free alkali Intermediate 2 could be obtained by reacting intermediate 1 with quinuclidinol (or quinuclidinol substituted by $R_4$) under the condition of NaH.

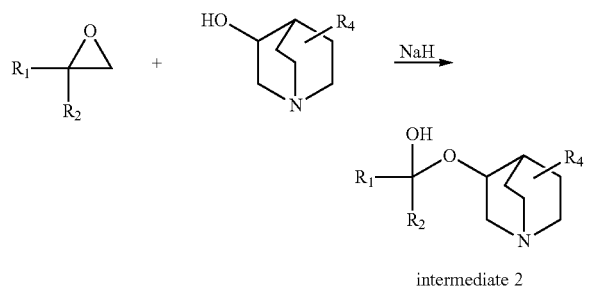

intermediate 2

To commercially available 3-quinuclidinol derivatives was added DMSO, followed by the addition of sodium hydride, and the mixture was reacted at 20-60° C., and then cooled to room temperature, and a solution of 1-$R_1$-1-$R_2$-oxirane (self-prepared) in DMSO was added thereto, and after the completion of dropping, the resulting mixture was heated at 20-70° C. in oil bath to react for 0.5-12 hours. Under the condition of ice bath, ice water was added at an inner temperature of 30° C. or less. The reaction mixture was extracted with isopropyl ether, and the ether layer was combined and washed with a saturated NaCl aqueous solution. The organic layer was dried over anhydrous sodium sulfate overnight, the drying agent was removed by filtration, and the solvent was removed by rotary evaporation, to obtain intermediate 2 as a red oily matter.

Step 3: Purification of 3-[(2-$R_1$-2-$R_2$-2-hydroxyl)ethoxyl]-1-azabicyclo[2,2,2]octane free alkali by Column Chromatography and Related Purification Ttreatment A sample of the above intermediate 2 was separated on a silica gel column, using ammoniated dichloromethane or trichloromethane and methanol as mobile phase and a TLC plate to monitor the purity of the sample. The intermediate 2 would be a mixture containing different optical structures depending on the structure of optical isomers of quinuclidinol, and under the above elution system, if quinuclidinol was in S configuration, the intermediate 2 would comprise two kinds of configurations of (2R,3S) and (2S,3S), and could be purified into two kinds of free alkalis, (2R,3S) and (2S,3S), depending on the elution sequence; if quinuclidinol was in R configuration, the intermediate 2 would comprise two kinds of configurations of (2R,3R) and (2S,3R), and could be purified into two kinds of free alkalis, (2S,3R) and (2R,3R), depending on the elution sequence; if quinuclidinol was racemate, the intermediate 2 would comprise four kinds of configurations of (2R,3S), (2S,3S), (2R,3R), (2S,3R), and could be purified into two kinds of free alkalis, (2R,3S), (2S,3R) and (2S,3S), (2R,3R), depending on the elution sequence. The separated free alkali was referred to as intermediate 3.

Step 4: Preparation of 3-Z—Y-oxylbenzene (Intermediate 4)

intermediate 4

Phenol was added into a three-necked flask, followed by the addition of sodium hydroxide and a solution of Z—Y—Z (where Z was halogen atom) in absolute ethanol, and then the resulting mixture was reacted under heating and refluxing in oil bath, with a white solid being precipitated, until the essentially complete reaction of phenol monitored by TLC (TLC condition: petroleum ether/ethyl acetate=5.0 ml/1.0 ml). After the reaction being completed, the solid was removed by filtration, and the solvent was removed from the filtrate at 50° C. or less under reduced pressure by a water pump, thereby obtaining an oily matter containing a white solid, to which was added petroleum ether and then left it overnight. The precipitated solid was removed by filtration, and the solvent was removed from the filtrate at 25-40° C. under reduced pressure by a water pump, thereby obtaining a yellow oily matter. The oily matter was distilled under reduced pressure, to collect a colorless, transparent oily matter, i.e., intermediate 4.

Step 5: Preparation of the Compound of Formula (I)

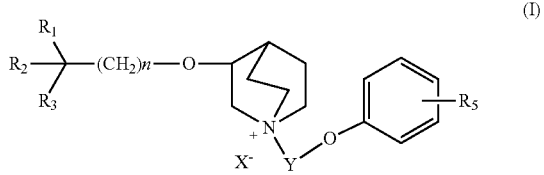

Intermediate 2 or intermediate 3 was added into an eggplant-shaped flask followed by the addition of chloroform, to obtain a yellow transparent solution, to which intermediate 4 and acetonitrile were added, and the resulting mixture was then stirred at room temperature to react for 10-90 h under the protection of nitrogen, with the completion of reaction being monitored by TLC (TLC condition: chloroform/methanol/ammonia water=5.0 ml/1.5 ml/2d). After the reaction being completed, the solvent was removed from the reaction solution by rotary evaporation at 25-40° C. under reduced pressure by a water pump, thereby obtaining a yellow oily matter, to which was added ethyl ether to precipitate a great quantity of solid, and the solid was collected by suction filtration to obtain an off-white solid, i.e., the title compound of formula (I).

The above compound of formula (I) was reacted with $Ag_2O$ to replace halogen with hydroxide, which could be then converted into other acid radical by reacting with other acid. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

Any pharmaceutical composition comprising one or more compounds of formula (I) described above falls within the scope claimed by the present invention, and the route of administration can be, for example, oral, topical, intravenous, intramuscular, endarterial, intraperitoneal, rectal, vaginal, endonasal, or inhalational administration. The formulation of the present invention can be designed to be rapid-acting, rapid-released or long-acting. In addition, the compound can be administered by a topical route rather than a systemic route and according to representative embodiments, the composition of the present invention can be formulated to drugs administered for mammals, preferably human.

The composition comprising one or more compounds of the present invention and suitable excipients can be administered repeatedly, or the composition can be administered continuously. The suitable sites of administration include, but not limited to, nasal cavity, lung, blood vessel, muscle, bronchus, and intestines and stomach. The formulation can be in the form of liquid dosage form, freeze-dried powder, solid or semi-solid, such as solution, suspension, emulsion, tablet, pill, capsule, pulvis, suppository, retentive enemas, aerosol, powder aerosol, or the like, preferably a unit dosage form suitable for simply administrating accurate dosage. The examples of suitable excipients include, but not limited to, water, saline, lactose, glucose, saccharose, sorbitol, mannitol, starch, arabic gum, calcium phosphate, alginate, tragacanth, gelatin, calcium silicate, microcrystalline cellulose, polyvinylpyrrolidone, cellulose, syrup, methylcellulose, ethylcellulose, hydroxypropyl methylcellulose and polyacrylic acid. The composition can further comprise lubricant such as talc, magnesium stearate and mineral oil; wetting agent; emulgator; suspending agent; preservative such as methyl-, ethyl- and propyl-hydroxyl-benzoate; pH regulator such as inorganic and organic acids and bases; sweetening agent; and corrigent.

For parenteral administration, the composition can be in the form of sterile injection and aseptically packaged powder. Preferably, the injection is formulated at pH 4.5-7.5.

The pharmaceutical composition of the present invention can further be any orally acceptable dosage forms, including tablet, capsule, cachet, emulsion, suspension, solution, syrup, elixir, nebula, pill, troche, pulvis, granule and sustained-release preparation. Suitable excipients for oral administration include pharmaceutical-grade mannitol, lactose, starch, magnesium stearate, saccharin sodium, talc, cellulose, glucose, gelatin, saccharose, magnesium carbonate, and the like. In the case of tablets for oral administration, the commonly used carriers include lactose and microcrystalline cellulose, and lubricant such as magnesium stearate is generally added; for capsules, useful diluents include lactose and dry corn starch; when the suspension is required for oral administration, active ingredients are mixed with emulgator and suspending agent, and some sweetening agents, corrigents or colorants can also be added as appropriate.

For example, powder, solution or suspension for pulmonary inhalation, nasal spray, oral, topical or intravenous administration may be formed by dissolving or dispersing one or more compounds of the present invention and optionally one or more pharmaceutically acceptable auxiliary material in a vehicle such as saline solution, glucose aqueous solution, glycerol, ethanol or the like. Liquid composition is prepared, and the pharmaceutical formulation in the form of liquid suspension or solution may be prepared by using sterile liquid such as oil, water, ethanol and a combination thereof; for pulmonary inhalation, nasal spray, oral or intravenous administration, a pharmaceutically suitable surfactant, suspending agent or emulgator may be added; a suspension may comprise oil, such as peanut oil, sesame oil, cottonseed oil, corn oil and olive oil; a suspension formulation may also comprise esters of fatty acid, such as ethyl oleate, isopropyl myristate, fatty glyceride and acetylated fatty glyceride. A suspension formulation may comprise alcohol, such as ethanol, isopropanol, hexadecanol, glycerol and propanediol; ether, such as polyethylene glycol; petroleum hydrocarbon, such as mineral oil and vaseline. Water may also be used in a suspension formulation.

The composition may be in the form of pill, tablet or capsule, and therefore, the composition may comprise one or more diluents, such as lactose, saccharose, dicalcium phosphate and the like; a disintegrant, such as starch or derivatives thereof; a lubricant, such as magnesium stearate and the like; and/or a binder, such as starch, arabic gum, polyvinylpyrrolidone, gelatin, cellulose and derivatives thereof. The pill, tablet or capsule may be prepared by any method known to those skilled in the art.

Alternatively, the pharmaceutical composition of the present invention may be in the form of suppository for rectal administration. These suppositories may be prepared by mixing a medication with a suitable non-irritating excipient which is a solid at room temperature but a liquid at the rectal temperature and thus releases the medication in the rectum.

Such materials include cocoa butter, beewax, polyethylene glycol, glyceryl stearate and/or hydrogenated cocoglycerides. The composition suitable for rectal administration may also comprise a rectal enema unit, which comprises one or more compounds of the present invention and a pharmaceutically acceptable vehicle (e.g., 50% ethanol aqueous solution or saline solution), and such vehicle is physiologically compatible with rectum and/or colon. A rectal enema unit comprises an applicator tip protected by an inert cover, which is preferably composed of polyethylene, lubricated with a lubricant such as white vaseline, and preferably protected by a check valve to prevent the medication released from back flow. The rectal enema unit further has a sufficient length, preferably 2 inches, so that it is inserted into colon through anus.

The pharmaceutical composition of the present invention may also be in the form of topical administration, especially when therapeutic targets include regions or organs into which the pharmaceutical composition can be easily administered by topical administration, and diseases of these organs include diseases of lung, nasal mucosa, and trachea. Topical formulations suitable for these regions or organs are prepared easily. For topical administration, the composition comprising one or more compounds of the present invention may be in the form of nasal spray, solution inhalation, metered-dose powder inhalation, metered-dose solution inhalation, metered-dose suspension inhalation and the like.

For administration by inhalation, the composition in the form of dry powder or liquid can be delivered by a sprayer. Such compositions are prepared according to the technologies known in the field of pharmaceutical formulation, and the composition in the form of liquid can be prepared in saline with phenylcarbinol or other suitable preservatives, sorbefacient enhancing bioavailability, fluorocarbon and/or other conventional solubilizer or dispersant.

In the solution-type metered-dose inhalation aerosol comprising one or more compounds of formula (I), the latent solvent includes one or more of absolute ethanol, glycerol, and diols, or a mixture thereof, wherein the diols include, but not limited to, ethylene glycol, propanediol, polyethylene glycol 200, polyethylene glycol 300, polyethylene glycol 400, polyethylene glycol 600, polyethylene glycol 800 and the like. The propellant in the above aerosol includes one of tetrafluoroethane (HFA-134a) and heptefluoro propane (HFA-227ea), or a mixture thereof. The surfactant in the above aerosol includes one or more of oleic acid; lactic acid oligomer (OLA); sorbitans, such as span 20, span 65, span 80, span 85; polyoxyethylene sorbitans, such as Tween 20, Tween 80; polyoxyethylene fatty alcohols, such as Bri j30, Bri j35, Cremophor; polyoxyethylene polyoxypropylene copolymer, such as Pluronic F-68; polyethylene glycol stearates, such as Solutol HS15; phospholipids, such as granulesten, lecithin. Oleic acid, lecithin or a mixture thereof is preferred. In the aerosol, the content of said compound of formula I is 0.005~1% by weight, preferably 0.02~0.5%. The content of the latent solvent in the inhalation aerosol is 5~40% by weight, preferably 17.5-29.975%. The content of the surfactant in the inhalation aerosol is 0~5% by weight, preferably 0.005~2%. The content of the propellant in the inhalation aerosol is 54~90% by weight, preferably 70~80%.

In the metered-dose powder inhalation comprising one or more compounds of formula (I), said inert carrier comprises a diluent and a lubricant, wherein said diluent is one or more of glucan, arabinose, lactose, mannitol, xylitol, saccharose, fructose, sorbitol, maltose, amino acid and glucose, or a mixture thereof, and said lubricant is magnesium stearate or sodium benzoate.

In the metered-dose naristillae or nasal spray comprising one or more compounds of formula (I), said inert carrier is one or more selected from benzalkonium chloride, benzalkonium bromide, phenylcarbinol, benzoic acid, trichloro-t-butanol, p-hydroxyl benzoates, sorbic acid, phenol, thymol and volatile oil, or a mixture thereof.

Moreover, the present invention provides uses of said pharmaceutical composition which can be used for the manufacture of medications for preventing and treating various acute or chronic obstructive airways diseases, such as chronic obstructive lung diseases, bronchial asthma; as well as acute or chronic rhinitis and post-cold rhinitis in mammal and human.

The compound of formula (I) and other active ingredients (e.g., beclomethasone dipropionate, chlortrimeton, naphazoline or fenoterol) are formulated into a combination, which can be used for the treatment of various acute or chronic obstructive airways diseases, such as chronic obstructive lung diseases, bronchial asthma, and various rhinitises.

In order to obtain therapeutic effects rapidly and effectively, and ensure no toxic and side effects in use, it is suggested that the daily dosage of the compound of the present invention used should be 10-1000 μg, and optimally 40-500 μg.

In addition to those representative dosage forms, those skilled in the art generally also know that other pharmaceutically acceptable excipients, carriers and dosage forms are included in the present invention. It should be understood that the specific dosage and therapeutic regimen for any specific patient depend on various factors which include activity of the specific compound used, the age, body weight, general health, gender, dietetic condition of the patient, administration time, and excretion rate, combination drugs, diagnosis of therapists and the severity of the specific disease to be treated. The amount of active ingredients may further depend on the specific compound and other therapeutic drugs (if present) in the composition.

DETAILED DESCRIPTION OF EMBODIMENTS

The content of the invention is described in detail by the examples of the compounds and pure optical isomers thereof below. It should be illustrated that the present invention is not limited to the examples below. The component ratio in the examples is expressed by weight, unless otherwise specifically stated.

PREPARATION OF EXAMPLE COMPOUNDS

Example 1

(2S,3R)-3-[(2-cyclopentyl-2-hydroxyl-2-phenyl) ethoxyl]-1-(3-phenoxy propyl)-1-azabicyclo[2,2,2] octane bromide Step 1: Preparation of 1-phenyl-1-cyclopentyloxirane

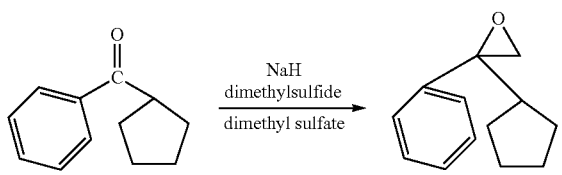 [SMILES: O=C(c1ccccc1)C1CCCC1 ; c1ccc(C2(C3CCCC3)CO2)cc1]

1-phenyl-1-cyclopentyloxirane was obtained by the reaction of commercially available cyclopentyl phenyl ketone as a starting material according to literature[1].

Step 2: Preparation of 3-[(2-cyclopentyl-2-hydroxyl-2-phenyl)ethoxyl]-1-azabicyclo[2,2,2]octane free alkali from S-3-quinuclidinol

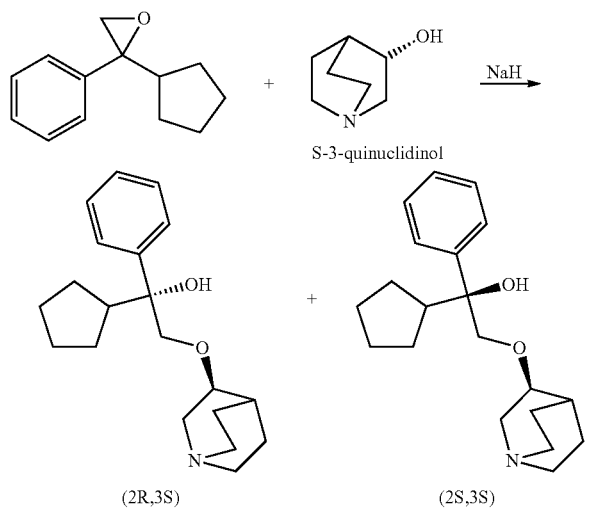

To 18.72 g (147 mmol) of commercially available S-3-quinuclidinol was added 190 ml DMSO, followed by the addition of 47.56 g (190 mmol) of sodium hydride, and the mixture was reacted at 20-60° C. for 0.5-12 h, and then cooled to room temperature, and a solution of 35.72 g (190 mmol) of 1-phenyl-1-cyclopentyloxirane (self-prepared) in 45 ml DMSO was added thereto, and after the completion of dropping, the resulting mixture was heated at 20-70° C. in oil bath to react for 0.5-12 hours. Under the condition of ice bath, 120 ml of ice water was added at an inner temperature of 30° C. or less. The reaction mixture was extracted with isopropyl ether, 100 ml×3; and the ether layer was combined and washed with a saturated NaCl aqueous solution, 100 ml×3. The organic layer was dried over anhydrous sodium sulfate overnight, the drying agent was removed by filtration, and the solvent was removed under reduced pressure, to obtain 55.7 g of 3-[(2-cyclopentyl-2-hydroxyl-2-phenyl)ethoxyl]-1-azabicyclo[2,2,2]octane free alkali as a red oily matter, with the yield of 97.39%. The obtained product was (2R,3S),(2S,3S) configurations of 3-[(2-cyclopentyl-2-hydroxyl-2-phenyl)ethoxyl]-1-azabicyclo[2,2,2]octane free alkali.

Step 3: Purification of 3-[(2-cyclopentyl-2-hydroxyl-2-phenyl)ethoxyl]-1-azabicyclo[2,2,2]octane free alkali by Column Chromatography and Related Purification Treatment Literature[3] (3. Bingdahl B, Resul B and Dahlbom R. Facile preparation of the enantiomers of 3-acetoxyquinuclidine and 3-quinuclidinol. Acta Pharm Suec, 1979;16:281-283), and literatures[4-5] (4. Jianhua Gao, Guangling Wen, Qikai Zhang, Synthesis and separation of optically pure hydroxyl ether compounds. Acta Pharmaceutica Sinica, 1987;22(9):708-710; 5. Xiangyu Han. Study on the stereoselective synthesis of chiral M receptor antagonists. Reports from Postdoctoral Research Station in Academy of Military Medical Sciences, p 39-40, 2005, Beijing. (Medical Library of Chinese PLA: R914, 20050537)) reported that chiral R or S configuration of 3-quinuclidinol as a raw material was reacted with racemate of 2-phenyl-2-cyclopentyloxirane or R or S enantiomer thereof, and four optical isomers could be then obtained by column chromatography. The above literatures have determined their absolute configurations, and in accordance with the nomenclature, the chiral carbon atom on quinuclidine of the molecule is designated as "3", and the chiral carbon linked to aryl is designated as "2". Table 1 is specific rotation data of four kinds of pure chiral optical isomers of 3-[(2-cyclopentyl-2-hydroxyl-2-phenyl)ethoxyl]-1-azabicyclo[2,2,2]octane free alkali.

TABLE 1

Data of absolute configuration and specific rotation of the compound

| Absolute configuration | Specific rotation value $[a]_D^{26}$ in literature 2 | Specific rotation value $[a]_D^{26}$ in literature 3 |
| --- | --- | --- |
| (2S,3R) | −45.29 | −46.5 |
| (2R,3R) | +8.47 | +8.3 |
| (2R,3S) | +44.8 | +45.2 |
| (2S,3S) | −8.9 | −9.2 |

Measurement conditions of specific rotation: the temperature is 26° C., the solvent is methanol, and the measurement concentration is 0.4%-1%.

The sample from the above step 2 was separated on silica gel column, using ammoniated dichloromethane or trichloromethane and methanol as mobile phase and a TLC plate to monitor the purity of the sample. Under the above elution system, a sample of a mixture of both (2R,3S) and (2S,3S) configurations of 3-[(2-cyclopentyl-2-hydroxyl-2-phenyl)ethoxyl]-1-azabicyclo[2,2,2]octane free alkali was purified into two kinds of free alkali, (2R,3S) and (2S,3S), depending on the elution sequence, thereby obtaining 23.5 g of (2R,3S)-3-[(2-cyclopentyl-2-hydroxyl-2-phenyl)ethoxyl]-1-azabicyclo[2,2,2]octane free alkali with the yield of 86.46%, and 21.1 g of (2S,3S)-3-[(2-cyclopentyl-2-hydroxyl-2-phenyl)ethoxyl]-1-azabicyclo[2,2,2]octane free alkali with the yield of 77.63%. The measured value of the specific rotation $[a]_D^{26}$ of (2R,3S) was +43.95, and the measured value of the specific rotation $[a]_D^{26}$ of (2S,3S) was −9.33.

Synthesis and identification of other pure optical isomer bases were consistent with the synthesis and separation methods for the above pure optical isomers of 3-[(2-cyclopentyl-2-hydroxyl-2-phenyl)ethoxyl]-1-azabicyclo[2,2,2]octane free alkali, and once the base was quaternized, the title compound would be obtained, and the preparation process of various title compounds would be illustrated in detail by the specific examples of synthesis of the specific compounds below. In addition, when racemic quinuclidinol was used as a starting material, the obtained base was a mixture of four kinds of optical isomers before separation by column chromatography, and the final title compound was also a mixture of four kinds of optical isomers. All of these pure optical isomers and mixtures of optical isomers in different ratios fall within the scope of the present invention.

Step 4: Preparation of 3-bromopropoxy benzene

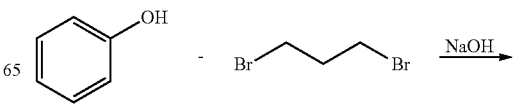

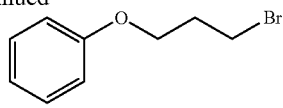

9.507 g (101 mmol) of phenol was added into a 150 ml three-necked flask, followed by the addition of 4.253 g (106 mmol) of sodium hydroxide and a solution of 52.17 g (258 mmol) of 1,3-dibromopropane in 30 ml of absolute ethanol, and the resulting mixture was then reacted under heating and refluxing in oil bath, with a white solid being precipitated, until the essentially complete reaction of phenol monitored by TLC (TLC condition: petroleum ether/ethyl acetate=5.0 ml/1.0 ml). After the reaction being completed, the solid was removed by filtration, and the solvent was removed from the filtrate at 50° C. or less under reduced pressure by a water pump, thereby obtaining an oily matter containing a white solid, to which was added petroleum ether and then left it overnight. The precipitated solid was removed by filtration, and the solvent was removed from the filtrate at 25-40° C. under reduced pressure by a water pump, thereby obtaining a yellow oily matter. The oily matter was distilled under reduced pressure, to collect a fraction at 121-123° C./8 mmHg, thereby obtaining 12.786 g of a colorless, transparent oily matter, with the yield of 58.9% and the purity of 95.60% detected by GC.

$^1$HNMR(CDCl$_3$)(ppm): δ7.17-6.77(m,5H), δ3.96(t,2H), δ3.32(t,2H), δ2.21(m,2H).

Step 5: (2R,3S)-3-[(2-cyclopentyl-2-hydroxyl-2-phenyl)ethoxyl]-1-(3-phenoxypropyl)-1-azabicyclo[2,2,2]octane bromide

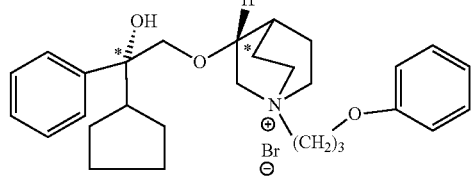

2.871 g (9.1 mmol) of (2R,3S) configuration of the base prepared in step 3 was added into a 100 ml eggplant-shaped flask and was dissolved by adding 18 ml of chloroform to obtain a yellow transparent solution, to which was added 11.034 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution by rotary evaporation at 25-40° C. under reduced pressure by a water pump, thereby obtaining a yellow oily matter, to which was added ethyl ether to precipitate a great quantity of solid, and the solid was collected by suction filtration to obtain 3.886 g of (2R,3S)-3-[(2-cyclopentyl-2-hydroxyl-2-phenyl)ethoxyl]-1-(3-phenoxypropyl)-1-azabicyclo[2,2,2]octane bromide as an off-white solid, with the yield of 80.5%. The measured value of the specific rotation [a]$_D^{26}$ of (2R,3S) was +53.56.

The compound prepared in Example 1 was reacted with Ag$_2$O to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D$_2$O)(ppm): δ7.20-6.65(m,10H), δ4.15-3.66(m, 5H), δ3.43-3.12(m,8H), δ2.13(m,2H), 2.01(m,1H), δ1.81-1.40(m,13H).

Example 2

(2S,3S)-3-[(2-cyclopentyl-2-hydroxyl-2-phenyl)ethoxyl]-1-(3-phenoxypropyl)-1-azabicyclo[2,2,2]octane bromide Steps 1, 2, 3, and 4: The Same as Steps 1, 2, 3, and 4 in [Example 1].

Step 5: (2S,3S)-3-[(2-cyclopentyl-2-hydroxyl-2-phenyl)ethoxyl]-1-(3-phenoxypropyl)-1-azabicyclo[2,2,2]octane bromide

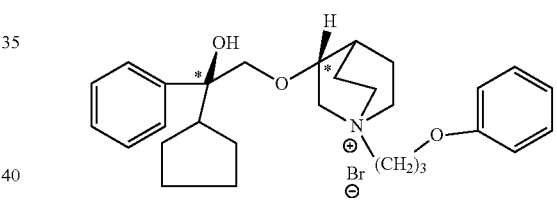

2.872 g (9.1 mmol) of (2R,3S) configuration of the base was added into a 100 ml eggplant-shaped flask and was dissolved by adding 18 ml of chloroform to obtain a yellow transparent solution, to which was added 11.032 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution by rotary evaporation at 25-40° C. under reduced pressure by a water pump, thereby obtaining a yellow oily matter, to which was added ethyl ether to precipitate a great quantity of solid, and the solid was collected by suction filtration to obtain 3.685 g of (2S,3S)-3-[(2-cyclopentyl-2-hydroxyl-2-phenyl)ethoxyl]-1-(3-phenoxypropyl)-1-azabicyclo[2,2,2]octane bromide as an off-white solid, with the yield of 75.96%. The measured value of the specific rotation [a]hd D$^{26}$ of (2S,3S) was +31.71.

The compound prepared in Example 2 was reacted with Ag$_2$O to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR($D_2O$)(ppm): δ7.22-6.66(m,10H), δ4.17-3.67(m, 5H), δ3.45-3.14(m,8H), δ2.15(m,2H), 2.03(m,1H), δ1.83-1.41(m,13H).

Example 3

(2S,3R)-3-[(2-cyclopentyl-2-hydroxyl-2-phenyl) ethoxyl]-1-(3-phenoxypropyl)-1-azabicyclo[2,2,2] octane bromide Step 1: The Same as Step 1 in [Example 1]

Step 2: Preparation of 3-[(2-cyclopentyl-2-hydroxyl-2-phenyl)ethoxyl]-1-azabicyclo[2,2,2]octane free alkali from R-3-quinuclidinol

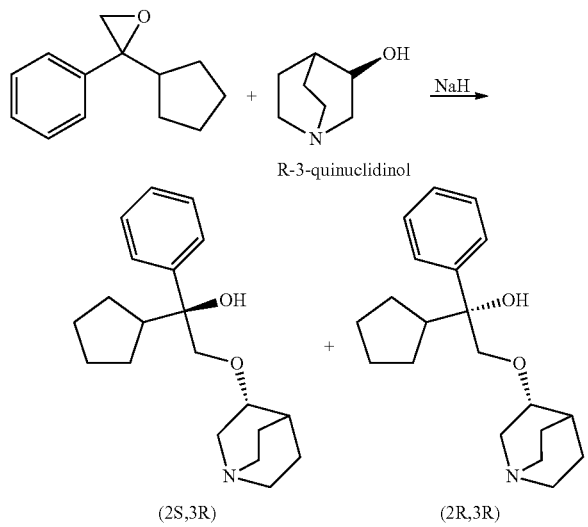

To 18.721 g (147 mmol) of commercially available R-3-quinuclidinol was added 190 ml DMSO, followed by the addition of 47.558 g (190 mmol) of sodium hydride, and the mixture was reacted at 20-60° C. for 0.5-12 h, and then cooled to room temperature, and a solution of 35.75 g (190 mmol) of 1-phenyl-1-cyclopentyloxirane (self-prepared) in 45 ml DMSO was added thereto, and after the completion of dropping, the resulting mixture was heated at 20-70° C. in oil bath to react for 0.5-12 hours. Under the condition of ice bath, 120 ml of ice water was added at an inner temperature of 30° C. or less. The reaction mixture was extracted with isopropyl ether, 100 ml×3; and the ether layer was combined and washed with a saturated NaCl aqueous solution, 100 ml×3. The organic layer was dried over anhydrous sodium sulfate overnight, the drying agent was removed by filtration, and the solvent was removed under reduced pressure, to obtain 54.67 g of 3-[(2-cyclopentyl-2-hydroxyl-2-phenyl) ethoxyl]-1-azabicyclo[2,2,2]octane free alkali as a red oily matter, with the yield of 95.6%. The obtained product was (2R,3R),(2S,3R)-3-[(2-cyclopentyl-2-hydroxyl-2-phenyl) ethoxyl]-1-azabicyclo[2,2,2]octane free alkali.

Step 3: Purification of 3-[(2-cyclopentyl-2-hydroxyl-2-phenyl)ethoxyl]-1-azabicyclo[2,2,2]octane free alkali by Column Chromatography and Related Purification Treatment The sample from the above step 2 was separated on silica gel column, using ammoniated dichloromethane or trichloromethane and methanol as mobile phase and a TLC plate to monitor the purity of the sample. Under the above elution system, a sample of a mixture of both (2R,3R) and (2S,3R) configurations of 3-[(2-cyclopentyl-2-hydroxyl-2-phenyl) ethoxyl]-1-azabicyclo[2,2,2]octane free alkali could be purified into two kinds of free alkali, (2R,3R) and (2S,3R), depending on the elution sequence, thereby obtaining 21.5 g of (2R,3R) configuration of 3-[(2-cyclopentyl-2-hydroxyl-2-phenyl)ethoxyl]-1-azabicyclo[2,2,2]octane free alkali with the yield of 79.1% and the measured value of the specific rotation [a]hd $D^{26}$ of +9.01, and 21.3 g of (2S,3R) configuration of 3-[(2-cyclopentyl-2-hydroxyl-2-phenyl) ethoxyl]-1-azabicyclo[2,2,2]octane free alkali with the yield of 78.37% and the measured value of the specific rotation [a]hd $D^{26}$ of −44.20.

Step 4: The Same as Step 4 in [Example 1]

Step 5: (2S,3R)-3-[(2-cyclopentyl-2-hydroxyl-2-phenyl)ethoxyl]-1-(3-phenoxypropyl)-1-azabicyclo [2,2,2]octane bromide

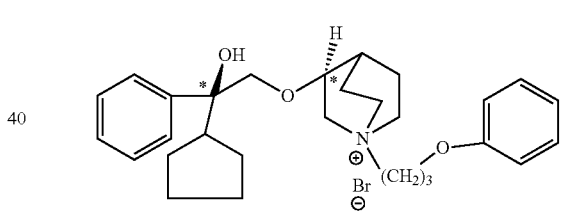

2.871 g (9.1 mmol) of (2S,3R) configuration of the base was added into a 100 ml eggplant-shaped flask and was dissolved by adding 18 ml of chloroform to obtain a yellow transparent solution, to which was added 11.0340 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution by rotary evaporation at 25-40° C. under reduced pressure by a water pump, thereby obtaining a yellow oily matter, to which was added ethyl ether to precipitate a great quantity of solid, and the solid was collected by suction filtration to obtain 3.86 g of (2S,3R) configuration of 3-[(2-cyclopentyl-2-hydroxyl-2-phenyl)ethoxyl]-1-(3-phenoxypropyl)-1-azabicyclo[2,2,2]octane bromide as an off-white solid, with the yield of 79.95%. The measured value of the specific rotation [a]hd $D^{26}$ was −58.16.

The compound prepared in Example 3 was reacted with $Ag_2O$ to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR($D_2O$)(ppm): δ7.21-6.86(m,10H), δ4.15-3.66(m, 5H), δ3.43-3.13(m,8H), δ2.16(m,2H), 2.04(m,1H), δ1.79-1.23(m,13H).

Example 4

(2R,3R)-3-[(2-cyclopentyl-2-hydroxyl-2-phenyl)ethoxyl]-1-(3-phenoxypropyl)-1-azabicyclo[2,2,2]octane bromide Step 1: The Same as Step 1 in [Example 1]

Steps 2 and 3: The Same as Steps 2 and 3 in [Example 3]

Step 4: The Same as Step 4 in [Example 1]

Step 5: (2R,3R)-3-[(2-cyclopentyl-2-hydroxyl-2-phenyl)ethoxyl]-1-(3-phenoxypropyl)-1-azabicyclo[2,2,2]octane bromide

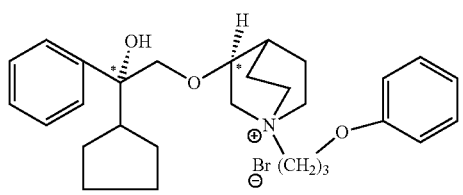

2.87 g (9.1 mmol) of (2R,3R) configuration of the base was added into a 100 ml eggplant-shaped flask and was dissolved by adding 18 ml of chloroform to obtain a yellow transparent solution, to which was added 11.034 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution by rotary evaporation at 25-40° C. under reduced pressure by a water pump, thereby obtaining a yellow oily matter, to which was added ethyl ether to precipitate a great quantity of solid, and the solid was collected by suction filtration to obtain 3.685 g of (2R,3R) configuration of 3-[(2-cyclopentyl-2-hydroxyl-2-phenyl)ethoxyl]-1-(3-phenoxypropyl)-1-azabicyclo[2,2,2]octane bromide as an off-white solid, with the yield of 76.34%. The measured value of the specific rotation [a]hd $D^{26}$ was −31.18.

The compound prepared in Example 4 was reacted with $Ag_2O$ to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR($D_2O$)(ppm): δ7.22-6.87(m,10H), δ4.17-3.65(m, 5H), δ3.45-3.15(m,8H), δ2.17(m,2H), 2.05(m,1H), δ1.80-1.26(m,13H).

Example 5

(2R,3S),(2S,3R)-3-[(2-cyclopentyl-2-hydroxyl-2-phenyl)ethoxyl]-1-(3-phenoxypropyl)-1-azabicyclo[2,2,2]octane bromide Step 1: The Same as step 1 in [Example 1]

Step 2: Preparation of 3-[(2-cyclopentyl-2-hydroxyl-2-phenyl)ethoxyl]-1-azabicyclo[2,2,2]octane free alkali from racemic quinuclidinol

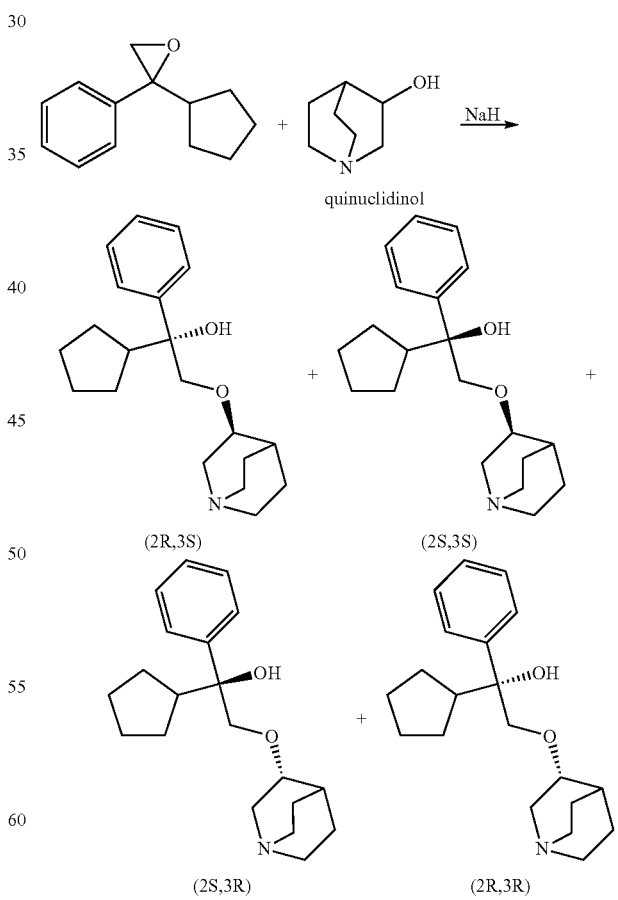

To 18.72 g (147 mmol) of commercially available racemic quinuclidinol was added 190 ml DMSO, followed by the addition of 7.59 g (190 mmol) of sodium hydride, and the mixture was reacted at 20-60° C. for 0.5-12 h, and then cooled to room temperature, and a solution of 35.68 g (190 mmol) of 1-phenyl-1-cyclopentyloxirane (self-prepared) in 45 ml DMSO was added thereto, and after the completion of dropping, the resulting mixture was heated at 20-70° C. in oil bath to react for 0.5-12 hours. Under the condition of ice bath, 120 ml of ice water was added at an inner temperature of 30° C. or less. The reaction mixture was extracted with isopropyl ether, 100 ml×3; and the ether layer was combined and washed with a saturated NaCl aqueous solution, 100 ml×3. The organic layer was dried over anhydrous sodium sulfate overnight, the drying agent was removed by filtration, and the solvent was removed under reduced pressure, to obtain 51.99 g of 3-[(2-cyclopentyl-2-hydroxyl-2-phenyl) ethoxyl]-1-azabicyclo[2,2,2]octane free alkali as a red oily matter, with the yield of 90.92%. The obtained product was (2R,2S),(2R,3R),(2S,3R),(2S,3S)-3-[(2-cyclopentyl-2-hydroxyl-2-phenyl)ethoxyl]-1-azabicyclo[2,2,2]octane free alkali.

Step 3: Purification of 3-[(2-cyclopentyl-2-hydroxyl-2-phenyl)ethoxyl]-1-azabicyclo[2,2,2]octane free alkali by Column Chromatography and Related Purification Treatment The sample from the above step 2 was separated on silica gel column, using ammoniated dichloromethane or trichloromethane and methanol as mobile phase and a TLC plate to monitor the purity of the sample. Under the above elution system, a sample of a mixture of four configurations of (2R,3S),(2R,3R),(2S,3R),(2S,3S) of 3-[(2-cyclopentyl-2-hydroxyl-2-phenyl) ethoxyl]-1-azabicyclo[2,2,2]octane free alkali could be purified into two kinds of racemic free alkali, (2R,3S),(2S,3R) and (2R,3R),(2S,3S), depending on the elution sequence, wherein the firstly eluted fraction from column was 22.05 g of (2R,3S),(2S,3R) racemic configurations of 3-[(2-cyclopentyl-2-hydroxyl-2-phenyl)ethoxyl]-1-azabicyclo[2,2,2]octane free alkali, with the yield of 81.12%; and the secondly eluted fraction from column was 21.29 g of (2R,3R),(2S,3S) configurations of 3-[(2-cyclopentyl-2-hydroxyl-2-phenyl)ethoxyl]-1-azabicyclo[2,2,2] octane free alkali, with the yield of 78.33%.

Step 4: The Same as Step 4 in [Example 1]

Step 5: (2R,3S),(2S,3R) Configuration of 3-[(2-cyclopentyl-2-hydroxyl-2-phenyl) ethoxyl]-1-(3-phenoxypropyl)-1-azabicyclo[2,2,2]octane bromide

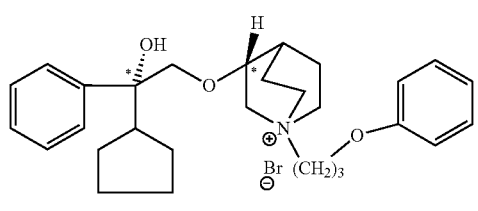

+

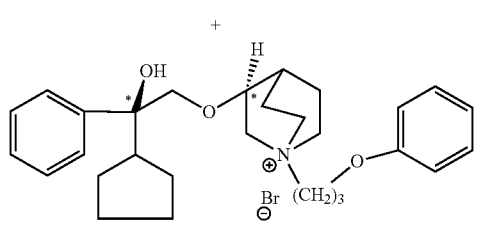

2.871 g (9.1 mmol) of (2R,3S),(2S,3R) configuration of the base was added into a 100 ml eggplant-shaped flask and was dissolved by adding 18 ml of chloroform to obtain a yellow transparent solution, to which was added 11.035 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution by rotary evaporation at 25-40° C. under reduced pressure by a water pump, thereby obtaining a yellow oily matter, to which was added ethyl ether to precipitate a great quantity of solid, and the solid was collected by suction filtration to obtain 3.46 g of (2R,3S),(2S,3R)-3-[(2-cyclopentyl-2-hydroxyl-2-phenyl)ethoxyl]-1-(3-phenoxypropyl)-1-azabicyclo[2,2,2]octane bromide as an off-white solid, with the yield of 71.66%.

The compound prepared in Example 5 was reacted with $Ag_2O$ to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR($D_2O$) δ(ppm): 7.19-7.15(m,7H), 6.82-6.77(m, 3H), 3.94-3.45(m,5H), 3.24-3.12(m,8H), 2.15(m,2H), 1.96-1.79(m,2H), 1.57-1.25(m,12H).

Example 6

(2R,3R),(2S,3S) Configuration of 3-[(2-cyclopentyl-2-hydroxyl-2-phenyl)ethoxyl]-1-(3-phenoxypropyl)-1-azabicyclo[2,2,2]octane bromide Step 1: The Same as Step 1 in [Example 1]

Steps 2 and 3: The Same as Steps 2 and 3 in [Example 5]

Step 4: The Same as Step 4 in Example 1

Step 45: (2R,3R),(2S,3S) configuration of 3-[(2-cyclopentyl-2-hydroxyl-2-phenyl)ethoxyl]-1-(3-phenoxypropyl)-1-azabicyclo[2,2,2]octane bromide

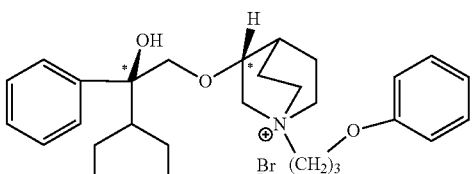

+

-continued

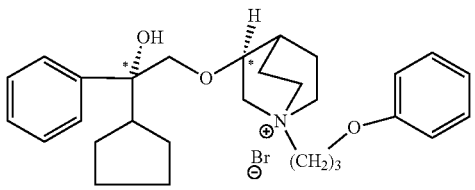

2.87 g (9.1 mmol) of (2R,3R),(2S,3S) configuration of the base was added into a 100 ml eggplant-shaped flask and was dissolved by adding 18 ml of chloroform to obtain a yellow transparent solution, to which was added 11.034 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution by rotary evaporation at 25-40° C. under reduced pressure by a water pump, thereby obtaining a yellow oily matter, to which was added ethyl ether to precipitate a great quantity of solid, and the solid was collected by suction filtration to obtain 3.58 g of (2R,3R),(2S,3S) configuration of 3-[(2-cyclopentyl-2-hydroxyl-2-phenyl)ethoxyl]-1-(3-phenoxypropyl)-1-azabicyclo[2,2,2]octane bromide as an off-white solid, with the yield of 74.17%.

The pure optical isomers of four configurations of (2R,3S),(2R,3R),(2S,3R),(2S,3S) of 3-[(2-cyclopentyl-2-hydroxyl-2-phenyl)ethoxyl]-1-azabicyclo[2,2,2]octane free alkali could be obtained from Examples 1 and 3, and mixtures of (2R,3S),(2R,3R),(2S,3R),(2S,3S) configurations of 3-[(2-cyclopentyl-2-hydroxyl-2-phenyl)ethoxyl]-1-(3-phenoxypropyl)-1-azabicyclo[2,2,2]octane bromide in different ratios were obtained by mixing these isomers in any amount and any ratio followed by quaternization by adding 3-bromopropoxy benzene.

The compound prepared in Example 6 was reacted with Ag$_2$O to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D$_2$O) δ(ppm): 7.18-7.16(m,7H), 6.81-6.75(m, 3H), 3.94-3.45 (m,5H), 3.25-3.11(m,8H), 2.13(m,2H), 1.97-1.78 (m,2H), 1.56-1.24 (m,12H).

Example 7

(2S,3R)-3-[(2-cyclohexyl-2-hydroxyl-2-phenyl)ethoxyl]-1-(3-phenoxypropyl)-1-azabicyclo[2,2,2]octane bromide Step 1: Preparation of 1-phenyl-1-cyclohexyloxirane

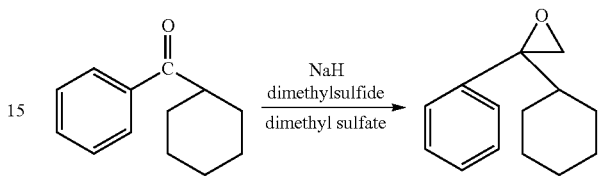

Commercially available cyclohexyl phenyl ketone as a starting material was reacted to obtain 1-phenyl-1-cyclohexyloxirane according to literature[1].

1880 ml of acetonitrile was added into a 3 L three-necked flask, followed by the addition of dimethyl sulfide and dimethyl sulfate, with a mild heat release, and the resulting mixture was stirred at room temperature for 1.5 h and then left it overnight. NaH (60%) was added portionwise into the reaction solution with stirring over 30-40 min, with gas being generated (pay attention to having the flask externally connected to an allihn condenser and a drying tube of anhydrous calcium chloride), and then stirred at room temperature for 1 hour, followed by the dropwise addition of 332.26 g of cyclohexyl phenyl ketone over about 10 min, and the resulting mixture was subsequently reacted in oil bath at 40-45° C. for 90 min after being stirred at room temperature for 20 min, and then cooled at room temperature and left it overnight. The reaction solution was transferred into an eggplant-shaped flask, the solvent was removed by suction using a water pump (40-42° C., −0.095 MPa), and the remaining solid was then cooled to 0-5° C. in ice bath, followed by the dropwise addition of 2630 ml of ice water (with the inner temperature being controlled at 0-5° C.) over about 1 hour, and the reaction solution was extracted with isopropyl ether (650 ml×3), the ether layer was combined and washed with water until it is neutral (with the pH of water washings being 7.0), and the ether layer was dried over anhydrous sodium sulfate overnight. The drying agent was removed by filtration, the solvent was removed under reduced pressure by suction using a water pump (40-42° C., −0.095 MPa), and 291.13 g of fraction at 117-127° C./3 mmHg was further collected under reduced pressure by using an oil pump.

$^1$HNMR(CDCl$_3$) δ(ppm): 7.18-7.10(m,5H), 2.91-2.66(m, 2H), 2.13-1.27(m,11H).

Step 2: Preparation of 3-[(2-cyclohexyl-2-hydroxyl-2-phenyl)ethoxyl]-1-azabicyclo[2,2,2]octane free alkali from S-3-quinuclidinol

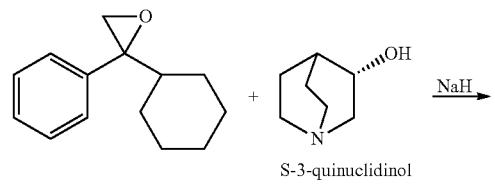

S-3-quinuclidinol

-continued

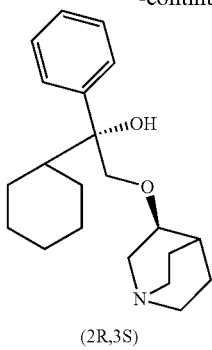

(2R,3S)

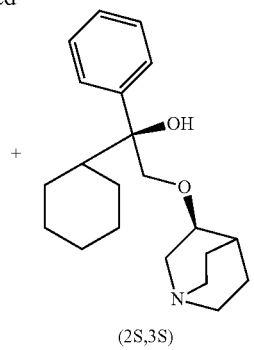

(2S,3S)

To 18.72 g (147 mmol) of commercially available S-3-quinuclidinol was added 190 ml DMSO, followed by the addition of 7.59 g (190 mmol) of sodium hydride, and the mixture was reacted at 20-60° C. for 0.5-12 h, and then cooled to room temperature, and a solution of 38.38 g (190 mmol) of 1-phenyl-1-cyclohexyloxirane (self-prepared) in 45 ml DMSO was added thereto, and after the completion of dropping, the resulting mixture was heated at 20-70° C. in oil bath to react for 0.5-12 hours. Under the condition of ice bath, 120 ml of ice water was added at an inner temperature of 30° C. or less. The reaction mixture was extracted with isopropyl ether, 100 ml×3; and the ether layer was combined and washed with a saturated NaCl aqueous solution, 100 ml×3. The organic layer was dried over anhydrous sodium sulfate overnight, the drying agent was removed by filtration, and the solvent was removed to obtain 47.102 g of 3-[(2-cyclohexyl-2-hydroxyl-2-phenyl)ethoxyl]-1-azabicyclo[2,2,2]octane free alkali as a red oily matter, with the yield of 97.39%. The obtained product was (2R,3S),(2S,3S)-3-[(2-cyclohexyl-2-hydroxyl-2-phenyl)ethoxyl]-1-azabicyclo[2,2,2]octane free alkali.

Step 3: Purification of 3-[(2-cyclohexyl-2-hydroxyl-2-phenyl)ethoxyl]-1-azabicyclo[2,2,2]octane free alkali by Column Chromatography and Related Purification Treatment The sample from the above step 2 was separated on silica gel column, using ammoniated dichloromethane or trichloromethane and methanol as mobile phase and a TLC plate to monitor the purity of the sample. Under the above elution system, a sample of a mixture of both (2R,3S) and (2S,3S) configurations of 3-[(2-cyclohexyl-2-hydroxyl-2-phenyl) ethoxyl]-1-azabicyclo[2,2,2]octane free alkali could be purified into two kinds of free alkali, (2R,3S) and (2S,3S), depending on the elution sequence, thereby obtaining 20.282 g of (2R,3S) configuration of 3-[(2-cyclohexyl-2-hydroxyl-2-phenyl)ethoxyl]-1-azabicyclo[2,2,2]octane free alkali with the yield of 86.12%, and 20.63 g of (2S,3S) configuration of 3-[(2-cyclohexyl-2-hydroxyl-2-phenyl) ethoxyl]-1-azabicyclo[2,2,2]octane free alkali with the yield of 87.6%.

Step 4: The Same as Step 4 in [Example 1]

Step 5: (2R,3S)-3-[(2-cyclohexyl-2-hydroxyl-2-phenyl)ethoxyl]-1-(3-phenoxypropyl)-1-azabicyclo[2,2,2]octane bromide

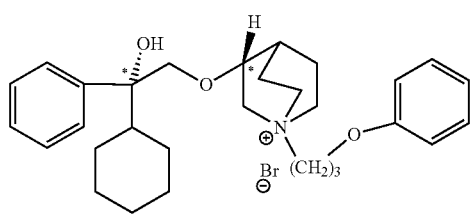

2.994 g (9.1 mmol) of (2R,3S) configuration of the base was added into a 100 ml eggplant-shaped flask and was dissolved by adding 18 ml of chloroform to obtain a yellow transparent solution, to which was added 11.034 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution by rotary evaporation at 25-40° C. under reduced pressure by a water pump, thereby obtaining a yellow oily matter, to which was added ethyl ether to precipitate a great quantity of solid, and the solid was collected by suction filtration to obtain 4.050 g of (2R,3S)-3-[(2-cyclohexyl-2-hydroxyl-2-phenyl)ethoxyl]-1-(3-phenoxypropyl)-1-azabicyclo[2,2,2]octane bromide as an off-white solid, with the yield of 81.82%.

The compound prepared in Example 7 was reacted with $Ag_2O$ to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR($D_2O$) δ(ppm): 7.16-7.14(m,7H), 6.80-6.77(m, 3H), 3.93-3.42(m,5H), 3.24-3.19(m,8H), 2.14 (m,2H), 1.89-1.79 (m, 2H), 1.57-1.27(m, 14H).

Example 8

(2S,3S)-3-[(2-cyclohexyl-2-hydroxyl-2-phenyl)ethoxyl]-1-(3-phenoxypropyl)-1-azabicyclo[2,2,2]octane bromide Steps 1, 2, 3, and 4 Were the Same as Steps 1, 2, 3, and 4 in [Example 7]

Step 4 was the Same as Step 4 in [Example 1]

Step 5: (2S,3S)-3-[(2-cyclohexyl-2-hydroxyl-2-phenyl)ethoxyl]-1-(3-phenoxypropyl)-1-azabicyclo[2,2,2]octane bromide

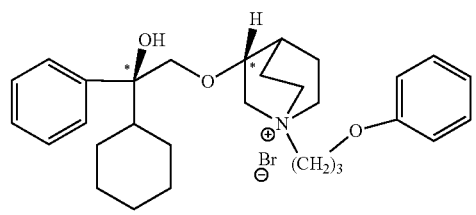

2.993 g (9.1 mmol) of (2S,3S) configuration of the base was added into a 100 ml eggplant-shaped flask and was dissolved by adding 18 ml of chloroform to obtain a yellow transparent solution, to which was added 11.035 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution by rotary evaporation at 25-40° C. under reduced pressure by a water pump, thereby obtaining a yellow oily matter, to which was added ethyl ether to precipitate a great quantity of solid, and the solid was collected by suction filtration to obtain 4.115 g of (2S,3S)-3-[(2-cyclohexyl-2-hydroxyl-2-phenyl)ethoxyl]-1-(3-phenoxypropyl)-1-azabicyclo[2,2,2] octane bromide as an off-white solid, with the yield of 83.13%.

The compound prepared in Example 8 was reacted with $Ag_2O$ to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1HNMR(D_2O)$ δ(ppm): 7.15-7.14(m,7H), 6.82-6.76(m, 3H), 3.94-3.41(m,5H), 3.23-3.18(m,8H), 2.14(m,2H), 1.89-1.79 (m, 2H), 1.58-1.27 (m, 14H).

Example 9

(2R,3R)-3-[(2-cyclohexyl-2-hydroxyl-2-phenyl)ethoxyl]-1-(3-phenoxypropyl)-1-azabicyclo[2,2,2]octane bromide Step 1: The Same as Step 1 in [Example 7]

Step 2: Preparation of 3-[(2-cyclohexyl-2-hydroxyl-2-phenyl)ethoxyl]-1-azabicyclo[2,2,2]octane free alkali from R-3-quinuclidinol

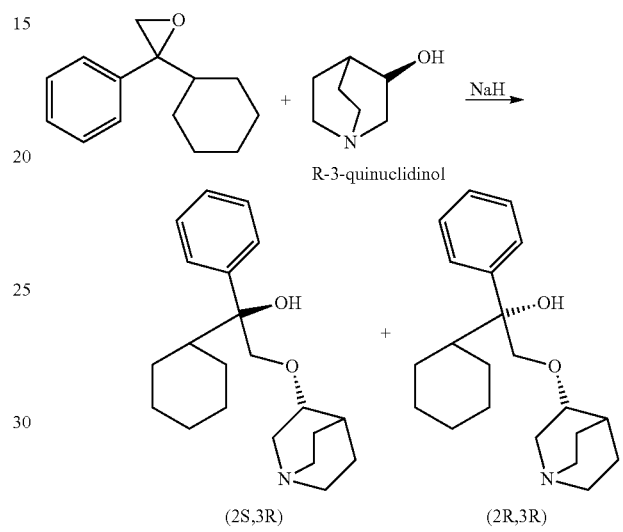

To 18.72 g (147 mmol) of commercially available R-3-quinuclidinol was added 190 ml DMSO, followed by the addition of 7.591 g (190 mmol) of sodium hydride, and the mixture was reacted at 20-60° C. for 0.5-12 h, and then cooled to room temperature, and a solution of 38.38 g (190 mmol) of 1-phenyl-1-cyclohexyloxirane (self-prepared) in 45 ml DMSO was added thereto, and after the completion of dropping, the resulting mixture was heated at 20-70° C. in oil bath to react for 0.5-12 hours. Under the condition of ice bath, 120 ml of ice water was added at an inner temperature of 30° C. or less. The reaction mixture was extracted with isopropyl ether, 100 ml×3; and the ether layer was combined and washed with a saturated NaCl aqueous solution, 100 ml×3. The organic layer was dried over anhydrous sodium sulfate overnight, the drying agent was removed by filtration, and the solvent was removed by rotary evaporation, to obtain 45.89 g of 3-[(2-cyclohexyl-2-hydroxyl-2-phenyl)ethoxyl]-1-azabicyclo[2,2,2]octane free alkali as a red oily matter, with the yield of 96.19%. The obtained product was (2R,3R),(2S,3R) configuration of 3-[(2-cyclohexyl-2-hydroxyl-2-phenyl)ethoxyl]-1-azabicyclo[2,2,2]octane free alkali.

Step 3: Purification of 3-[(2-cyclohexyl-2-hydroxyl-2-phenyl)ethoxyl]-1-azabicyclo[2,2,2]octane free alkali by column chromatography and related purification treatment The sample from the above step 2 was separated on silica gel column, using ammoniated dichloromethane or trichloromethane and methanol as mobile phase and a TLC plate to monitor the purity of the sample. Under the above elution system, a sample of a mixture of both (2R,3R) and (2S,3R) configurations of 3-[(2-cyclohexyl-2-hydroxyl-2-phenyl)ethoxyl]-1-azabicyclo[2,2,2]octane free alkali could be purified into two kinds of free alkali, (2R,3R) and (2S,3R), depending on the elution sequence, thereby obtaining 19.393 g of (2R,3R)-3-[(2-cyclohexyl-2-hydroxyl-2-phenyl)ethoxyl]-1-azabicyclo[2,2,2]octane free alkali with the yield of 84.52%, and 18.186 g of (2S,3R)-3-[(2-cyclohexyl-2-hydroxyl-2-phenyl)ethoxyl]-1-azabicyclo[2,2,2]octane free alkali with the yield of 79.26%.

Step 4: The Same as Step 4 in [Example 1]

Step 5: (2S,3R) Configuration of 3-[(2-cyclohexyl-2-hydroxyl-2-phenyl)ethoxyl]-1-(3-phenoxypropyl)-1-azabicyclo[2,2,2]octane bromide

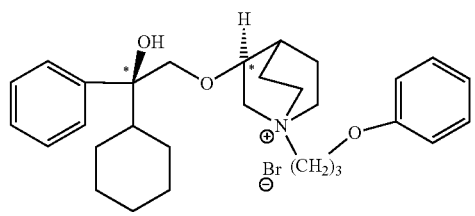

2.993 g (9.1 mmol) of (2S,3R) configuration of the base was added into a 100 ml eggplant-shaped flask and was dissolved by adding 18 ml of chloroform to obtain a yellow transparent solution, to which was added 11.0340 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution by rotary evaporation at 25-40° C. under reduced pressure by a water pump, thereby obtaining a yellow oily matter, to which was added ethyl ether to precipitate a great quantity of solid, and the solid was collected by suction filtration to obtain 4.11 g of (2S,3R)-3-[(2-cyclohexyl-2-hydroxyl-2-phenyl)ethoxyl]-1-(3-phenoxypropyl)-1-azabicyclo[2,2,2]octane bromide as an off-white solid, with the yield of 83.03%.

The compound prepared in Example 9 was reacted with $Ag_2O$ to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR($D_2O$) δ(ppm): 7.16-7.14(m,7H), 6.80-6.77(m, 3H), 3.93-3.42(m,5H), 3.24-3.19(m,8H), 2.14(m,2H), 1.89-1.79 (m, 2H), 1.57-1.27 (m, 14H).

Example 10

(2R,3R)-3-[(2-cyclohexyl-2-hydroxyl-2-phenyl)ethoxyl]-1-(3-phenoxypropyl)-1-azabicyclo[2,2,2]octane bromide Step 1: The Same as Step 1 in [Example 7]

Steps 2 and 3 Were the Same as Steps 2 and 3 in [Example 9]

Step 4: The Same as Step 4 in [Example 1]

Step 5: (2R,3R)-3-[(2-cyclohexyl-2-hydroxyl-2-phenyl)ethoxyl]-1-(3-phenoxypropyl)-1-azabicyclo[2,2,2]octane bromide

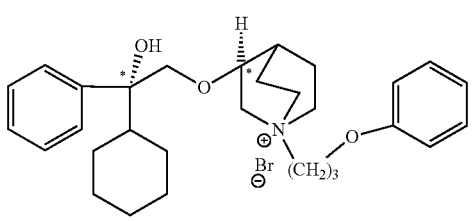

2.995 g (9.1 mmol) of (2R,3R) configuration of the base was added into a 100 ml eggplant-shaped flask and was dissolved by adding 18 ml of chloroform to obtain a yellow transparent solution, to which was added 11.034 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. under reduced pressure by a water pump, thereby obtaining a yellow oily matter, to which was added ethyl ether to precipitate a great quantity of solid, and the solid was collected by suction filtration to obtain 4.205 g of (2R,3R)-3-[(2-cyclohexyl-2-hydroxyl-2-phenyl)ethoxyl]-1-(3-phenoxypropyl)-1-azabicyclo[2,2,2]octane bromide as an off-white solid, with the yield of 84.95%.

The compound prepared in Example 10 was reacted with $Ag_2O$ to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR($D_2O$) δ(ppm): 7.16-7.14(m,7H), 6.81-6.77(m, 3H), 3.93-3.42(m,5H), 3.24-3.19(m,8H), 2.14(m,2H), 1.89-1.78(m, 2H), 1.57-1.27 (m, 14H).

Example 11

(2R,3S),(2S,3R) Configuration of 3-[(2-cyclohexyl-2-hydroxyl-2-phenyl)ethoxyl]-1-(3-phenoxypropyl)-1-azabicyclo[2,2,2]octane bromide Step 1: The Same as Step 1 in [Example 7]

Step 2: Preparation of 3-[(2-cyclohexyl-2-hydroxyl-2-phenyl)ethoxyl]-1-azabicyclo[2,2,2]octane free alkali from racemic quinuclidinol

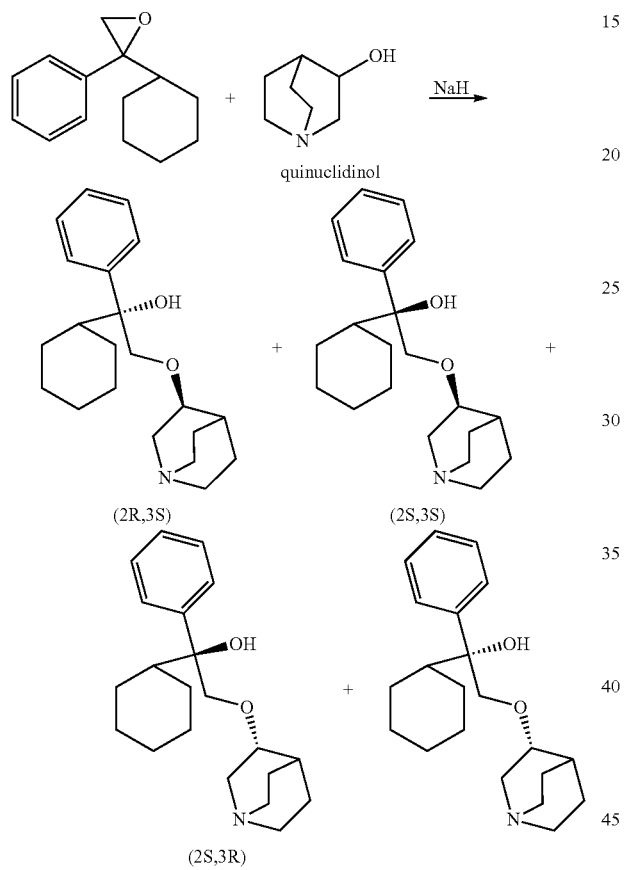

To 18.72 g (147 mmol) of commercially available racemic quinuclidinol was added 190 ml DMSO, followed by the addition of 7.59 g (190 mmol) of sodium hydride, and the mixture was reacted at 20-60° C. for 0.5-12 h, and then cooled to room temperature, and a solution of 38.42 g (190 mmol) of 1-phenyl-1-cyclohexyloxirane (self-prepared) in 45 ml DMSO was added thereto, and after the completion of dropping, the resulting mixture was heated at 20-70° C. in oil bath to react for 0.5-12 hours. Under the condition of ice bath, 120 ml of ice water was added at an inner temperature of 30° C. or less. The reaction mixture was extracted with isopropyl ether, 100 ml×3; and the ether layer was combined and washed with a saturated NaCl aqueous solution, 100 ml×3. The organic layer was dried over anhydrous sodium sulfate overnight, the drying agent was removed by filtration, and the solvent was removed under reduced pressure, to obtain 43.58 g of 3-[(2-cyclohexyl-2-hydroxyl-2-phenyl)ethoxyl]-1-azabicyclo[2,2,2]octane free alkali as a red oily matter, with the yield of 90.12%. The obtained product was (2R,3S),(2R,3R),(2S,3R),(2S,3S) configuration of 3-[(2-cyclohexyl-2-hydroxyl-2-phenyl)ethoxyl]-1-azabicyclo[2,2,2]octane free alkali.

Step 3: Purification of 3-[(2-cyclohexyl-2-hydroxyl-2-phenyl)ethoxyl]-1-azabicyclo[2,2,2]octane free alkali by Column Chromatography and Related Purification Treatment The sample from the above step 2 was separated on silica gel column, using ammoniated dichloromethane or trichloromethane and methanol as mobile phase and a TLC plate to monitor the purity of the sample. Under the above elution system, a sample of a mixture of four configurations of (2R,3S),(2R,3R),(2S,3R),(2S,3S) of 3-[(2-cyclohexyl-2-hydroxyl-2-phenyl)ethoxyl]-1-azabicyclo[2,2,2]octane free alkali could be purified into two kinds of racemic free alkali, (2R,3S),(2S,3R) and (2R,3R),(2S,3S), depending on the elution sequence, thereby obtaining the firstly eluted fraction of 18.06 g of (2R,3S),(2S,3R) racemic configuration of 3-[(2-cyclohexyl-2-hydroxyl-2-phenyl)ethoxyl]-1-azabicyclo[2,2,2]octane free alkali with the yield of 82.88%, and the secondly eluted fraction of 17.29 g of (2R,3R),(2S,3S) configuration of 3-[(2-cyclohexyl-2-hydroxyl-2-phenyl)ethoxyl]-1-azabicyclo[2,2,2]octane free alkali with the yield of 79.35%.

Step 4: The Same as Step 4 in [Example 1]

Step 5: (2R,3S),(2S,3R) Configuration of 3-[(2-cyclohexyl-2-hydroxyl-2-phenyl)ethoxyl]-1-(3-phenoxypropyl)-1-azabicyclo[2,2,2]octane bromide

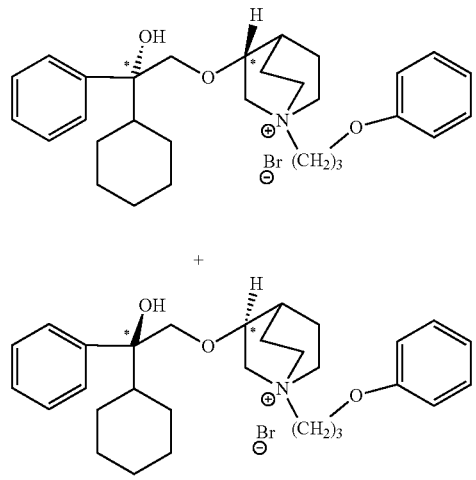

2.993 g (9.1 mmol) of (2R,3S),(2S,3R) configuration of the base was added into a 100 ml eggplant-shaped flask and was dissolved by adding 18 ml of chloroform to obtain a yellow transparent solution, to which was added 11.034 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. by rotary evaporation under reduced pressure by a water pump, thereby obtaining a yellow oily matter, to which was added ethyl ether to precipitate a great quantity of solid, and the solid was collected by suction filtration to obtain 4.026 g of (2R,3S),(2S,3R) configuration of 3-[(2-cyclohexyl-2-hydroxyl-2-phenyl)ethoxyl]-1-(3-phenoxypropyl)-1-azabicyclo[2,2,2]octane bromide as an off-white solid, with the yield of 81.36%.

The compound prepared in Example 11 was reacted with Ag$_2$O to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D$_2$O) δ(ppm): 7.19-7.15(m,7H), 6.82-6.78(m, 3H), 3.93-3.42(m,5H), 3.24-3.19(m,8H), 2.14(m,2H), 1.88-1.79 (m, 2H), 1.58-1.26(m, 14H).

Example 12

(2R,3R),(2S,3S)-3-[(2-cyclohexyl-2-hydroxyl-2-phenyl)ethoxyl]-1-(3-phenoxypropyl)-1-azabicyclo[2,2,2]octane bromide Step 1: The Same as Step 1 in [Example 7]

Steps 2 and 3: The Same as Steps 2 and 3 in [Example 11]

Step 4: The Same as Step 4 in [Example 1]

Step 5: (2R,3R),(2S,3S) Configuration of 3-[(2-cyclohexyl-2-hydroxyl-2-phenyl)ethoxyl]-1-(3-phenoxypropyl)-1-azabicyclo[2,2,2]octane bromide

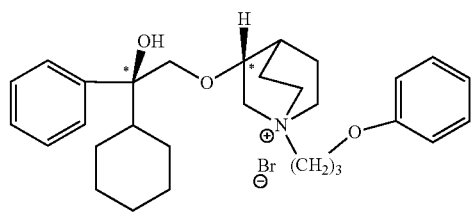

+

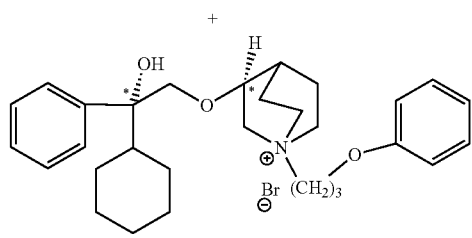

2.994 g (9.1 mmol) of (2R,3R),(2S,3S) configuration of the base was added into a 100 ml eggplant-shaped flask and was dissolved by adding 18 ml of chloroform to obtain a yellow transparent solution, to which was added 11.034 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. under reduced pressure by a water pump, thereby obtaining a yellow oily matter, to which was added ethyl ether to precipitate a great quantity of solid, and the solid was collected by suction filtration to obtain 4.125 g of (2R,3R),(2S,3S)-3-[(2-cyclohexyl-2-hydroxyl-2-phenyl)ethoxyl]-1-(3-phenoxypropyl)-1-azabicyclo[2,2,2]octane bromide as an off-white solid, with the yield of 83.36%.

The pure optical isomers of four configurations of (2R,3S),(2R,3R),(2S,3R),(2S,3S) of 3-[(2-cyclohexyl-2-hydroxyl-2-phenyl)ethoxyl]-1-azabicyclo[2,2,2]octane free alkali could be obtained from Examples 7 and 9, and mixtures of (2R,3S),(2R,3R),(2S,3R),(2S,3S) configurations of 3-[(2-cyclohexyl-2-hydroxyl-2-phenyl)ethoxyl]-1-(3-phenoxypropyl)-1-azabicyclo[2,2,2]octane bromide in different ratios were obtained by mixing these isomers in any amount and any ratio followed by quaternization by adding 3-bromopropoxy benzene.

The compound prepared in Example 12 was reacted with Ag$_2$O to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D$_2$O) δ(ppm): 7.16-7.14(m,7H), 6.80-6.77(m, 3H), 3.93-3.42(m,5H), 3.24-3.19(m,8H), 2.14(m,2H), 1.89-1.79 (m, 2H), 1.57-1.27 (m, 14H).

Example 13

(2R,3S)-3-[(2-cyclobutyl-2-hydroxyl-2-phenyl)ethoxyl]-1-(3-phenoxypropyl)-1-azabicyclo[2,2,2]octane bromide Step 1: Preparation of 1-phenyl-1-cyclobutyloxirane

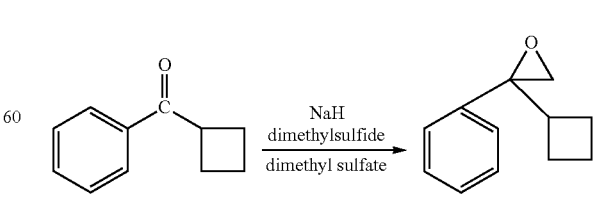

Commercially available cyclobutyl phenyl ketone as a starting material was reacted to obtain 1-phenyl-1-cyclobutyloxirane according to literature[1].

1880 ml of acetonitrile was added into a 3 L three-necked flask, followed by the addition of dimethyl sulfide and dimethyl sulfate, with a mild heat release, and the resulting mixture was stirred at room temperature for 1.5 h and then left it overnight. NaH (60%) was added portionwise into the reaction solution with stirring over 30-40 min, with gas being generated (pay attention to having the flask externally connected to an allihn condenser and a drying tube of anhydrous calcium chloride), and then stirred at room temperature for 1 hour, followed by the dropwise addition of 315.6 g of cyclobutyl phenyl ketone over about 10 min, and the resulting mixture was subsequently reacted in oil bath at 40-45° C. for 90 min after being stirred at room temperature for 20 min, and then cooled at room temperature and left it overnight. The reaction solution was transferred into an eggplant-shaped flask, the solvent was removed by suction using a water pump (40-42° C., −0.095 MPa), and the remaining solid was then cooled to 0-5° C. in ice bath, followed by the dropwise addition of 2630 ml of ice water (with the inner temperature being controlled at 0-5° C.) over about 1 hour, and the reaction solution was extracted with isopropyl ether (650 ml×3), the ether layer was combined and washed with water until it is neutral (with the pH of water washings being 7.0), and the ether layer was dried over anhydrous sodium sulfate overnight. The drying agent was removed by filtration, the solvent was removed under reduced pressure by suction using a water pump (40-42° C., −0.095 MPa), and 282.7 g of fraction at 113-126° C./3 mmHg was further collected under reduced pressure by using an oil pump, with the yield of 82.37%.

$^1$HNMR(CDCl$_3$) δ(ppm): 7.19 (m,5H),2.92-2.65(m,2H), 2.61(m,1H), 2.03-1.77(m,6H).

Step 2: Preparation of 3-[(2-cyclobutyl-2-hydroxyl-2-phenyl)ethoxyl]-1-azabicyclo[2,2,2]octane free alkali from S-3-quinuclidinol

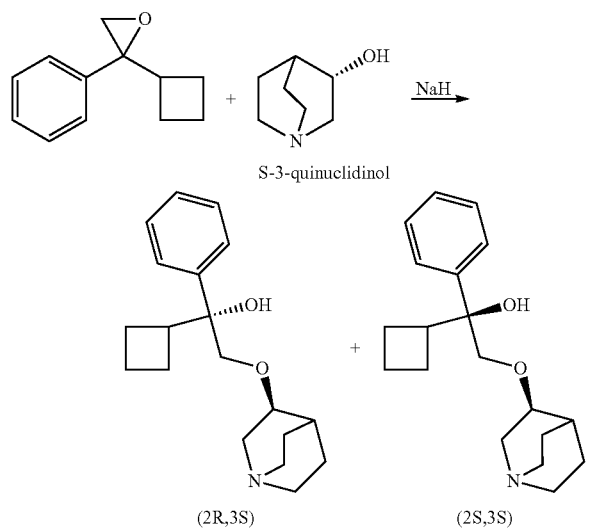

To 18.72 g (147 mmol) of commercially available S-3-quinuclidinol was added 190 ml DMSO, followed by the addition of 7.59 g (190 mmol) of sodium hydride, and the mixture was reacted at 20-60° C. for 0.5-12 h, and then cooled to room temperature, and a solution of 33.054 g (190 mmol) of 1-phenyl-1-cyclobutyloxirane (self-prepared) in 45 ml DMSO was added thereto, and after the completion of dropping, the resulting mixture was heated at 20-70° C. in oil bath to react for 0.5-12 hours. Under the condition of ice bath, 120 ml of ice water was added at an inner temperature of 30° C. or less. The reaction mixture was extracted with isopropyl ether, 100 ml×3; and the ether layer was combined and washed with a saturated NaCl aqueous solution, 100 ml×3. The organic layer was dried over anhydrous sodium sulfate overnight, the drying agent was removed by filtration, and the solvent was removed under reduced pressure to obtain 43.473 g of 3-[(2-cyclobutyl-2-hydroxyl-2-phenyl)ethoxyl]-1-azabicyclo[2,2,2]octane free alkali as a red oily matter, with the yield of 98.25%. The obtained product was (2R,3S),(2S,3S)-3-[(2-cyclobutyl-2-hydroxyl-2-phenyl)ethoxyl]-1-azabicyclo[2,2,2]octane free alkali.

Step 3: Purification of 3-[(2-cyclobutyl-2-hydroxyl-2-phenyl)ethoxyl]-1-azabicyclo[2,2,2]octane free alkali by Column Chromatography and Related Purification Treatment The sample from the above step 2 was separated on silica gel column, using ammoniated dichloromethane or trichloromethane and methanol as mobile phase and a TLC plate to monitor the purity of the sample. Under the above elution system, a sample of a mixture of both (2R,3S) and (2S,3S) configurations of 3-[(2-cyclobutyl-2-hydroxyl-2-phenyl)ethoxyl]-1-azabicyclo[2,2,2]octane free alkali could be purified into two kinds of free alkali, (2R,3S) and (2S,3S), depending on the elution sequence, thereby obtaining 17.5548 g of (2R,3S)-3-[(2-cyclobutyl-2-hydroxyl-2-phenyl)ethoxyl]-1-azabicyclo[2,2,2]octane free alkali with the yield of 80.42%, and 17.31 g of (2S,3S)-3-[(2-cyclobutyl-2-hydroxyl-2-phenyl) ethoxyl]-1-azabicyclo[2,2,2]octane free alkali with the yield of 79.62%.

Step 4: The Same as Step 4 in [Example 1]

Step 5: (2R,3S)-3-[(2-cyclobutyl-2-hydroxyl-2-phenyl)ethoxyl]-1-(3-phenoxypropyl)-1-azabicyclo[2,2,2]octane bromide

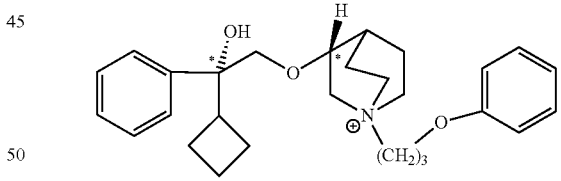

2.739 g (9.1 mmol) of (2R,3S) configuration of the base was added into a 100 ml eggplant-shaped flask and was dissolved by adding 18 ml of chloroform to obtain a yellow transparent solution, to which was added 11.034 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. under reduced pressure by a water pump, thereby obtaining a yellow oily matter, to which was added ethyl ether to precipitate a great quantity of solid, and the solid was collected by suction filtration to obtain 3.828 g of (2R,3S) configuration of 3-[(2-cyclobutyl-2-hydroxyl-2-phenyl)ethoxyl]-1-(3-phenoxypropyl)-1-azabicyclo[2,2,2]octane bromide as an off-white solid, with the yield of 81.52%.

The compound prepared in Example 13 was reacted with Ag$_2$O to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D$_2$O) δ(ppm): 7.19-7.15(m,7H), 6.82-6.77(m, 3H), 3.94-3.68m,5H), 3.49-3.19(m,9H), 2.15(m,2H), 2.0-1.79 (m, 11H).

Example 14

(2S,3S)-3-[(2-cyclobutyl-2-hydroxyl-2-phenyl)ethoxyl]-1-(3-phenoxypropyl)-1-azabicyclo[2,2,2]octane bromide Steps 1, 2, and 3 Were the Same as Steps 1, 2, and 3 in [Example 13]

Step 4 was the Same as Step 4 in [Example 1]

Step 5: (2S,3S)-3-[(2-cyclobutyl-2-hydroxyl-2-phenyl)ethoxyl]-1-(3-phenoxypropyl)-1-azabicyclo[2,2,2]octane bromide

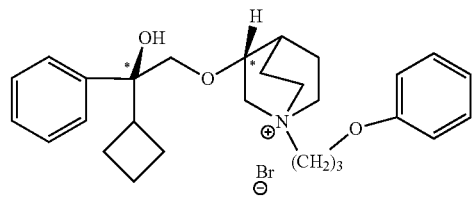

2.739 g (9.1 mmol) of (2S,3S) configuration of the base was added into a 100 ml eggplant-shaped flask and was dissolved by adding 18 ml of chloroform to obtain a yellow transparent solution, to which was added 11.034 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. under reduced pressure by a water pump, thereby obtaining a yellow oily matter, to which was added ethyl ether to precipitate a great quantity of solid, and the solid was collected by suction filtration to obtain 3.726 g of (2S,3S)-3-[(2-cyclobutyl-2-hydroxyl-2-phenyl)ethoxyl]-1-(3-phenoxypropyl)-1-azabicyclo[2,2,2]octane bromide as an off-white solid, with the yield of 79.34%.

The compound prepared in Example 14 was reacted with Ag$_2$O to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D$_2$O) δ(ppm): 7.19-7.15(m,7H), 6.82-6.77(m, 3H), 3.94-3.68m,5H), 3.49-3.19(m,9H), 2.14(m,2H), 2.0-1.79 (m, 11H).

Example 15

(2S,3R)-3-[(2-cyclobutyl-2-hydroxyl-2-phenyl)ethoxyl]-1-(3-phenoxypropyl)-1-azabicyclo[2,2,2]octane bromide Step 1 was the Same as Step 1 in [Example 13]

Step 2: Preparation of 3-[(2-cyclobutyl-2-hydroxyl-2-phenyl)ethoxyl]-1-azabicyclo[2,2,2]octane free alkali from R-3-quinuclidinol

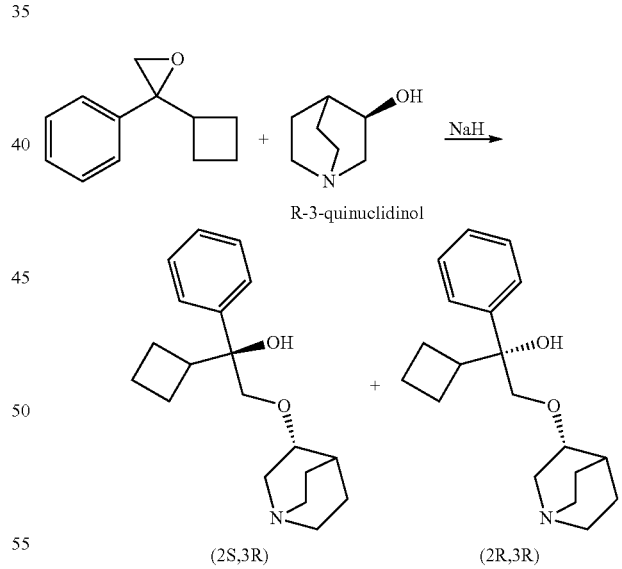

To 18.721 g (147 mmol) of commercially available R-3-quinuclidinol was added 190 ml DMSO, followed by the addition of 7.591 g (190 mmol) of sodium hydride, and the mixture was reacted at 20-60° C. for 0.5-12 h, and then cooled to room temperature, and a solution of 33.054 g (190 mmol) of 1-phenyl-1-cyclobutyloxirane (self-prepared) in 45 ml DMSO was added thereto, and after the completion of dropping, the resulting mixture was heated at 20-70° C. in oil bath to react for 0.5-12 hours. Under the condition of ice bath, 120 ml of ice water was added at an inner temperature of 30° C. or less. The reaction mixture was extracted with isopropyl ether, 100 ml×3; and the ether layer was combined and washed with a saturated NaCl aqueous solution, 100 ml×3. The organic layer was dried over anhydrous sodium sulfate overnight, the drying agent was removed by filtration, and the solvent was removed under reduced pressure to obtain 45.91 g of 3-[(2-cyclobutyl-2-hydroxyl-2-phenyl)ethoxyl]-1-azabicyclo[2,2,2]octane free alkali as a red oily matter, with the yield of 97.77%. The obtained product was (2R,3R),(2S,3R) configuration of 3-[(2-cyclobutyl-2-hydroxyl-2-phenyl)ethoxyl]-1-azabicyclo[2,2,2]octane free alkali.

Step 3: Purification of 3-[(2-cyclobutyl-2-hydroxyl-2-phenyl)ethoxyl]-1-azabicyclo[2,2,2]octane free alkali by Column Chromatography and Related Purification Treatment The sample from the above step 2 was separated on silica gel column, using ammoniated dichloromethane or trichloromethane and methanol as mobile phase and a TLC plate to monitor the purity of the sample. Under the above elution system, a sample of a mixture of both (2R,3R) and (2S,3R) configurations of 3-[(2-cyclobutyl-2-hydroxyl-2-phenyl)ethoxyl]-1-azabicyclo[2,2,2]octane free alkali could be purified into two kinds of free alkali, (2R,3R) and (2S,3R), depending on the elution sequence, thereby obtaining 18.41 g of (2R,3R)-3-[(2-cyclobutyl-2-hydroxyl-2-phenyl)ethoxyl]-1-azabicyclo[2,2,2]octane free alkali with the yield of 80.22%, and 18.27 g of (2S,3R)-3-[(2-cyclobutyl-2-hydroxyl-2-phenyl) ethoxyl]-1-azabicyclo[2,2,2]octane free alkali with the yield of 79.59%.

Step 4: The Same as Step 4 in [Example 1]

Step 5: (2S,3R)-3-[(2-cyclobutyl-2-hydroxyl-2-phenyl)ethoxyl]-1-(3-phenoxypropyl)-1-azabicyclo[2,2,2]octane bromide

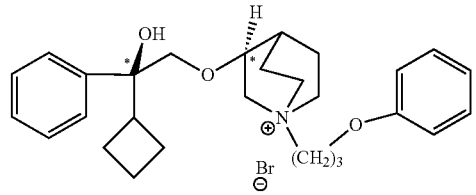

2.739 g (9.1 mmol) of (2S,3R) configuration of the base was added into a 100 ml eggplant-shaped flask and was dissolved by adding 18 ml of chloroform to obtain a yellow transparent solution, to which was added 11.0340 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. under reduced pressure by a water pump, thereby obtaining a yellow oily matter, to which was added ethyl ether to precipitate a great quantity of solid, and the solid was collected by suction filtration to obtain 3.790 g of (2S,3R)-3-[(2-cyclobutyl-2-hydroxyl-2-phenyl)ethoxyl]-1-(3-phenoxypropyl)-1-azabicyclo[2,2,2]octane bromide as an off-white solid, with the yield of 80.72%.

The compound prepared in Example 15 was reacted with $Ag_2O$ to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1HNMR(D_2O)$ δ(ppm): 7.19-7.15(m,7H), 6.82-6.77(m, 3H), 3.94-3.68m,5H), 3.49-3.19(m,9H), 2.15(m,2H), 2.0-1.79 (m, 11H).

Example 16

(2R,3R)-3-[(2-cyclobutyl-2-hydroxyl-2-phenyl)ethoxyl]-1-(3-phenoxypropyl)-1-azabicyclo[2,2,2]octane bromide Step 1: The Same as Step 1 in [Example 13]

Steps 2 and 3 Were the Same as Steps 2 and 3 in [Example 15]

Step 4: The Same as Step 4 in [Example 1]

Step 5: (2R,3R)-3-[(2-cyclobutyl-2-hydroxyl-2-phenyl)ethoxyl]-1-(3-phenoxypropyl)-1-azabicyclo[2,2,2]octane bromide

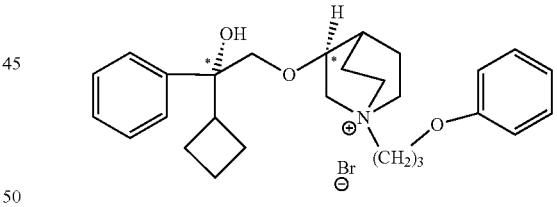

2.739 g (9.1 mmol) of (2R,3R) configuration of the base was added into a 100 ml eggplant-shaped flask and was dissolved by adding 18 ml of chloroform to obtain a yellow transparent solution, to which was added 11.034 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution by rotary evaporation at 25-40° C. under reduced pressure by a water pump, thereby obtaining a yellow oily matter, to which was added ethyl ether to precipitate a great quantity of solid, and the solid was collected by suction filtration to obtain 3.805 g of (2R,3R) configuration of 3-[(2-cyclobutyl- 2-hydroxyl-2-phenyl)ethoxyl]-1-(3-phenoxypropyl)-1-azabicyclo[2,2,2]octane bromide as an off-white solid, with the yield of 81.02%.

The compound prepared in Example 16 was reacted with Ag₂O to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

¹HNMR(D₂O) δ(ppm): 7.19-7.14(m,7H), 6.81-6.77(m, 3H), 3.94-3.68m,5H), 3.49-3.19(m,9H), 2.15(m,2H), 2.0-1.77(m, 11H).

Example 17

(2R,3S),(2S,3R)-3-[(2-cyclobutyl-2-hydroxyl-2-phenyl)ethoxyl]-1-(3-phenoxypropyl)-1-azabicyclo[2,2,2]octane bromide Step 1: The Same as Step 1 in [Example 13]

Step 2: Preparation of 3-[(2-cyclobutyl-2-hydroxyl-2-phenyl)ethoxyl]-1-azabicyclo[2,2,2]octane free alkali from racemic quinuclidinol

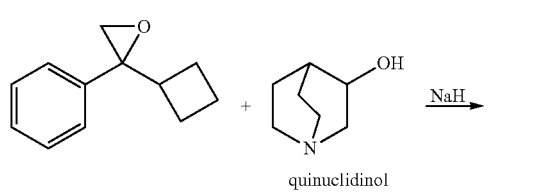
quinuclidinol

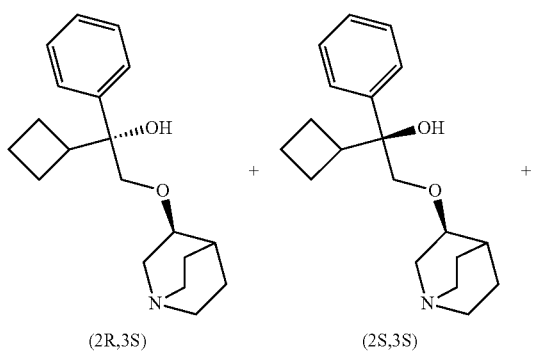
(2R,3S)    (2S,3S)

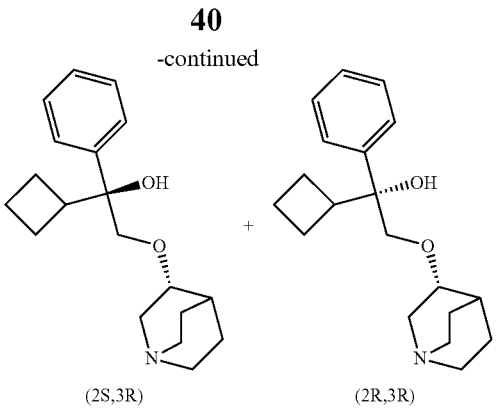
(2S,3R)    (2R,3R)

To 18.72 g (147 mmol) of commercially available racemic quinuclidinol was added 190 ml DMSO, followed by the addition of 7.59 g (190 mmol) of sodium hydride, and the mixture was reacted at 20-60° C. for 0.5-12 h, and then cooled to room temperature, and a solution of 33.06 g (190 mmol) of 1-phenyl-1-cyclobutyloxirane (self-prepared) in 45 ml DMSO was added thereto, and after the completion of dropping, the resulting mixture was heated at 20-70° C. in oil bath to react for 0.5-12 hours. Under the condition of ice bath, 120 ml of ice water was added at an inner temperature of 30° C. or less. The reaction mixture was extracted with isopropyl ether, 100 ml×3; and the ether layer was combined and washed with a saturated NaCl aqueous solution, 100 ml×3. The organic layer was dried over anhydrous sodium sulfate overnight, the drying agent was removed by filtration, and the solvent was removed under reduced pressure, to obtain 42.16 g of 3-[(2-cyclobutyl-2-hydroxyl-2-phenyl)ethoxyl]-1-azabicyclo[2,2,2]octane free alkali as a red oily matter, with the yield of 95.28%. The obtained product was (2R,3S),(2R,3R),(2S,3R),(2S,3S)-3-[(2-cyclobutyl-2-hydroxyl-2-phenyl)ethoxyl]-1-azabicyclo[2,2,2]octane free alkali.

Step 3: Purification of 3-[(2-cyclobutyl-2-hydroxyl-2-phenyl)ethoxyl]-1-azabicyclo[2,2,2]octane free alkali by Column Chromatography and Related Purification Treatment The sample from the above step 2 was separated on silica gel column, using ammoniated dichloromethane or trichloromethane and methanol as mobile phase and a TLC plate to monitor the purity of the sample. Under the above elution system, a sample of a mixture of four configurations of (2R,3S),(2R,3R),(2S,3R),(2S,3S) of 3-[(2-cyclobutyl-2-hydroxyl-2-phenyl) ethoxyl]-1-azabicyclo[2,2,2]octane free alkali could be purified into two kinds of racemic free alkali, (2R,3S),(2S,3R) and (2R,3R),(2S,3S), depending on the elution sequence, thereby obtaining the firstly eluted fraction of 17.44 g of (2R,3S),(2S,3R) racemic configuration of 3-[(2-cyclobutyl-2-hydroxyl-2-phenyl)ethoxyl]-1-azabicyclo[2,2,2]octane free alkali with the yield of 82.72%, and the secondly eluted fraction of 16.73 g of (2R,3R),(2S,3S) configuration of 3-[(2-cyclobutyl-2-hydroxyl-2-phenyl) ethoxyl]-1-azabicyclo[2,2,2]octane free alkali with the yield of 79.36%.

Step 4: The Same as Step 4 in [Example 1]

Step 5: (2R,3S),(2S,3R)-3-[(2-cyclobutyl-2-hydroxyl-2-phenyl)ethoxyl]-1-(3-phenoxypropyl)-1-azabicyclo[2,2,2]octane bromide

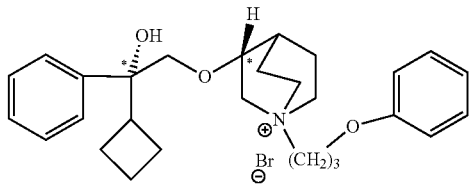

+

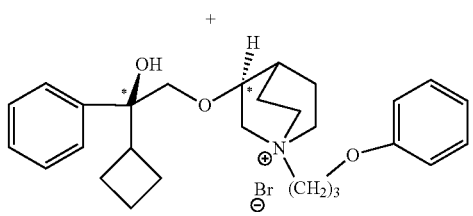

2.739 g (9.1 mmol) of (2R,3S),(2S,3R) configuration of the base was added into a 100 ml eggplant-shaped flask and was dissolved by adding 18 ml of chloroform to obtain a yellow transparent solution, to which was added 11.0342 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. under reduced pressure by a water pump, thereby obtaining a yellow oily matter, to which was added ethyl ether to precipitate a great quantity of solid, and the solid was collected by suction filtration to obtain 3.916 g of (2R,3S),(2S,3R) configuration of 3-[(2-cyclobutyl-2-hydroxyl-2-phenyl)ethoxyl]-1-(3-phenoxypropyl)-1-azabicyclo[2,2,2]octane bromide as an off-white solid, with the yield of 83.38%.

The compound prepared in Example 17 was reacted with Ag$_2$O to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D$_2$O) δ(ppm): 7.19-7.15(m,7H), 6.82-6.77(m, 3H), 3.94-3.68m 5H), 3.49-3.19(m,9H), 2.15(m,2H), 2.0-1.79 (m, 11H).

Example 18

(2R,3R),(2S,3S)-3-[(2-cyclobutyl-2-hydroxyl-2-phenyl)ethoxyl]-1-(3-phenoxypropyl)-1-azabicyclo[2,2,2]octane bromide Steps 1, 2, and 3 Were the Same as Steps 1, 2, and 3 in [Example 17]

Step 4: The Same as Step 4 in Example 1

Step 5: (2R,3R),(2S,3S)-3-[(2-cyclobutyl-2-hydroxyl-2-phenyl)ethoxyl]-1-(3-phenoxypropyl)-1-azabicyclo[2,2,2]octane bromide

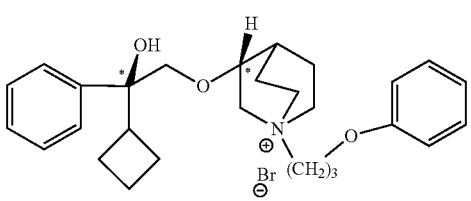

+

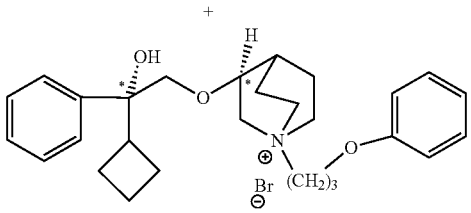

2.739 g (9.1 mmol) of (2R,3R),(2S,3S) configuration of the base was added into a 100 ml eggplant-shaped flask and was dissolved by adding 18 ml of chloroform to obtain a yellow transparent solution, to which was added 11.034 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. by rotary evaporation under reduced pressure by a water pump, thereby obtaining a yellow oily matter, to which was added ethyl ether to precipitate a great quantity of solid, and the solid was collected by suction filtration to obtain 3.918 g of (2R,3R),(2S,3S) configuration of 3-[(2-cyclobutyl-2-hydroxyl-2-phenyl)ethoxyl]-1-(3-phenoxypropyl)-1-azabicyclo[2,2,2]octane bromide as an off-white solid, with the yield of 83.42%.

The pure optical isomers of four configurations of (2R,3S),(2R,3R),(2S,3R),(2S,3S) of 3-[(2-cyclobutyl-2-hydroxyl-2-phenyl)ethoxyl]-1-azabicyclo[2,2,2]octane free alkali could be obtained from Examples 13 and 15, and mixtures of (2R,3S),(2R,3R),(2S,3R),(2S,3S) configurations of 3-[(2-cyclobutyl-2-hydroxyl-2-phenyl)ethoxyl]-1-(3-phenoxypropyl)-1-azabicyclo[2,2,2]octane bromide in different ratios were obtained by mixing these isomers in any amount and any ratio followed by quaternization by adding 3-bromopropoxy benzene.

The compound prepared in Example 18 was reacted with Ag$_2$O to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D$_2$O) δ(ppm): 7.19-7.15(m,7H), 6.82-6.77(m, 3H), 3.94-3.68m,5H), 3.49-3.19(m,9H), 2.15(m,2H), 2.0-1.79 (m, 11H).

Example 19

(2R,3S)-3-[(2-cyclopropyl-2-hydroxyl-2-phenyl) ethoxyl]-1-(3-phenoxy propyl)-1-azabicyclo[2,2,2] octane bromide Step 1: Preparation of 1-phenyl-1-cyclopropyloxirane

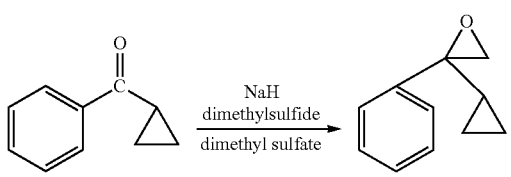 [SMILES: O=C(c1ccccc1)C1CC1 ; c1ccc(C2(C3CC3)CO2)cc1]

Commercially available cyclopropyl phenyl ketone as a starting material was reacted to obtain 1-phenyl-1-cyclopropyloxirane according to literature[1].

1880 ml of acetonitrile was added into a 3 L three-necked flask, followed by the addition of dimethyl sulfide and dimethyl sulfate, with a mild heat release, and the resulting mixture was stirred at room temperature for 1.5 h and then left it overnight. NaH (60%) was added portionwise into the reaction solution with stirring over 30-40 min, with gas being generated (pay attention to having the flask externally connected to an allihn condenser and a drying tube of anhydrous calcium chloride), and then stirred at room temperature for 1 hour, followed by the dropwise addition of 300.5 g of cyclopropyl phenyl ketone over about 10 min, and the resulting mixture was subsequently reacted in oil bath at 40-45° C. for 90 min after being stirred at room temperature for 20 min, and then cooled at room temperature and left it overnight. The reaction solution was transferred into an eggplant-shaped flask, the solvent was removed by suction using a water pump (40-42° C., −0.095 MPa), and the remaining solid was then cooled to 0-5° C. in ice bath, followed by the dropwise addition of 2630 ml of ice water (with the inner temperature being controlled at 0-5° C.) over about 1 hour, and the reaction solution was extracted with isopropyl ether (650 ml×3), the ether layer was combined and washed with water until it is neutral (with the pH of water washings being 7.0), and the ether layer was dried over anhydrous sodium sulfate overnight. The drying agent was removed by filtration, the solvent was removed under reduced pressure by suction using a water pump (40-42° C., −0.095 MPa), and 275.8 g of fraction at 111-124° C./3 mmHg was further collected under reduced pressure by using an oil pump, with the yield of 83.75%.

$^1$HNMR(CDCl$_3$) δ(ppm): 7.19 (m,5H),2.91-2.66(m,2H), 0.91(m,1H), 0.31-0.07(m,4H).

Step 2: Preparation of 3-[(2-cyclopropyl-2-hydroxyl-2-phenyl)ethoxyl]-1-azabicyclo[2,2,2]octane free alkali from S-3-quinuclidinol

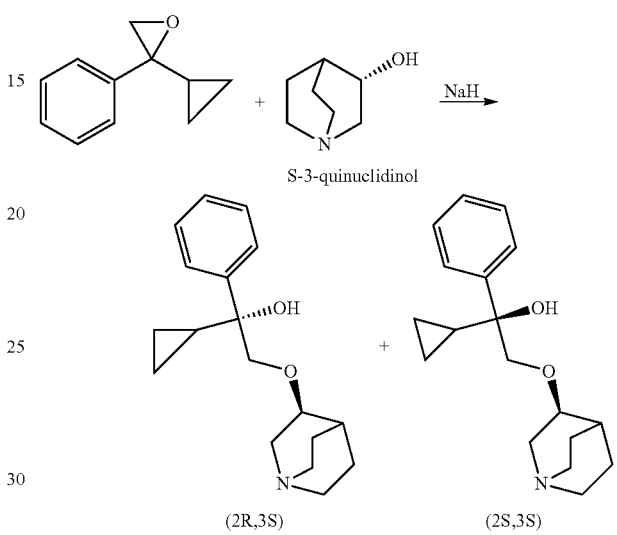

To 18.72 g (147 mmol) of commercially available S-3-quinuclidinol was added 190 ml DMSO, followed by the addition of 7.59 g (190 mmol) of sodium hydride, and the mixture was reacted at 20-60° C. for 0.5-12 h, and then cooled to room temperature, and a solution of 30.35 g (190 mmol) of 1-phenyl-1-cyclopropyloxirane (self-prepared) in 45 ml DMSO was added thereto, and after the completion of dropping, the resulting mixture was heated at 20-70° C. in oil bath to react for 0.5-12 hours. Under the condition of ice bath, 120 ml of ice water was added at an inner temperature of 30° C. or less. The reaction mixture was extracted with isopropyl ether, 100 ml×3; and the ether layer was combined and washed with a saturated NaCl aqueous solution, 100 ml×3. The organic layer was dried over anhydrous sodium sulfate overnight, the drying agent was removed by filtration, and the solvent was removed under reduced pressure to obtain 41.40 g of 3-[(2-cyclopropyl-2-hydroxyl-2-phenyl) ethoxyl]-1-azabicyclo[2,2,2]octane free alkali as a red oily matter, with the yield of 98.13%. The obtained product was (2R,3S),(2S,3S) configuration of 3-[(2-cyclopropyl-2-hydroxyl-2-phenyl)ethoxyl]-1-azabicyclo[2,2,2]octane free alkali.

Step 3: Purification of 3-[(2-cyclopropyl-2-hydroxyl-2-phenyl)ethoxyl]-1-azabicyclo[2,2,2]octane free alkali by Column Chromatography and Related Purification Treatment The sample from the above step 2 was separated on silica gel column, using ammoniated dichloromethane or trichloromethane and methanol as mobile phase and a TLC plate to monitor the purity of the sample. Under the above elution system, a sample of a mixture of both (2R,3S) and (2S,3S) configurations of 3-[(2-cyclopropyl-2-hydroxyl-2-phenyl)

ethoxyl]-1-azabicyclo[2,2,2]octane free alkali could be purified into two kinds of free alkali, (2R,3S) and (2S,3S), depending on the elution sequence, thereby obtaining 16.44 g of (2R,3 S)-3-[(2-cyclopropyl-2-hydroxyl-2-phenyl) ethoxyl]-1-azabicyclo[2,2,2]octane free alkali with the yield of 79.43%, and 16.49 g of (2S,3S)-3-[(2-cyclopropyl-2-hydroxyl-2-phenyl) ethoxyl]-1-azabicyclo[2,2,2]octane free alkali with the yield of 79.68%.

Step 4: The Same as Step 4 in [Example 1]

Step 5: (2R,3S)-3-[(2-cyclopropyl-2-hydroxyl-2-phenyl)ethoxyl]-1-(3-phenoxypropyl)-1-azabicyclo[2,2,2]octane bromide

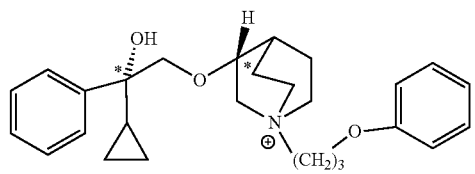

2.612 g (9.1 mmol) of (2R,3S) configuration of the base was added into a 100 ml eggplant-shaped flask and was dissolved by adding 18 ml of chloroform to obtain a yellow transparent solution, to which was added 11.034 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. by rotary evaporation under reduced pressure by a water pump, thereby obtaining a yellow oily matter, to which was added ethyl ether to precipitate a great quantity of solid, and the solid was collected by suction filtration to obtain 3.725 g of (2R,3S)-3-[(2-cyclopropyl-2-hydroxyl-2-phenyl)ethoxyl]-1-(3-phenoxypropyl)-1-azabicyclo[2,2,2] octane bromide as an off-white solid, with the yield of 81.55%.

The compound prepared in Example 19 was reacted with Ag$_2$O to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D$_2$O) δ(ppm): 7.19-7.15(m,7H), 6.82-6.77(m, 3H), 3.94-3.68m,4H), 3.49-3.19(m,9H), 2.15(m,2H), 1.82-1.57(m,5H),0.67-0.06 (m, 5H).

Example 20

(2S,3S)-3-[(2-cyclopropyl-2-hydroxyl-2-phenyl) ethoxyl]-1-(3-phenoxypropyl)-1-azabicyclo[2,2,2] octane bromide Steps 1, 2, and 3 Were the Same as Steps 1, 2, and 3 in [Example 19]

Step 4 was the Same as Step 4 in [Example 1]

Step 5: (2S,3S)-3-[(2-cyclopropyl-2-hydroxyl-2-phenyl)ethoxyl]-1-(3-phenoxypropyl)-1-azabicyclo[2,2,2]octane bromide

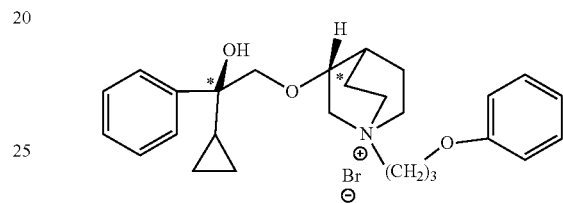

2.612 g (9.1 mmol) of (2S,3S) configuration of the base was added into a 100 ml eggplant-shaped flask and was dissolved by adding 18 ml of chloroform to obtain a yellow transparent solution, to which was added 11.034 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. by rotary evaporation under reduced pressure by a water pump, thereby obtaining a yellow oily matter, to which was added ethyl ether to precipitate a great quantity of solid, and the solid was collected by suction filtration to obtain 3.776 g of (2S,3S) configuration of 3-[(2-cyclopropyl-2-hydroxyl-2-phenyl)ethoxyl]-1-(3-phenoxypropyl)-1-azabicyclo[2,2,2]octan e bromide as an off-white solid, with the yield of 82.66%.

The compound prepared in Example 20 was reacted with Ag$_2$O to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D$_2$O) δ(ppm): 7.19-7.15(m,7H), 6.81-6.77(m, 3H), 3.94-3.68m,4H), 3.49-3.19(m,9H), 2.15(m,2H), 1.82-1.57(m,5H),0.66-0.06 (m, 5H).

Example 21

(2S,3R)-3-[(2-cyclopropyl-2-hydroxyl-2-phenyl)ethoxyl]-1-(3-phenoxypropyl)-1-azabicyclo[2,2,2]octane bromide Step 1 was the Same as Step 1 in [Example 19]

Step 2: Preparation of 3-[(2-cyclopropyl-2-hydroxyl-2-phenyl)ethoxyl]-1-azabicyclo[2,2,2]octane free alkali from R-3-quinuclidinol

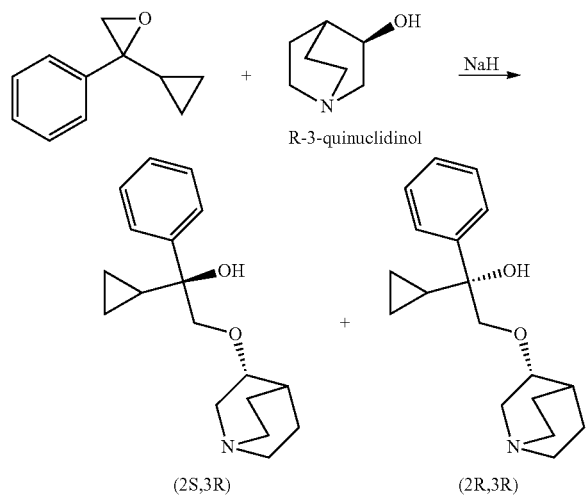

To 18.721 g (147 mmol) of commercially available R-3-quinuclidinol was added 190 ml DMSO, followed by the addition of 7.591 g (190 mmol) of sodium hydride, and the mixture was reacted at 20-60° C. for 0.5-12 h, and then cooled to room temperature, and a solution of 30.36 g (190 mmol) of 1-phenyl-1-cyclopropyloxirane (self-prepared) in 45 ml DMSO was added thereto, and after the completion of dropping, the resulting mixture was heated at 20-70° C. in oil bath to react for 0.5-12 hours. Under the condition of ice bath, 120 ml of ice water was added at an inner temperature of 30° C. or less. The reaction mixture was extracted with isopropyl ether, 100 ml×3; and the ether layer was combined and washed with a saturated NaCl aqueous solution, 100 ml×3. The organic layer was dried over anhydrous sodium sulfate overnight, the drying agent was removed by filtration, and the solvent was removed by rotary evaporation to obtain 40.99 g of 3-[(2-cyclopropyl-2-hydroxyl-2-phenyl)ethoxyl]-1-azabicyclo[2,2,2]octane free alkali as a red oily matter, with the yield of 97.15%. The obtained product was (2R,3R),(2S,3R) configuration of 3-[(2-cyclopropyl-2-hydroxyl-2-phenyl)ethoxyl]-1-azabicyclo[2,2,2]octane free alkali.

Step 3: Purification of 3-[(2-cyclopropyl-2-hydroxyl-2-phenyl)ethoxyl]-1-azabicyclo[2,2,2]octane free alkali by Column Chromatography and Related Purification Treatment The sample from the above step 2 was separated on silica gel column, using ammoniated dichloromethane or trichloromethane and methanol as mobile phase and a TLC plate to monitor the purity of the sample. Under the above elution system, a sample of a mixture of both (2R,3R) and (2S,3R) configurations of 3-[(2-cyclopropyl-2-hydroxyl-2-phenyl)ethoxyl]-1-azabicyclo[2,2,2]octane free alkali could be purified into two kinds of free alkali, (2R,3R) and (2S,3R), depending on the elution sequence, thereby obtaining 16.45 g of (2R,3R)-3-[(2-cyclopropyl-2-hydroxyl-2-phenyl)ethoxyl]-1-azabicyclo[2,2,2]octane free alkali with the yield of 80.25%, and 16.26 g of (2S,3R) configuration of 3-[(2-cyclopropyl-2-hydroxyl-2-phenyl)ethoxyl]-1-azabicyclo[2,2,2]octane free alkali with the yield of 79.34%.

Step 4: The Same as Step 4 in [Example 1]

Step 5: (2S,3R)-3-[(2-cyclopropyl-2-hydroxyl-2-phenyl)ethoxyl]-1-(3-phenoxypropyl)-1-azabicyclo[2,2,2]octane bromide

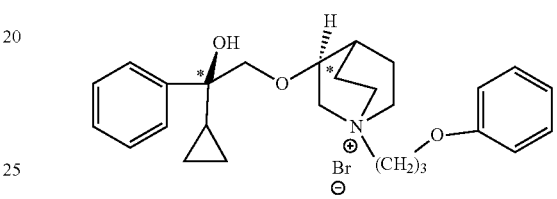

2.612 g (9.1 mmol) of (2S,3R) configuration of the base was added into a 100 ml eggplant-shaped flask and was dissolved by adding 18 ml of chloroform to obtain a yellow transparent solution, to which was added 11.0340 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. by rotary evaporation under reduced pressure by a water pump, thereby obtaining a yellow oily matter, to which was added ethyl ether to precipitate a great quantity of solid, and the solid was collected by suction filtration to obtain 3.599 g of (2S,3R)-3-[(2-cyclopropyl-2-hydroxyl-2-phenyl)ethoxyl]-1-(3-phenoxypropyl)-1-azabicyclo[2,2,2]octane bromide as an off-white solid, with the yield of 78.78%.

The compound prepared in Example 21 was reacted with $Ag_2O$ to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR($D_2O$) δ(ppm): 7.19-7.15(m,7H), 6.82-6.77(m, 3H), 3.94-3.68m,4H), 3.49-3.19(m,9H), 2.15(m,2H), 1.82-1.57(m,5H), 0.67-0.06 (m, 5H).

Example 22

(2R,3R)-3-[(2-cyclopropyl-2-hydroxyl-2-phenyl)ethoxyl]-1-(3-phenoxypropyl)-1-azabicyclo[2,2,2]octane bromide Step 1 was the Same as Step 1 in [Example 19]

Steps 2 and 3 Were the Same as Steps 2 and 3 in [Example 21]

Step 4: The Same as Step 4 in [Example 1]

Step 4: (2R,3R)-3-[(2-cyclopropyl-2-hydroxyl-2-phenyl)ethoxyl]-1-(3-phenoxypropyl)-1-azabicyclo[2,2,2]octane bromide

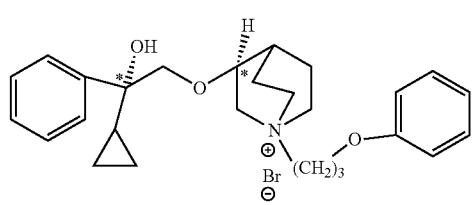

2.612 g (9.1 mmol) of (2R,3R) configuration of the base was added into a 100 ml eggplant-shaped flask and was dissolved by adding 18 ml of chloroform to obtain a yellow transparent solution, to which was added 11.034 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. by rotary evaporation under reduced pressure by a water pump, thereby obtaining a yellow oily matter, to which was added ethyl ether to precipitate a great quantity of solid, and the solid was collected by suction filtration to obtain 3.795 g of (2R,3R)-3-[(2-cyclopropyl-2-hydroxyl-2-phenyl)ethoxyl]-1-(3-phenoxypropyl)-1-azabicyclo[2,2,2]octane bromide as an off-white solid, with the yield of 83.07%.

The compound prepared in Example 22 was reacted with $Ag_2O$ to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR($D_2O$) δ(ppm): 7.19-7.15(m,7H), 6.82-6.77(m, 3H), 3.94-3.68m,4H), 3.49-3.19(m,9H), 2.15(m,2H), 1.82-1.57(m,5H), 0.67-0.06 (m, 5H).

Example 23

(2R,3S),(2S,3R)-3-[(2-cyclopropyl-2-hydroxyl-2-phenyl)ethoxyl]-1-(3-phenoxypropyl)-1-azabicyclo[2,2,2]octane bromide Step 1 was the Same as Step 1 in [Example 19]

Step 2: Preparation of 3-[(2-cyclopropyl-2-hydroxyl-2-phenyl)ethoxyl]-1-azabicyclo[2,2,2]octane free alkali from racemic quinuclidinol

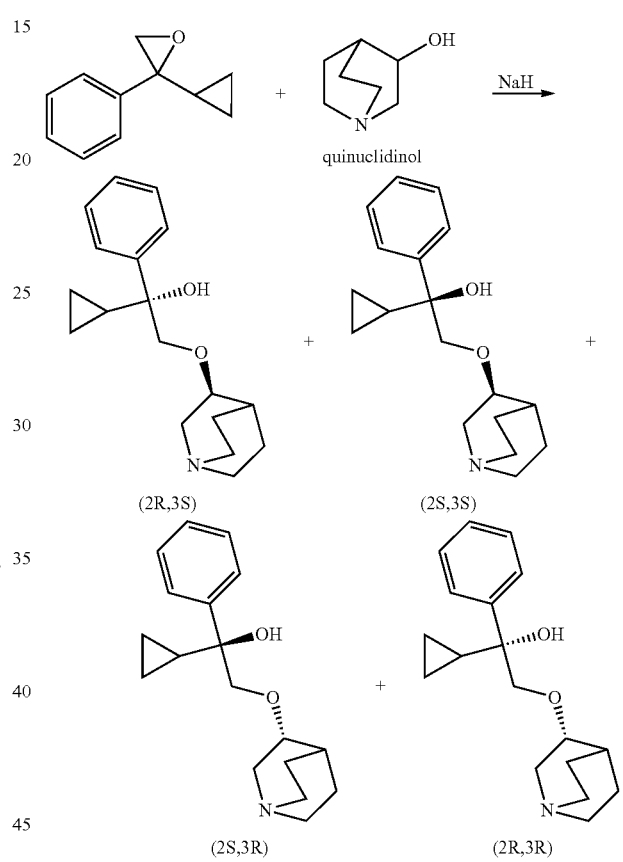

To 18.72 g (147 mmol) of commercially available racemic quinuclidinol was added 190 ml DMSO, followed by the addition of 7.59 g (190 mmol) of sodium hydride, and the mixture was reacted at 20-60° C. for 0.5-12 h, and then cooled to room temperature, and a solution of 30.4 g (190 mmol) of 1-phenyl-1-cyclopropyloxirane (self-prepared) in 45 ml DMSO was added thereto, and after the completion of dropping, the resulting mixture was heated at 20-70° C. in oil bath to react for 0.5-12 hours. Under the condition of ice bath, 120 ml of ice water was added at an inner temperature of 30° C. or less. The reaction mixture was extracted with isopropyl ether, 100 ml×3; and the ether layer was combined and washed with a saturated NaCl aqueous solution, 100 ml×3. The organic layer was dried over anhydrous sodium sulfate overnight, the drying agent was removed by filtration, and the solvent was removed by rotary evaporation, to obtain 42.02 g of 3-[(2-cyclopropyl-2-hydroxyl-2-phenyl)ethoxyl]-1-azabicyclo[2,2,2]octane free alkali as a red oily matter, with the yield of 99.6%. The obtained product was (2R,3S),(2R,3R),(2S,3R),(2S,3S) configuration of 3-[(2-cyclopropyl-2-hydroxyl-2-phenyl)ethoxyl]-1-azabicyclo[2,2,2]octane free alkali.

Step 3: Purification of 3-[(2-cyclopropyl-2-hydroxyl-2-phenyl)ethoxyl]-1-azabicyclo[2,2,2]octane free alkali by Column Chromatography and Related Purification Treatment The sample from the above step 1 was separated on silica gel column, using ammoniated dichloromethane or trichloromethane and methanol as mobile phase and a TLC plate to monitor the purity of the sample. Under the above elution system, a sample of a mixture of four configurations of (2R,3S),(2R,3R),(2S,3R),(2S,3S) of 3-[(2-cyclopropyl-2-hydroxyl-2-phenyl)ethoxyl]-1-azabicyclo[2,2,2]octane free alkali could be purified into two kinds of racemic free alkali, (2R,3S),(2S,3R) and (2R,3R),(2S,3S), depending on the elution sequence, thereby obtaining the firstly eluted fraction of 17.06 g of (2R,3S),(2S,3R) racemic configuration of 3-[(2-cyclopropyl-2-hydroxyl-2-phenyl)ethoxyl]-1-azabicyclo[2,2,2]octane free alkali with the yield of 81.22%, and the secondly eluted fraction of 16.63 g of (2R,3R),(2S,3S) configuration of 3-[(2-cyclopropyl-2-hydroxyl-2-phenyl)ethoxyl]-1-azabicyclo[2,2,2]octane free alkali with the yield of 79.13%.

Step 4: The Same as Step 4 in [Example 1]

Step 5: (2R,3S),(2S,3R) Configuration of 3-[(2-cyclopropyl-2-hydroxyl-2-phenyl)ethoxyl]-1-(3-phenoxypropyl)-1-azabicyclo[2,2,2]octane bromide

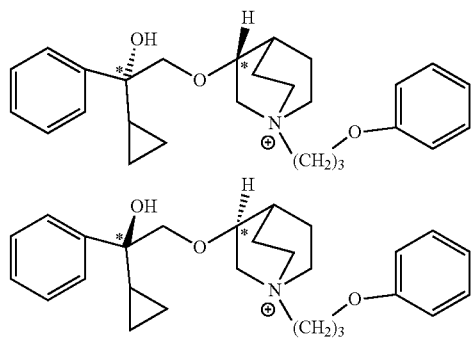

2.612 g (9.1 mmol) of (2R,3S),(2S,3R) configuration of the base was added into a 100 ml eggplant-shaped flask and was dissolved by adding 18 ml of chloroform to obtain a yellow transparent solution, to which was added 11.0342 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. by rotary evaporation under reduced pressure by a water pump, thereby obtaining a yellow oily matter, to which was added ethyl ether to precipitate a great quantity of solid, and the solid was collected by suction filtration to obtain 3.76 g of (2R,3S),(2S,3R) configuration of 3-[(2-cyclopropyl-2-hydroxyl-2-phenyl)ethoxyl]-1-(3-phenoxypropyl)-1-azabicyclo[2,2,2]octane bromide as an off-white solid, with the yield of 82.31%.

The compound prepared in Example 23 was reacted with Ag$_2$O to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D$_2$O) δ(ppm): 7.19-7.15(m,7H), 6.82-6.77(m, 3H), 3.94-3.68m,4H), 3.49-3.19(m,9H), 2.15(m,2H), 1.82-1.57(m,5H), 0.67-0.06 (m, 5H).

Example 24

(2R,3R),(2S,3S) Configuration of 3-[(2-cyclopropyl-2-hydroxyl-2-phenyl)ethoxyl]-1-(3-phenoxypropyl)-1-azabicyclo[2,2,2]octane bromide Step 1 was the Same as Step 1 in [Example 19]

Steps 2 and 3 Were the Same as Steps 2 and 3 in [Example 23]

Step 4: The Same as Step 4 in Example 1

Step 5: (2R,3R),(2S,3S) Configuration of 3-[(2-cyclopropyl-2-hydroxyl-2-phenyl)ethoxyl]-1-(3-phenoxypropyl)-1-azabicyclo[2,2,2]octane bromide

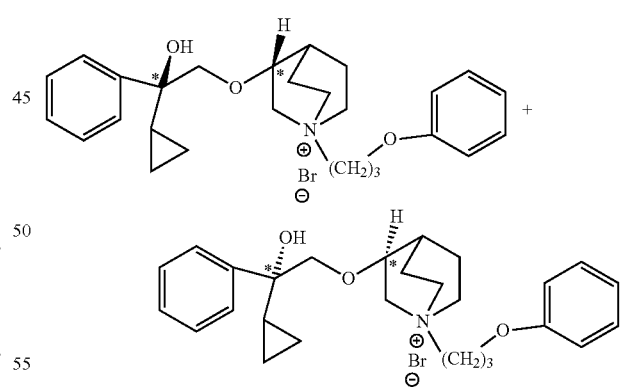

2.994 g (9.1 mmol) of (2R,3R),(2S,3S) configuration of the base was added into a 100 ml eggplant-shaped flask and was dissolved by adding 18 ml of chloroform to obtain a yellow transparent solution, to which was added 11.034 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. by rotary evaporation under reduced pressure by a water pump, thereby obtaining a yellow oily matter, to which was added ethyl ether to precipitate a great quantity of solid, and the solid was collected by suction filtration to obtain 3.54 g of (2R,3R),(2S,3S) configuration of 3-[(2-cyclopropyl-2-hydroxyl-2-phenyl)ethoxyl]-1-(3-phenoxypropyl)-1-azabicyclo[2,2,2]octan e bromide as an off-white solid, with the yield of 77.49%.

The pure optical isomers of four configurations of (2R,3S),(2R,3R),(2S,3R),(2S,3S) of 3-[(2-cyclopropyl-2-hydroxyl-2-phenyl)ethoxyl]-1-azabicyclo[2,2,2]octane free alkali could be obtained from Examples 19 and 21, and mixtures of (2R,3S),(2R,3R),(2S,3R),(2S,3S) configurations of 3-[(2-cyclopropyl-2-hydroxyl-2-phenyl)ethoxyl]-1-(3-phenoxypropyl)-1-azabicyclo[2,2,2]octane bromide in different ratios were obtained by mixing these isomers in any amount and any ratio followed by quaternization by adding 3-bromopropoxy benzene.

The compound prepared in Example 24 was reacted with Ag$_2$O to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D$_2$O) δ(ppm): 7.19-7.15(m,7H), 6.82-6.77(m, 3H), 3.94-3.68m,4H), 3.49-3.19(m,9H), 2.15(m,2H), 1.82-1.57(m,5H), 0.67-0.06 (m, 5H).

Example 25

(2S,3R)-3-[(2-cyclopentyl-2-hydroxyl-2-phenyl)ethoxyl]-1-(2-phenoxyethyl)-1-azabicyclo[2,2,2]octane bromide Step 1: The Same as Step 1 in [Example 1]

Steps 2 and 3: the Same as Steps 2 and 3 in [Example 3]

Step 4: Preparation of 2-bromoethoxyl benzene

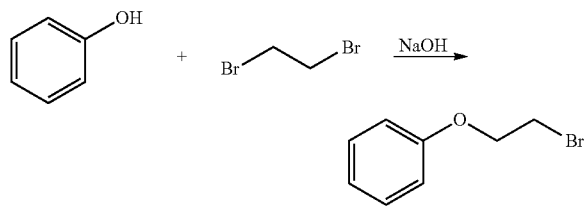

9.5 g (101 mmol) of phenol was added into a 150 ml three-necked flask, followed by the addition of 4.25 g (106 mmol) of sodium hydroxide and a solution of 47.11 g (250 mmol) of 1,2-dibromoethane in 30 ml of absolute ethanol, and the resulting mixture was then reacted under heating and refluxing in oil bath, with a white solid being precipitated, until the essentially complete reaction of phenol monitored by TLC (TLC condition: petroleum ether/ethyl acetate=5.0 ml/1.0 ml). After the reaction being completed, the solid was removed by filtration, and the solvent was removed from the filtrate at 50° C. or less by rotary evaporation under reduced pressure by a water pump, thereby obtaining an oily matter containing a white solid, to which was added petroleum ether and then left it overnight. The precipitated solid was removed by filtration, and the solvent was removed from the filtrate at 25-40° C. by rotary evaporation under reduced pressure by a water pump, thereby obtaining a yellow oily matter. The oily matter was distilled under reduced pressure, to collect a fraction at 8 mmHg, 118-122° C., thereby obtaining 11.31 g of a colorless, transparent oily matter, with the yield of 55.7% and the purity of 95.6065% detected by GC.

$^1$HNMR(CDCl$_3$) δ(ppm): 7.15-6.77(m,5H), 4.45(t,2H), 3.79(t,2H).

Step 5: (2S,3R)-3-[(2-cyclopentyl-2-hydroxyl-2-phenyl)ethoxyl]-1-(2-phenoxyethyl)-1-azabicyclo[2,2,2]octane bromide

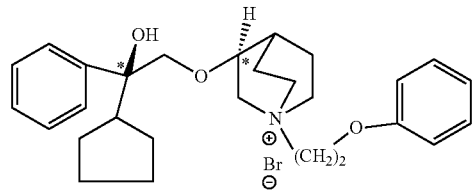

1.436 g (4.55 mmol) of (2S,3R) configuration of the base was added into a 50 ml eggplant-shaped flask and was dissolved by adding 9 ml of chloroform to obtain a yellow transparent solution, to which was added 5.65 g (28.1 mmol) of 2-bromoethoxy benzene and 25 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. by rotary evaporation under reduced pressure by a water pump, thereby obtaining a yellow oily matter, to which was added ethyl ether to precipitate a great quantity of solid, and the solid was collected by suction filtration to obtain 1.857 g of (2S,3R)-3-[(2-cyclopentyl-2-hydroxyl-2-phenyl)ethoxyl]-1-(3-phenoxyethyl)-1-azabicyclo[2,2,2]octane bromide as an off-white solid, with the yield of 79.12%.

The compound prepared in Example 25 was reacted with Ag$_2$O to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D$_2$O) δ(ppm): 7.18-6.76(m,10H), 5.86(t,2H), 4.39(t,2H), 3.98-3.71(s,2H), 3.47-3.18(m,7H), 1.92 (m,1H), 1.81-1.66 (m,5H), 1.59-1.36 (m,8H).

Example 26

(2R,3R)-3-[(2-cyclopentyl-2-hydroxyl-2-phenyl) ethoxyl]-1-(2-phenoxyethyl)-1-azabicyclo[2,2,2] octane bromide Step 1: The Same as Step 1 in [Example 1]

Steps 2 and 3 Were the Same as Steps 2 and 3 in [Example 3]

Step 4 was the Same as Step 4 in [Example 25]

Step 5: (2R,3R)-3-[(2-cyclopentyl-2-hydroxyl-2-phenyl)ethoxyl]-1-(2-phenoxyethyl)-1-azabicyclo[2,2,2]octane bromide

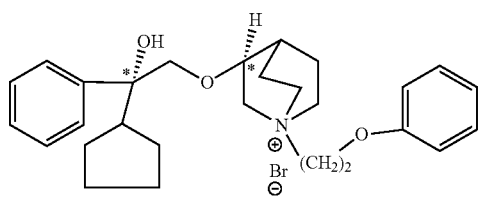

1.435 g (4.55 mmol) of (2R,3R) configuration of the base was added into a 50 ml eggplant-shaped flask and was dissolved by adding 9 ml of chloroform to obtain a yellow transparent solution, to which was added 5.65 g (28.1 mmol) of 2-bromoethoxy benzene and 25 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. by rotary evaporation under reduced pressure by a water pump, thereby obtaining a yellow oily matter, to which was added ethyl ether to precipitate a great quantity of solid, and the solid was collected by suction filtration to obtain 1.797 g of (2R,3R)-3-[(2-cyclopentyl-2-hydroxyl-2-phenyl)ethoxyl]-1-(3-phenoxyethyl)-1-azabicyclo[2,2,2]octane bromide as an off-white solid, with the yield of 76.56%.

The compound prepared in Example 26 was reacted with Ag$_2$O to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D$_2$O) δ(ppm): 7.19-6.78(m,10H),5.88(t,2H), 4.38(t 2H),3.99-3.70(s,2H), 3.47-3.17(m,7H), 1.93 (m,1H), 1.81-1.67 (m,5H),1.60-1.37 (m,8H).

Example 27

(2R,3R)-3-[(2-cyclopentyl-2-hydroxyl-2-phenyl) ethoxyl]-1-phenoxymethyl-1-azabicyclo[2,2,2]octane bromide Step 1: The Same as Step 1 in [Example 1]

Steps 2 and 3 Were the Same as Steps 2 and 3 in [Example 3]

Step 4: Preparation of bromomethoxyl benzene

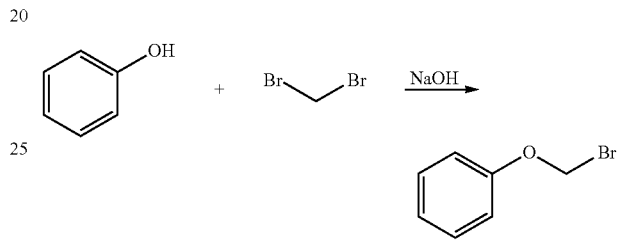

9.5 g (101 mmol) of phenol was added into a 150 ml three-necked flask, followed by the addition of 4.25 g (106 mmol) of sodium hydroxide and a solution of 43.51 g (250 mmol) of 1,2-dibromomethane in 30 ml of absolute ethanol, and the resulting mixture was then reacted under heating and refluxing in oil bath, with a white solid being precipitated, until the essentially complete reaction of phenol monitored by TLC (TLC condition: petroleum ether/ethyl acetate=5.0 ml/1.0 ml). After the reaction being completed, the solid was removed by filtration, and the solvent was removed from the filtrate at 50° C. or less by rotary evaporation under reduced pressure by a water pump, thereby obtaining an oily matter containing a white solid, to which was added petroleum ether and then left it overnight. The precipitated solid was removed by filtration, and the solvent was removed from the filtrate at 25-40° C. by rotary evaporation under reduced pressure by a water pump, thereby obtaining a yellow oily matter.

The oily matter was distilled under reduced pressure, to collect a fraction at 8 mmHg, 116-120° C., thereby obtaining 10.75 g of a colorless, transparent oily matter, with the yield of 56.9% and the purity of 95.6065% detected by GC.

$^1$HNMR(CDCl$_3$) δ(ppm): 7.16-6.76(m,5H),5.95(s,2H)

Step 4: (2R,3R)-3-[(2-cyclopentyl-2-hydroxyl-2-phenyl)ethoxyl]-1-phenoxymethyl-1-azabicyclo[2,2,2]octane bromide

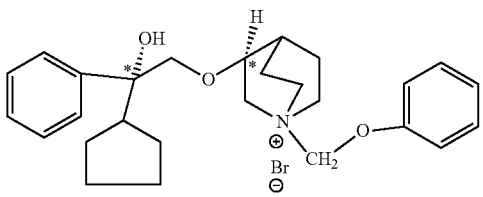

2.871 g (9.1 mmol) of (2R,3R) configuration of the base was added into a 100 ml eggplant-shaped flask and was dissolved by adding 18 ml of chloroform to obtain a yellow transparent solution, to which was added 10.29 g (55 mmol) of bromomethoxy benzene and 25 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. by rotary evaporation under reduced pressure by a water pump, thereby obtaining a yellow oily matter, to which was added ethyl ether to precipitate a great quantity of solid, and the solid was collected by suction filtration to obtain 3.751 g of (2R,3R)-3-[(2-cyclopentyl-2-hydroxyl-2-phenyl)ethoxyl]-1-(phenoxymethyl)-1-azabicyclo[2,2,2]octane bromide as an off-white solid, with the yield of 80.2%.

The compound prepared in Example 27 was reacted with Ag$_2$O to remove bromine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D$_2$O) δ(ppm): 7.21-6.76(m,10H),5.89(s,2H), 3.97-3.73(s,2H), 3.48-3.18(m,7H), 1.95 (m,1H), 1.80-1.58 (m,5H), 1.61-1.38 (m,8H).

Example 28

(2R,3R)-3-[(2-cyclopentyl-2-hydroxyl-2-phenyl)ethoxyl]-1-phenoxymethoxymethyl-1-azabicyclo[2,2,2]octane chloride Step 1 was the Same as Step 1 in [Example 1]

Steps 2 and 3 Were the Same as Steps 2 and 3 in [Example 3]

Step 4: Preparation of phenyl chloromethoxylmethyl ether

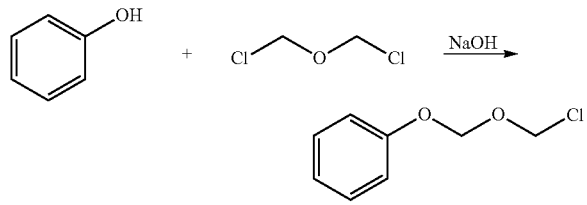

9.5 g (101 mmol) of phenol was added into a 150 ml three-necked flask, followed by the addition of 4.25 g (106 mmol) of sodium hydroxide and a solution of 28.75 g (250 mmol) of 1,3-dichloromethyl ether in 30 ml of absolute ethanol, and the resulting mixture was then reacted under heating and refluxing in oil bath, with a white solid being precipitated, until the essentially complete reaction of phenol monitored by TLC (TLC condition: petroleum ether/ethyl acetate=5.0 ml/1.0 ml). After the reaction being completed, the solid was removed by filtration, and the solvent was removed from the filtrate at 50° C. or less by rotary evaporation under reduced pressure by a water pump, thereby obtaining an oily matter containing a white solid, to which was added petroleum ether and then left it overnight. The precipitated solid was removed by filtration, and the solvent was removed from the filtrate at 25-40° C. by rotary evaporation under reduced pressure by a water pump, thereby obtaining a yellow oily matter.

The oily matter was distilled under reduced pressure, to collect a fraction at 8 mmHg, 106-119° C., thereby obtaining 8.38 g of a colorless, transparent oily matter, with the yield of 48.1% and the purity of 97.62% detected by GC.

$^1$HNMR(CDCl$_3$) δ(ppm): 7.19-6.79(m,5H), 6.01(s,2H), 5.47 (s,2H).

Step 5(2R,3R)-3-[(2-cyclopentyl-2-hydroxyl-2-phenyl)ethoxyl]-1-phenoxymethoxymethyl-1-azabicyclo[2,2,2]octane chloride

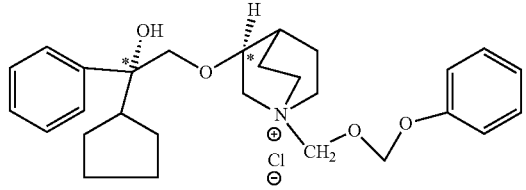

2.871 g (9.1 mmol) of (2R,3R) configuration of the base was added into a 100 ml eggplant-shaped flask and was dissolved by adding 18 ml of chloroform to obtain a yellow transparent solution, to which was added 9.49 g (55 mmol) of phenyl chloromethoxylmethyl ether and 25 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d).

After the reaction being completed, the solvent was removed from the reaction solution at 25-40° C. by rotary evaporation under reduced pressure by a water pump, thereby obtaining a yellow oily matter, to which was added ethyl ether to precipitate a great quantity of solid, and the solid was collected by suction filtration to obtain 3.13 g of (2R,3R)-3-[(2-cyclopentyl-2-hydroxyl-2-phenyl)ethoxyl]-1-phenoxymethoxymethyl)-1-azabicyclo[2,2,2]octane chloride as an off-white solid, with the yield of 69.2%.

The compound prepared in Example 28 was reacted with Ag$_2$O to remove chlorine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D$_2$O) δ(ppm): 7.19-6.77(m,10H), 6.02(s,2H), 5.32(s,2H), 3.98-3.68(s,2H), 3.49-3.19(m,7H), 1.96 (m,1H), 1.82-1.57 (m,5H), 1.60-1.36 (m,8H).

Example 29

(2R,3R)-3-[(2-cyclopentyl-2-hydroxyl-2-naphthyl) ethoxyl]-1-(3-phenoxypropyl)-1-azabicyclo[2,2,2] octane bromide Step 1: Preparation of 230 g 1-naphthyl-1-cyclopentyloxirane According to the Method in Literature[2]

Step 2: Preparation of 3-[(2-cyclopentyl-2-hydroxyl-2-naphthyl)ethoxyl]-1-azabicyclo[2,2,2]octane free alkali from R-3-quinuclidinol

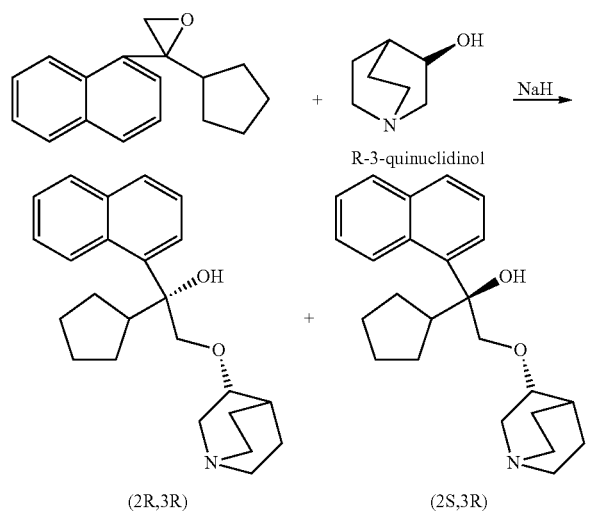

To 18.72 g (147 mmol) of commercially available R-3-quinuclidinol was added 190 ml DMSO, followed by the addition of 7.59 g (190 mmol) of sodium hydride, and the mixture was reacted at 20-60° C. for 0.5-12 h, and then cooled to room temperature, and a solution of 45.15 g (190 mmol) of 1-naphthyl-1-cyclopentyloxirane (self-prepared) in 45 ml DMSO was added thereto, and after the completion of dropping, the resulting mixture was heated at 20-70° C. in oil bath to react for 0.5-12 hours. Under the condition of ice bath, 120 ml of ice water was added at an inner temperature of 30° C. or less. The reaction mixture was extracted with isopropyl ether, 100 ml×3; and the ether layer was combined and washed with a saturated NaCl aqueous solution, 100 ml×3. The organic layer was dried over anhydrous sodium sulfate overnight, the drying agent was removed by filtration, and the solvent was removed under reduced pressure to obtain 51.71 g of 3-[(2-cyclopentyl-2-hydroxyl-2-naphthyl)ethoxyl]-1-azabicyclo[2,2,2]octane free alkali as a red oily matter, with the yield of 96.38%. The obtained product was (2R,3R),(2S,3R) configuration of 3-[(2-cyclopentyl-2-hydroxyl-2-naphthyl)ethoxyl]-1-azabicyclo[2,2,2]octane free alkali.

Step 3: Purification of 3-[(2-cyclopentyl-2-hydroxyl-2-naphthyl)ethoxyl]-1-azabicyclo[2,2,2]octane free alkali by Column Chromatography and Related Purification Treatment The sample from the above step 2 was separated on silica gel column, using ammoniated dichloromethane or trichloromethane and methanol as mobile phase and a TLC plate to monitor the purity of the sample. Under the above elution system, a sample of a mixture of both (2R,3R) and (2S,3R) configurations of 3-[(2-cyclopentyl-2-hydroxyl-2-naphthyl)ethoxyl]-1-azabicyclo[2,2,2]octane free alkali could be purified into two kinds of free alkali, (2R,3R) and (2S,3R), depending on the elution sequence, thereby obtaining 22.36 g of (2R,3R) configuration of 3-[(2-cyclopentyl-2-hydroxyl-2-naphthyl)ethoxyl]-1-azabicyclo[2,2,2]octane free alkali with the yield of 86.5%, and 20.05 g of (2S,3R) configuration of 3-[(2-cyclopentyl-2-hydroxyl-2-naphthyl)ethoxyl]-1-azabicyclo[2,2,2]octane free alkali with the yield of 77.55%.

Step 4: The Same as Step 4 in [Example 1]

Step 5: (2R,3R)-3-[(2-cyclopentyl-2-hydroxyl-2-naphthyl)ethoxyl]-1-(3-phenoxypropyl)-1-azabicyclo[2,2,2]octane bromide

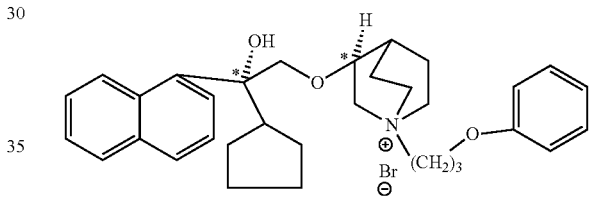

3.322 g (9.1 mmol) of (2R,3R) configuration of the base was added into a 100 ml eggplant-shaped flask and was dissolved by adding 18 ml of chloroform to obtain a yellow transparent solution, to which was added 11.033 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. by rotary evaporation under reduced pressure by a water pump, thereby obtaining a yellow oily matter, to which was added ethyl ether to precipitate a great quantity of solid, and the solid was collected by suction filtration to obtain 4.238 g of (2R,3R)-3-[(2-cyclopentyl-2-hydroxyl-2-naphthyl)ethoxyl]-1-(3-phenoxypropyl)-1-azabicyclo[2,2,2]octane bromide as an off-white solid, with the yield of 80.3%.

The compound prepared in Example 29 was reacted with Ag$_2$O to remove chlorine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D$_2$O)(ppm): δ7.21-6.66(m,12H), δ4.17-3.65(m, 5H), δ3.44-3.13(m,8H), δ2.15(m,2H), 2.00(m,1H), δ1.84-1.42(m,13H).

Example 30

(2R,3R)-3-[(2-cyclopentyl-2-hydroxyl-2-o-chlorophenyl)ethoxyl]-1-(3-phenoxypropyl)-1-azabicyclo[2,2,2]octane bromide Step 1: 1-o-chlorophenyl-1-cyclopentyloxirane

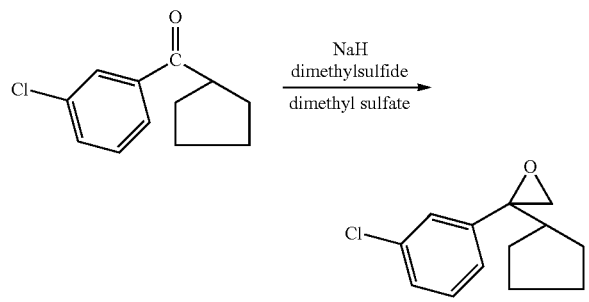

Commercially available cyclopentyl o-phenyl ketone as a starting material was reacted to obtain 1-o-chlorophenyl-1-cyclopentyloxirane according to literature$^{(1)}$.

1880 ml of acetonitrile was added into a 3 L three-necked flask, followed by the addition of dimethyl sulfide and dimethyl sulfate, with a mild heat release, and the resulting mixture was stirred at room temperature for 1.5 h and then left it overnight. NaH (60%) was added portionwise into the reaction solution with stirring over 30-40 min, with gas being generated (pay attention to having the flask externally connected to an allihn condenser and a drying tube of anhydrous calcium chloride), and then stirred at room temperature for 1 hour, followed by the dropwise addition of 355 g of cyclopentyl o-chlorophenyl ketone over about 10 min, and the resulting mixture was subsequently reacted in oil bath at 40-45° C. for 90 min after being stirred at room temperature for 20 min, and then cooled at room temperature and left it overnight. The reaction solution was transferred into an eggplant-shaped flask, the solvent was removed by suction using a water pump (40-42° C., −0.095 MPa), and the remaining solid was then cooled to 0-5° C. in ice bath, followed by the dropwise addition of 2630 ml of ice water (with the inner temperature being controlled at 0-5° C.) over about 1 hour, and the reaction solution was extracted with isopropyl ether (650 ml×3), the ether layer was combined and washed with water until it is neutral (with the pH of water washings being 7.0), and the ether layer was dried over anhydrous sodium sulfate overnight. The drying agent was removed by filtration, the solvent was removed under reduced pressure by suction using a water pump (40-42° C., −0.095 MPa), and 315.8 g of fraction at 119-132° C./3 mmHg was further collected under reduced pressure by using an oil pump, with the yield of 83.36%.

$^1$HNMR(CDCl$_3$) δ(ppm): 7.19-7.07(m,4H), 2.92-2.64(m, 1H), 2.21(s,2H), 1.61-1.37(m,8H).

Step 2: Preparation of 3-[(2-cyclopentyl-2-hydroxyl-2-o-chlorophenyl)ethoxyl]-1-azabicyclo[2,2,2]octane free alkali from R-3-quinuclidinol

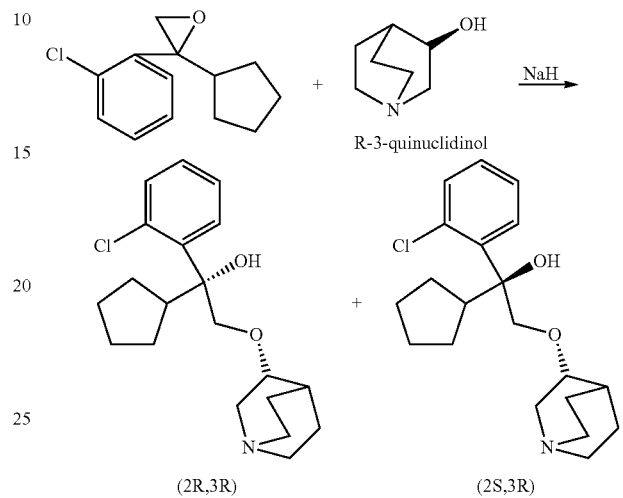

To 18.72 g (147 mmol) of commercially available R-3-quinuclidinol was added 190 ml DMSO, followed by the addition of 7.59 g (190 mmol) of sodium hydride, and the mixture was reacted at 20-60° C. for 0.5-12 h, and then cooled to room temperature, and a solution of 42.317 g (190 mmol) of 1-o-chlorophenyl-1-cyclopentyloxirane (self-prepared) in 45 ml DMSO was added thereto, and after the completion of dropping, the resulting mixture was heated at 20-70° C. in oil bath to react for 0.5-12 hours. Under the condition of ice bath, 120 ml of ice water was added at an inner temperature of 30° C. or less. The reaction mixture was extracted with isopropyl ether, 100 ml×3; and the ether layer was combined and washed with a saturated NaCl aqueous solution, 100 ml×3. The organic layer was dried over anhydrous sodium sulfate overnight, the drying agent was removed by filtration, and the solvent was removed under reduced pressure to obtain 49.48 g of 3-[(2-cyclopentyl-2-hydroxyl-2-o-chlorophenyl)ethoxyl]-1-azabicyclo[2,2,2]octane free alkali as a red oily matter, with the yield of 96.31%. The obtained product was (2R,3R),(2S,3R)-3-[(2-cyclopentyl-2-hydroxyl-2-o-chlorophenyl)ethoxyl]-1-azabicyclo[2,2,2]octane free alkali.

Step 3: Purification of 3-[(2-cyclopentyl-2-hydroxyl-2-o-chlorophenyl)ethoxyl]-1-azabicyclo[2,2,2]octane free alkali by Column Chromatography and Related Purification Treatment The sample from the above step 1 was separated on silica gel column, using ammoniated dichloromethane or trichloromethane and methanol as mobile phase and a TLC plate to monitor the purity of the sample. Under the above elution system, a sample of a mixture of both (2R,3R) and (2S,3R) configurations of 3-[(2-cyclopentyl-2-hydroxyl-2-o-chlorophenyl)ethoxyl]-1-azabicyclo[2,2,2]octane free alkali could be purified into two kinds of free alkali, (2R,3R) and (2S,3R), depending on the elution sequence, thereby obtaining 21.03 g of (2R,3R)-3-[(2-cyclopentyl-2-hydroxyl-2-o- chlorophenyl)ethoxyl]-1-azabicyclo[2,2,2]octane free alkali with the yield of 85.0%, and 21.15 g of (2S,3R)-3-[(2-cyclopentyl-2-hydroxyl-2-o-chlorophenyl)ethoxyl]-1-azabicyclo[2,2,2]octane free alkali with the yield of 85.485%.

Step 4: The Same as Step 4 in [Example 1]

Step 5: (2R,3R)-3-[(2-cyclopentyl-2-hydroxyl-2-o-chlorophenyl)ethoxyl]-1-(3-phenoxypropyl)-1-azabicyclo[2,2,2]octane bromide

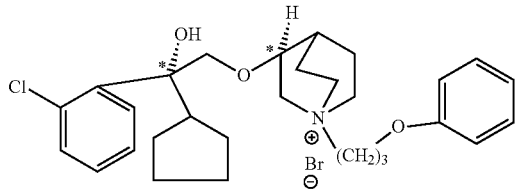

3.18 g (9.1 mmol) of (2R,3R) configuration of the base was added into a 100 ml eggplant-shaped flask and was dissolved by adding 18 ml of chloroform to obtain a yellow transparent solution, to which was added 11.033 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. by rotary evaporation under reduced pressure by a water pump, thereby obtaining a yellow oily matter, to which was added ethyl ether to precipitate a great quantity of solid, and the solid was collected by suction filtration to obtain 4.25 g of (2R,3R)-3-[(2-cyclopentyl-2-hydroxyl-2-o-chlorophenyl)ethoxyl]-1-(3-phenoxypropyl)-1-azabicyclo[2,2,2]octane bromide as an off-white solid, with the yield of 82.73%.

The compound prepared in Example 30 was reacted with $Ag_2O$ to remove chlorine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR(D2O)(ppm): δ7.33-6.65(m,9H), δ4.16-3.63(m, 5H), δ3.45-3.12(m,8H), δ2.13(m,2H), 2.02(m,1H), δ1.83-1.43(m,13H).

Example 31

(2R,3R)-3-[(2-cyclopentyl-2-hydroxyl-2-(3-pyridyl))ethoxyl]-1-(3-phenoxypropyl)-1-azabicyclo[2,2,2]octane bromide Step 1: Preparation of cyclopentyl 3-pyridyl ketone

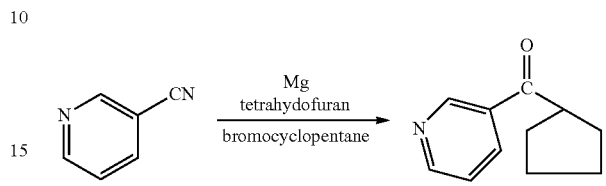

102.06 g of magnesium chips were placed into a 5 L three-necked flask externally connected to an allihn condenser and a drying tube of anhydrous calcium chloride and a thermometer, 1600 ml of THF and 1.06 g of iodine were added thereto and stirred, and 78.28 g of bromocyclopentane was then added dropwise to the reaction solution. At about 5 min after the reaction was fully initiated, the reaction solution was gradually changed from being light reddish brown to be colourless, with the inner temperature automatically increasing to 63-65° C. 547.93 g of additional bromocyclopentane was then added dropwise over about 35 min, with its refluxing temperature gradually increasing to 75-77° C. The reaction mixture was reacted under refluxing in oil bath for 2 hours.

412.74 g of 3-pyridylcarbonitrile diluted in 1600 ml THF was added dropwise into the above reaction solution, and the resulting mixture was then reacted under refluxing in oil bath for 4 hours. The inner temperature was lowered to 5-10° C., 96 ml of ice water was added dropwise, and then stirred for 20 min, followed by the addition of HCl to adjust pH=2.0, and the resulting mixture was heated to reflux for 3 hours, the organic layer was then separated, and once cooled, the aqueous phase was extracted with isopropyl ether (200 ml×3). The organic layer was combined and washed with 1% $Na_2CO_3$ (500×3) and water (500×3) successively, and the organic layer was dried over anhydrous sodium sulfate overnight. The drying agent was removed by filtration, the solvent was removed by evaporation (42° C., −0.095 MPa), and 332.26 g of oily matter was collected at 122-130° C./6-7 mmHg further by distillation under reduced pressure by using an oil pump.

$^1$HNMR(CDCl$_3$) δ(ppm): 9.31-7.70(m,4H), 2.36(m,1H), 1.63-1.47(m,8H).

Step 2: Preparation of 1-(3-pyridyl)-1-cyclopentyloxirane

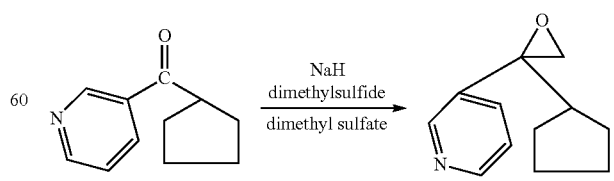

Cyclopentyl 3-pyridylphenyl ketone as a starting material was reacted to obtain 1-(3-pyridyl)-1-cyclopentyloxirane according to literature$^{(1)}$.

1880 ml of acetonitrile was added into a 3 L three-necked flask, followed by the addition of dimethyl sulfide and dimethyl sulfate, with a mild heat release, and the resulting mixture was stirred at room temperature for 1.5 h and then left it overnight. NaH (60%) was added portionwise into the reaction solution with stirring over 30-40 min, with gas being generated (pay attention to having the flask externally connected to an allihn condenser and a drying tube of anhydrous calcium chloride), and then stirred at room temperature for 1 hour, followed by the dropwise addition of 300 g of cyclopentyl 3-pyridyl ketone over about 10 min, and the resulting mixture was reacted in oil bath at 40-45° C. for 90 min after being stirred at room temperature for 20 min, and then cooled at room temperature and left it overnight. The reaction solution was transferred into an eggplant-shaped flask, the solvent was removed by suction using a water pump (40-42° C., −0.095 MPa), and the remaining solid was then cooled to 0-5° C. in ice bath, followed by the dropwise addition of 2630 ml of ice water (with the inner temperature being controlled at 0-5° C.) over about 1 hour, and the reaction solution was extracted with isopropyl ether (650 ml×3), the ether layer was combined and washed with water until it is neutral (with the pH of water washings being 7.0), and the ether layer was dried over anhydrous sodium sulfate overnight. The drying agent was removed by filtration, the solvent was removed under reduced pressure by suction using a water pump (40-42° C., −0.095 MPa), and 285.5 g of fraction at 121-131° C./3 mmHg was further collected under reduced pressure by using an oil pump.

$^1$HNMR(CDCl$_3$) δ(ppm): 8.68-7.50(m,4H), 2.91-2.66(m, 2H), 2.23-1.29(m,9H).

Step 3: Preparation of 3-[(2-cyclopentyl-2-hydroxyl-2-(3-pyridyl))ethoxyl]-1-azabicyclo[2,2,2] octane free alkali from R-3-quinuclidinol

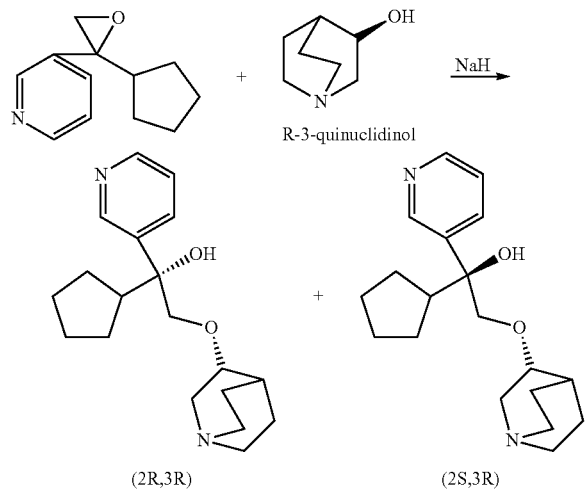

(2R,3R)  (2S,3R)

To 18.72 g (147 mmol) of commercially available R-3-quinuclidinol was added 190 ml DMSO, followed by the addition of 7.59 g (190 mmol) of sodium hydride, and the mixture was reacted at 20-60° C. for 0.5-12 h, and then cooled to room temperature, and a solution of 35.91 g (190 mmol) of 1-(3-pyridyl)-1-cyclopentyloxirane (self-prepared) in 45 ml DMSO was added thereto, and after the completion of dropping, the resulting mixture was heated at 20-70° C. in oil bath to react for 0.5-12 hours. Under the condition of ice bath, 120 ml of ice water was added at an inner temperature of 30° C. or less. The reaction mixture was extracted with isopropyl ether, 100 ml×3; and the ether layer was combined and washed with a saturated NaCl aqueous solution, 100 ml×3. The organic layer was dried over anhydrous sodium sulfate overnight, the drying agent was removed by filtration, and the solvent was removed under reduced pressure to obtain 45.66 g of 3-[(2-cyclopentyl-2-hydroxyl-2-(3-pyridyl))ethoxyl]-1-azabicyclo[2,2,2]octane free alkali as a red oily matter, with the yield of 98.3%. The obtained product was (2R,3R),(2S,3R)-3-[(2-cyclopentyl-2-hydroxyl-2-(3-pyridyl))ethoxyl]-1-azabicyclo[2,2,2]octane free alkali.

Step 4: Purification of 3-[(2-cyclopentyl-2-hydroxyl-2-(3-pyridyl))ethoxyl]-1-azabicyclo[2,2,2] octane free alkali by Column Chromatography and Related Purification Treatment The sample from the above step 3 was separated on silica gel column, using ammoniated dichloromethane or trichloromethane and methanol as mobile phase and a TLC plate to monitor the purity of the sample. Under the above elution system, a sample of a mixture of both (2R,3R) and (2S,3R) configurations of 3-[(2-cyclopentyl-2-hydroxyl-2-(3-pyridyl))ethoxyl]-1-azabicyclo[2,2,2]octane free alkali could be purified into two kinds of free alkali, (2R,3R) and (2S,3R), depending on the elution sequence, thereby obtaining 19.52 g of (2R,3R)-3-[(2-cyclopentyl-2-hydroxyl-2-(3-pyridyl))ethoxyl]-1-azabicyclo[2,2,2]octane free alkali with the yield of 85.5%, and 19.06 g of (2S,3R) configuration of 3-[(2-cyclopentyl-2-hydroxyl-2-(3-pyridyl))ethoxyl]-1-azabicyclo[2,2,2]octane free alkali with the yield of 83.47%.

Step 5: The Same as Step 4 in [Example 1]

Step 6: (2R,3R)-3-[(2-cyclopentyl-2-hydroxyl-2-(3-pyridyl))ethoxyl]-1-(3-phenoxypropyl)-1-azabicyclo [2,2,2]octane bromide

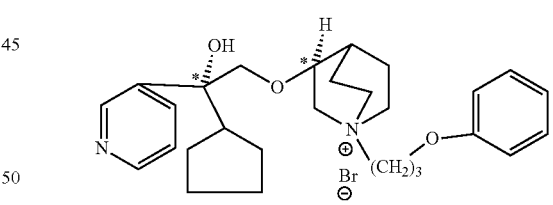

3.18 g (9.1 mmol) of (2R,3R) configuration of the base was added into a 100 ml eggplant-shaped flask and was dissolved by adding 18 ml of chloroform to obtain a yellow transparent solution, to which was added 11.033 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. by rotary evaporation under reduced pressure by a water pump, thereby obtaining a yellow oily matter, to which was added ethyl ether to precipitate a great quantity of solid, and the solid was collected by suction filtration to obtain 3.95 g of (2R,3R)-3-[(2-cyclopentyl-2-hydroxyl-2-(3-pyridyl))ethoxyl]-1-(3-phenoxypropyl)-1-azabicyclo[2,2,2]octane bromide as an off-white solid, with the yield of 81.7%.

The compound prepared in Example 31 was reacted with Ag₂O to remove chlorine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

¹HNMR(D₂O)(ppm): δ8.72-6.63(m,9H), δ4.13-3.61(m, 5H), δ3.44-3.13(m,8H), δ2.14 (m,2H), 2.01(m,1H), δ1.82-1.45(m,13H).

Example 32

(2R,3R)-3-[(2-cyclopentyl-2-hydroxyl-2-(2-furyl))ethoxyl]-1-(3-phenoxypropyl)-1-azabicyclo[2,2,2]octane bromide Step 1: Preparation of cyclopentyl 2-furyl ketone

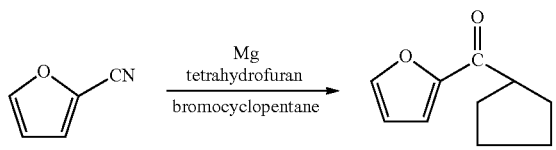 [SMILES: N#Cc1ccco1 ; O=C(c1ccco1)C1CCCC1]

101.5 g of magnesium chips were placed into a 5 L three-necked flask externally connected to an allihn condenser and a drying tube of anhydrous calcium chloride and a thermometer, 1600 ml of THF and 1.05 g of iodine were added thereto and stirred, and 78.28 g of bromocyclopentane was then added dropwise to the reaction solution. At about 5 min after the reaction was fully initiated, the reaction solution was gradually changed from being light reddish brown to be colourless, with the inner temperature automatically increasing to 62-65° C. 548 g of additional bromocyclopentane was then added dropwise over about 35 min, with its refluxing temperature gradually increasing to 75-77° C. The reaction mixture was reacted under refluxing in oil bath for 2 hours.

404 g of 2-furylcarbonitrile diluted in 1600 ml THF was added dropwise into the above reaction solution, and the resulting mixture was then reacted under refluxing in oil bath for 4 hours. The inner temperature was lowered to 5-10° C., 96 ml of ice water was added dropwise, and then stirred for 20 min, followed by the addition of HCl to adjust pH=2.0, and the resulting mixture was heated to reflux for 3 hours, the organic layer was then separated, and once cooled, the aqueous phase was extracted with isopropyl ether (200 ml×3). The organic layer was combined and washed with 1% Na₂CO₃ (500×3) and water (500×3) successively, and the organic layer was dried over anhydrous sodium sulfate overnight. The drying agent was removed by filtration, the solvent was removed by evaporation (42° C., −0.095 MPa), and 272.6 g of oily matter was collected at 108-119° C./6-7 mmHg further by distillation under reduced pressure by using an oil pump.

¹HNMR(CDCl₃) δ(ppm): 7.39-6.70(m,3H), 2.36(m,1H), 1.65-1.45(m,8H).

Step 2: Preparation of 1-(2-furyl)-1-cyclopentyloxirane

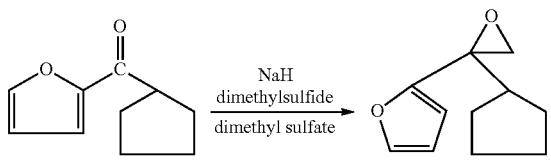 [SMILES: O=C(c1ccco1)C1CCCC1 ; c1coc(C2(C3CCCC3)CO2)c1]

Cyclopentyl 2-furyl ketone as a starting material was reacted to obtain 1-(2-furyl)-1-cyclopentyloxirane according to literature[1].

1780 ml of acetonitrile was added into a 3 L three-necked flask, followed by the addition of dimethyl sulfide and dimethyl sulfate, with a mild heat release, and the resulting mixture was stirred at room temperature for 1.5 h and then left it overnight. NaH (60%) was added portionwise into the reaction solution with stirring over 30-40 min, with gas being generated (pay attention to having the flask externally connected to an allihn condenser and a drying tube of anhydrous calcium chloride), and then stirred at room temperature for 1 hour, followed by the dropwise addition of 250 g of cyclopentyl 3-pyridyl ketone over about 10 min, and the resulting mixture was reacted in oil bath at 40-45° C. for 90 min after being stirred at room temperature for 20 min, and then cooled at room temperature and left it overnight. The reaction solution was transferred into an eggplant-shaped flask, the solvent was removed by suction using a water pump (40-42° C., −0.095 MPa), and the remaining solid was then cooled to 0-5° C. in ice bath, followed by the dropwise addition of 2630 ml of ice water (with the inner temperature being controlled at 0-5° C.) over about 1 hour, and the reaction solution was extracted with isopropyl ether (650 ml×3), the ether layer was combined and washed with water until it is neutral (with the pH of water washings being 7.0), and the ether layer was dried over anhydrous sodium sulfate overnight. The drying agent was removed by filtration, the solvent was removed under reduced pressure by suction using a water pump (40-42° C., −0.095 MPa), and 231.6 g of fraction at 111-121° C./3 mmHg was further collected under reduced pressure by using an oil pump.

¹HNMR(CDCl₃) δ(ppm): 7.35-6.50(m,3H), 2.93-2.65(m, 2H), 2.26-1.27(m,9H).

Step 3: Preparation of 3-[(2-cyclopentyl-2-hydroxyl-2-(2-furyl))ethoxyl]-1-azabicyclo[2,2,2]octane free alkali from R-3-quinuclidinol

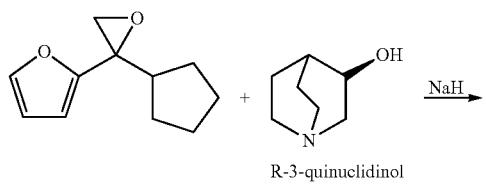

R-3-quinuclidinol

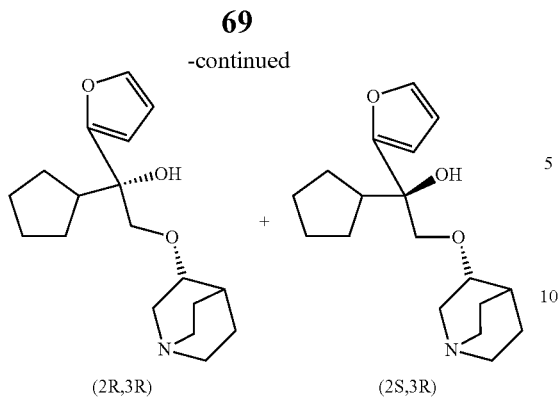

(2R,3R)     (2S,3R)

To 18.72 g (147 mmol) of commercially available R-3-quinuclidinol was added 190 ml DMSO, followed by the addition of 7.59 g (190 mmol) of sodium hydride, and the mixture was reacted at 20-60° C. for 0.5-12 h, and then cooled to room temperature, and a solution of 33.88 g (190 mmol) of 1-(2-furyl)-1-cyclopentyloxirane (self-prepared) in 45 ml DMSO was added thereto, and after the completion of dropping, the resulting mixture was heated at 20-70° C. in oil bath to react for 0.5-12 hours. Under the condition of ice bath, 120 ml of ice water was added at an inner temperature of 30° C. or less. The reaction mixture was extracted with isopropyl ether, 100 ml×3; and the ether layer was combined and washed with a saturated NaCl aqueous solution, 100 ml×3. The organic layer was dried over anhydrous sodium sulfate overnight, the drying agent was removed by filtration, and the solvent was removed under reduced pressure to obtain 42.74 g of 3-[(2-cyclopentyl-2-hydroxyl-2-(2-furyl))ethoxyl]-1-azabicyclo[2,2,2]octane free alkali as a red oily matter, with the yield of 95.32%. The obtained product was (2R,3R),(2S,3R)-3-[(2-cyclopentyl-2-hydroxyl-2-(2-furyl))ethoxyl]-1-azabicyclo[2,2,2]octane free alkali.

Step 4: Purification of 3-[(2-cyclopentyl-2-hydroxyl-2-(2-furyl))ethoxyl]-1-azabicyclo[2,2,2]octane free alkali by Column Chromatography and Related Purification Treatment The sample from the above step 3 was separated on silica gel column, using ammoniated dichloromethane or trichloromethane and methanol as mobile phase and a TLC plate to monitor the purity of the sample. Under the above elution system, a sample of a mixture of both (2R,3R) and (2S,3R) configurations of 3-[(2-cyclopentyl-2-hydroxyl-2-(2-furyl)) ethoxyl]-1-azabicyclo[2,2,2]octane free alkali could be purified into two kinds of free alkali, (2R,3R) and (2S,3R), depending on the elution sequence, thereby obtaining 17.84 g of (2R,3R)-3-[(2-cyclopentyl-2-hydroxyl-2-(2-furyl)) ethoxyl]-1-azabicyclo[2,2,2]octane free alkali with the yield of 83.5%, and 18.03 g of (2S,3R) configuration of 3-[(2-cyclopentyl-2-hydroxyl-2-(2-furyl))ethoxyl]-1-azabicyclo [2,2,2]octane free alkali with the yield of 84.37%.

Step 5: The Same as Step 3 in [Example 1]

Step 6: (2R,3R)-3-[(2-cyclopentyl-2-hydroxyl-2-(2-furyl))ethoxyl]-1-(3-phenoxypropyl)-1-azabicyclo[2,2,2]octane bromide

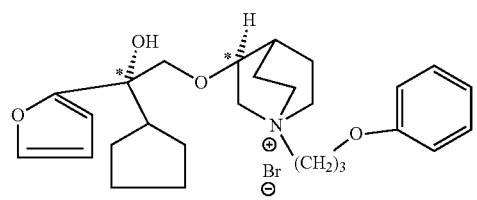

2.78 g (9.1 mmol) of (2R,3R) configuration of the base was added into a 100 ml eggplant-shaped flask and was dissolved by adding 18 ml of chloroform to obtain a yellow transparent solution, to which was added 11.033 g (51.3 mmol) of 3-bromopropoxy benzene and 50 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. by rotary evaporation under reduced pressure by a water pump, thereby obtaining a yellow oily matter, to which was added ethyl ether to precipitate a great quantity of solid, and the solid was collected by suction filtration to obtain 3.97 g of (2R,3R)-3-[(2-cyclopentyl-2-hydroxyl-2-(2-furyl))ethoxyl]-1-(3-phenoxypropyl)-1-azabicyclo[2,2,2] octane bromide as an off-white solid, with the yield of 83.9%.

The compound prepared in Example 32 was reacted with $Ag_2O$ to remove chlorine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR($D_2O$)(ppm): δ7.32-6.19(m,8H), δ4.14-3.60(m, 5H), δ3.42-3.11(m,8H), δ2.11 (m,2H), 1.97(m,1H), δ1.83-1.46(m,13H).

Example 33

(2R,3R)-3-[(2-cyclopentyl-2-hydroxyl-2-(3-pyridyl))ethoxyl]-1-(3-phenoxypropyl)-1-azabicyclo[2,2,2]octane bromide Steps 1, 2, 3, and 4: The Same as Steps 1, 2, 3, and 4 in [Example 31]

Step 5: The Same as Step 4 in [Example 1]

Step 6: The Same as Step 6 in [Example 31]

Step 7: (2R,3R)-3-[(2-cyclopentyl-2-methoxyl-2-(3-pyridyl))ethoxyl]-1-(3-phenoxypropyl)-1-azabicyclo[2,2,2]octane bromide

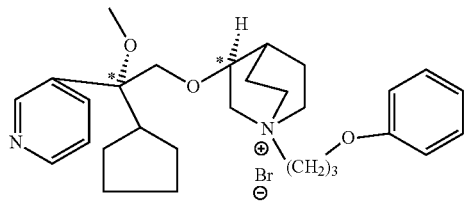

2.655 g (4.87 mmol) of (2R,3R)-3-[(2-cyclopentyl-2-methoxyl-2-(3-pyridyl))ethoxyl]-1-(3-phenoxypropyl)-1-azabicyclo[2,2,2]octane bromide was added into a 100 ml eggplant-shaped flask and was dissolved by adding 30 ml of acetonitrile, and 0.5 g of NaH was then added thereto, followed by the dropwise addition of a solution of bromomethane (0.5 g) in 10 ml of acetonitrile, and the resulting mixture was then stirred at room temperature to react for 20-90 h under the protection of nitrogen, with the completion of reaction being monitored by TLC (TLC condition: chloroform/methanol/ammonia water=5.0 ml/1.5 ml/2 d). After the reaction being completed, the solvent was removed from the reaction solution at 25-40° C. by rotary evaporation under reduced pressure by a water pump, thereby obtaining a yellow oily matter, to which was added ethyl ether to precipitate a great quantity of solid, and the solid was collected by suction filtration to obtain 2.19 g of (2R,3R)-3-[(2-cyclopentyl-2-methoxyl-2-(3-pyridyl))ethoxyl]-1-(3-phenoxypropyl)-1-azabicyclo[2,2,2]octane bromide as an off-white solid, with the yield of 80.37%.

The compound prepared in Example 33 was reacted with $Ag_2O$ to remove chlorine atom so as to obtain hydroxide, which could be reacted with other acids to be converted into corresponding salts. Examples of a salt of a pharmaceutically acceptable acid include a salt derived from an inorganic acid, such as hydrochloride, bromide, iodide, nitrate, carbonate, bicarbonate, phosphate, hydrophosphate, dihydric phosphate, sulfate, disulfate, or phosphite or the like; and a salt derived from a relatively nontoxic organic acid such as acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid or galactonic acid or the like. The examples further include a salt of an amino acid such as arginine or the like.

$^1$HNMR($D_2O$)(ppm): δ8.77-6.66(m,9H), δ4.15-3.65(m, 5H), δ3.44-3.13(m,11H), δ2.16(m,2H), 2.03(m,1H), δ1.85-1.43(m,13H).

Example 1

Intensity of Antagonism of the Example Compounds on the Contractile Response of Tracheal Smooth Muscle from Guinea Pigs Induced by Carbachol (CCh)

1. Method:

Preparation of the Isolated Tracheal Smooth Muscle Specimen from a Guinea Pig:

After a guinea pig was narcotized with urethane, the trachea between the throat and carina of the guinea pig was taken out rapidly, and placed in the Krebs-Henseleit (K-H) solution (composition (g/L): NaCl 6.92, KCl 0.35, $CaCl_2$ 0.28, $KH_2PO_4$ 0.16, $MgSO_4.7H_2O$ 0.4568, $NaHCO_3$ 2.1, Glucose 2.0) with a mixture gas of 5% $CO_2$ and 95% $O_2$ purged. After loose connective tissues and fats around the trachea were separated, the trachea was cut into trachea pieces having a width of about 3 mm and a length of 20 mm by a surgical scissor, with both ends of the trachea piece ligated with 4~0 silk suture, and then placed into a thermostatic bath containing 5 ml of K—H solution (pH 7.4) at 37° C., with the mixture gas of 5% $CO_2$ and 95% $O_2$ continuously purged. A muscle tension transducer was connected to the upper end so as to apply 1.0 g of resting tension to the specimen, the change of the tension was recorded, the culture solution was replaced every 20 min, and the test was started after being balanced for 60 min.

Administration method: After the trachea piece was stabilized, $3 \times 10^{-6}$ mol/L of CCh was added into a bath, and after the contractile tension of the trachea piece reached a peak level, the example compounds, ipratropium bromide and tiotropium bromide were added into a Magnus bath by a cumulative dosing regimen with a dosage of $10^{-9} \sim 10^{-5}$ mol, respectively, and the diastolic condition of the trachea piece was observed: if no response occurred (below the threshold concentration), a next dosage was continued to be added in sequence; if response occurred, after it reached a diastolic plateau, a next dosage was further added. The above operation was repeated until the contractile curve reached the minimum value. Finally, $10^{-6}$ mol/L of isoprenaline was added so that the maximum relaxation would be reached and the curve was recorded.

Statistical approach: The result was expressed as mean ±standard deviation, and counted by Sigma Stat statistical package. The data was analyzed by using variance analysis, the comparison among means of a plurality of specimen was performed by using Student-Newman-Keuls(SNK) test; statistical significant level α=0.05 (bilateral). $EC_{50}$ (95% confidence limit) was calculated by POMS 2.0 version software from Shanghai Scientific and Technical Publishers.

2. Conclusion:

$3 \times 10^{-6}$ mol/L of CCh could cause the tracheal smooth muscle from the guinea pig to generate one durable and stable contractile response. In the cumulative dosing regimen, the example compounds and the control drugs of ipratropium bromide and tiotropium bromide were added into the Magnus bath, and each of the example compounds and each of the control drugs were capable of relaxing the contraction of the tracheal smooth muscle induced by CCh. The results were shown in Table 2.

3. Results

TABLE 2

The antagonism in vitro of the compounds of the present invention against the contraction of the tracheal smooth muscle induced by a concentration of $3 \times 10^{-6}$ mol/L of CCh, $IC_{50}$ (μM)

| Compound | $IC_{50}$ (μM) | Onset time (min) | Time for eliminating inhibition effect (min) |
|---|---|---|---|
| Example 1 | 0.767 | 6.89 | more than 300 |
| Example 2 | 2.855 | 6.53 | more than 300 |
| Example 3 | 0.852 | 6.54 | more than 300 |
| Example 4 | 0.0278 | 6.37 | more than 300 |
| Example 5 | 1.026 | 7.01 | more than 300 |
| Example 6 | 0.156 | 6.61 | more than 300 |
| Example 7 | 0.791 | 6.56 | more than 300 |
| Example 8 | 2.351 | 6.72 | more than 300 |
| Example 9 | 0.758 | 6.13 | more than 300 |
| Example 10 | 0.0227 | 6.24 | more than 300 |
| Example 11 | 1.36 | 6.77 | more than 300 |
| Example 12 | 0.251 | 7.13 | more than 300 |
| Example 13 | 0.917 | 7.25 | more than 300 |
| Example 14 | 4.870 | 6.34 | more than 300 |
| Example 15 | 1.523 | 6.29 | more than 300 |
| Example 16 | 0.0573 | 6.38 | more than 300 |
| Example 17 | 1.566 | 7.05 | more than 300 |
| Example 18 | 0.156 | 6.92 | more than 300 |
| Example 19 | 1.762 | 6.68 | more than 300 |
| Example 20 | 2.354 | 6.32 | more than 300 |
| Example 21 | 1.351 | 6.79 | more than 300 |
| Example 22 | 0.373 | 6.45 | more than 300 |
| Example 23 | 2.022 | 6.78 | more than 300 |
| Example 24 | 0.451 | 6.58 | more than 300 |
| Example 25 | 0.867 | 6.36 | more than 300 |
| Example 26 | 0.0235 | 6.14 | more than 300 |
| Example 27 | 0.0363 | 5.89 | more than 300 |
| Example 28 | 0.0264 | 6.06 | more than 300 |
| Example 29 | 0.723 | 7.14 | more than 300 |
| Example 30 | 0.0371 | 5.98 | more than 300 |
| Example 31 | 0.0206 | 6.37 | more than 300 |
| Example 32 | 0.0379 | 5.85 | more than 300 |
| Example 33 | 0.139 | 6.17 | more than 300 |
| ipratropium bromide | 0.0361 | 6.82 | 185 |
| tiotropium bromide | 0.0142 | 30.37 | more than 300 |

The results in Table 2 showed that each of the example compounds had a significant antagonistic effect on M receptor, wherein (2R,3R) configuration of the compound had the strongest effect, and the intensity of the effect of a plurality of compounds was comparable with that of the positive control agents of ipratropium bromide and tiotropium bromide. The compounds of the present invention and ipratropium bromide had a shorter onset time than tiotropium bromide, and on the contrary, tiotropium bromide acted more slowly. The compounds of the present invention and tiotropium bromide had a longer duration of action.

Example 2

Binding and Selective Effect of the Compounds of the Present Invention on Three Subtypes of M Receptor 1. Method:

The $m_1$, $m_2$, and $m_3$ cells of the transfected Chinese hamster oocyte (CHO) were placed in a DMEM culture medium (which contained 15% fetal calf serum, L-glutamine, 1% non-essential amino acid, 1% antibiotic/antifungal agent), respectively, and then incubated in 5% $CO_2$ incubator at 37° C. When the cells in a culture flask were grown and proliferated to form monolayer cells to overspread about 90% of the bottom of the flask, the culture medium was discarded, and the culture flask was washed with a PBS (pH7.4) buffer solution twice, and then the cells were scraped with an icy phosphate buffer solution (pH7.7, containing 5 mmol/L $MgCl_2$). The collected cells were homogenized with a Teflon glass homogenizer, the homogenized solution was centrifuged at a low temperature, 20000 r×20 min, and the precipitate was homogenized with a reaction buffer solution (pH7.7, containing 5 mmol/L $MgCl_2$) to form a membrane protein suspension. The amount of protein added into each of the reaction tubes was: $m_1$ (about 0.05 mg), $m_2$ (0.05 mg), $m_3$ (0.1 mg), respectively; the concentration of [$^3$H]-QNB was 0.1-2.16 nmol/L; 1 μmol/L of atropine was added into the non-specific binding tube; and the total reaction volume was 300 μL. The resulting solution was then reacted at 25° C. for 30 min and quenched with an icy reaction buffer solution, and further collected onto a glass fiber filter membrane by using a multihead cell collector. After being dried at 80° C., the filter membrane sheet was placed into a liquid scintillation vial, followed by the addition of 5 ml of liquid scintillation agent, and then kept in dark place overnight, with cpm measured by a liquid scintillation spectrometer. Bmax and Kd values were calculated by Graphpad prism software. Ligands labeled by $^3$H-QNB which has no selectivity on M receptor were added into each of the test tubes, in which the concentrations were: $m_1$ and $m_3$ (1.042 nmol/L), $m_2$ (1.81 nmol/L), respectively; different concentrations of non-labeled competitor, Pirenzepine (PZ, selective competitor of $m_1$) or Gallamine (GI, selective competitor of $m_2$) or 4-DAMP (selective competitor of $m_3$) or the compounds of the present invention, were added simultaneously, the final concentration was $10^{-10} \sim 10^{-4}$ mol/L, with 11 dosages in total; the same amount of membrane protein specimen was further added; the total reaction volume was 300 μL, and a competitive binding reaction was then performed. A non-specific binding tube was further provided, and the non-specific binding was measured by a large amount of atropine (the final concentration was 1 μmol/L). The resulting solution was reacted at 25° C. for 30 min and quenched with a reaction buffer solution, and then collected onto a glass fiber filter membrane by using a multihead cell collector. After being dried at 80° C., the filter membrane sheet was placed in a liquid scintillation vial, followed by the addition of 5 ml of liquid scintillation agent, and then kept in dark place overnight, with cpm measured by a liquid scintillation spectrometer. The respective Ki values of the competitors on three subtypes of M receptor were calculated by Graphpad prism software, and converted into pKi values, to compare the selectivity of PZ, GI, 4-DAMP and the compounds to be tested on the subtypes of M receptor.

2. Results

TABLE 3

Comparison of the receptor selectivity of three competitive inhibitors known and the compounds of the present invention on three subtypes of M receptor ($\bar{x} \pm s$, n = 6)

| Name of the inhibitors and the compounds of the invention | Selectivity: Mx/My = Ki(y)/Ki(x) | | |
|---|---|---|---|
| | $m_1/m_2$ | $m_1/m_3$ | $m_2/m_3$ |
| Pirenzepine | 169.82 | 13.49 | 0.079 |
| Gallamine | 0.011 | 0.676 | 60.26 |
| 4-DAMP | 1.66 | 0.095 | 0.058 |
| the compound in Example 1 | 34.13 | 0.358 | 0.0105 |
| the compound in Example 4 | 30.2 | 0.332 | 0.011 |
| the compound in Example 5 | 45.6 | 0.502 | 0.011 |

TABLE 3-continued

Comparison of the receptor selectivity of three competitive inhibitors known and the compounds of the present invention on three subtypes of M receptor ($\bar{x} \pm s$, n = 6)

| Name of the inhibitors and the compounds of the invention | Selectivity: Mx/My = Ki(y)/Ki(x) | | |
|---|---|---|---|
| | $m_1/m_2$ | $m_1/m_3$ | $m_2/m_3$ |
| the compound in Example 14 | 25.6 | 0.205 | 0.008 |
| the compound in Example 16 | 13.5 | 0.67 | 0.037 |

3. Conclusion

The above test with CHO cells transfected by cDNA of three subtypes $m_1$, $m_2$, and $m_3$ of M receptor was used for identifying the selectivity of the compounds of the present invention on subtypes of M receptor. Considering the pharmacological characteristics of Pirenzepine, Gallamine, and 4-DAMP, the results of the competitive inhibition tests of the three compounds with three kinds of cells demonstrated that the three kinds of cells could be used to identify a receptor selectivity of a drug. The results of the above test showed that the tested compounds of the present invention had the highest selectivity on $m_3$ receptor, the second highest selectivity on $m_1$ receptor, and the lowest selectivity on $m_2$ receptor; wherein they had stronger effects on $m_3$ and $m_1$ receptors. They had significant advantages in treating rhinitis, airway hyperresponsiveness, senile chronic trachitis, COPD and gastrointestinal tract ulcerative diseases, as compared with the prior art.

Example 3

Determination of the Intensity and Duration of the Antagonism of the Example Compounds on the Contractile Response of Bronchus in Guinea Pigs Induced by Methacholine (Mch)

1. Method:

Determination of tidal volume, airway flow rate, and transpulmonary pressure: 1.5 g/kg of urethane was intraperitoneally injected to narcotize the guinea pig. The guinea pig was fixed supinely and treated with tracheal intubation, and the external jugular vein was separated and an indwelling needle was inserted; the guinea pig was enclosed into a body plethysmograph, a blunt needle for intubation into thoracic cavity was inserted between ribs 4~5 of the prothorax of the guinea pig, and the intrathoracic pressure could be measured (with a negative value of a water column of a water manometer and a fluctuation with the breath of the guinea pig as marks). After stabilization, the values of the tidal volume, airway flow rate and transpulmonary pressure of the guinea pig prior to administration of Mch were recorded by a MedLab biological signal collection and processing system as base values. 10 μg/kg body weight of Mch was intravenously injected. The changes of the airway flow rate, tidal volume and transpulmonary pressure of the guinea pig within 5 minutes were observed. Calculation of $R_{aw}$ and $C_{dyn}$: the changes of the increased percentage of $R_{aw}$ value and the decreased percentage of $C_{dyn}$ after inhalation of Mch were calculated.

Calculation formulas of $R_{aw}$ and $C_{dyn}$ were respectively:

$$\text{Increased \% of } R_{aw} = \frac{R_{aw} \text{ after inhalation of Mch} - R_{aw} \text{ prior to inhalation (base value)}}{R_{aw} \text{ prior to inhalation (base value)}} \times 100\%$$

$$\text{Decreased \% of } C_{dyn} = \frac{R_{aw} \text{ prior to inhalation of Mch (base value)} - R_{aw} \text{ after inhalation}}{R_{aw} \text{ prior to inhalation of Mch (base value)}} \times 100\%$$

Dose-effect relationship: For each of the example compounds, 27 guinea pigs were randomly divided into 3 groups: a solvent control group with 15 guinea pigs, a group with 1 μg/kg of the example compounds 4, 10, 14, and 26, a group with 3 μg/kg of the example compounds 4, 10, 14, and 26 and a group with 10 μg/kg of the example compounds 4, 10, 14, and 26; after 30 min from the dropping of the above concentration of drugs in the airway, 10 μg/kg body weight of Mch was intravenously injected for excitation, and airway resistance ($R_{aw}$) and pulmonary dynamic compliance ($C_{dyn}$) within 5 min were determined.

Time-effect relationship: After the guinea pigs were narcotized, 10 μg/kg and 5 μg/kg of the example compounds 4, 10, 14, and 26 were dropped in the airway. 10 μg/kg body weight of Mch was intravenously injected for excitation after 0.25 h, 0.5 h, 1 h, 1.5 h, 2 h, 4 h, 6 h, 12 h and 24 h post-dosing, respectively, and airway resistance ($R_{aw}$) and pulmonary dynamic compliance ($C_{dyn}$) within 5 min were determined.

2. Results:

Dose-effect relationship: the dosages of the example compounds 4, 10, 14, and 26 were 1 μg/kg, 3 μg/kg, and 10 μg/kg, respectively, and after 30 min from dropping in the airway, 10 μg/kg body weight of Mch was intravenously injected for excitation, and airway resistance ($R_{aw}$) and pulmonary dynamic compliance ($C_{dyn}$) within 5 min were determined, and the results were shown in the Table below:

TABLE 4

Antagonism of the example compounds 4, 10, 14, and 26 on contractile response of the bronchus in guinea pigs induced by Mch- dose-effect (Mean ± S.E.M) relationship

| Group | Number of animals (n) | Mch 10 μg/kg iv | |
|---|---|---|---|
| | | $R_{aw}$ (cm H$_2$O/ml/s) | $C_{dyn}$ (ml/cm H$_2$O) |
| Solvent control group | 15 | 1.873 ± 0.406 | 0.076 ± 0.008 |
| 1 μg/kg of example compound 4 | 9 | 0.733 ± 0.088 | 0.105 ± 0.012 |
| 3 μg/kg of example compound 4 | 9 | 0.552 ± 0.060* | 0.137 ± 0.015** |
| 10 μg/kg of example compound 4 | 9 | 0.513 ± 0.071* | 0.196 ± 0.017*** |
| 1 μg/kg of example compound 10 | 9 | 0.745 ± 0.089 | 0.098 ± 0.009 |
| 3 μg/kg of example compound 10 | 9 | 0.563 ± 0.057* | 0.135 ± 0.007** |
| 10 μg/kg of example compound 10 | 9 | 0.531 ± 0.092* | 0.189 ± 0.015*** |
| 1 μg/kg of example compound 14 | 9 | 0.719 ± 0.082 | 0.101 ± 0.010 |
| 3 μg/kg of example compound 14 | 9 | 0.560 ± 0.062* | 0.141 ± 0.014** |

TABLE 4-continued

Antagonism of the example compounds 4, 10, 14, and 26 on contractile response of the bronchus in guinea pigs induced by Mch- dose-effect (Mean ± S.E.M) relationship

| Group | Number of animals (n) | Mch 10 μg/kg iv | |
|---|---|---|---|
| | | $R_{aw}$ (cm $H_2O$/ml/s) | $C_{dyn}$(ml/cm $H_2O$) |
| 10 μg/kg of example compound 14 | 9 | 0.504 ± 0.073* | 0.207 ± 0.018*** |
| 1 μg/kg of example compound 26 | 9 | 0.739 ± 0.085 | 0.103 ± 0.014 |
| 3 μg/kg of example compound 26 | 9 | 0.531 ± 0.063* | 0.143 ± 0.016** |
| 10 μg/kg of example compound 26 | 9 | 0.493 ± 0.083* | 0.205 ± 0.018*** |

Statistical approach: one-way ANOVA was used, and the comparison among various groups was tested by Bonferroni method; the comparison with the solvent control group was performed, *P < 0.05, P < 0.01, *P < 0.001.

When 10 μg/kg of Mch was intravenously injected, the airway resistance of guinea pigs increased by 328%, the pulmonary dynamic compliance decreased by 73%. Once 1, 3, and 10 μg/kg of the compounds in example 4, 10, 14, and 26 were dropped in the airway of guinea pigs, the increase of airway resistance and the decrease of pulmonary dynamic compliance were inhibited dose-dependently. The inhibition ratios of the three dosage groups of the example compound 4 against the increase of airway resistance were 64.2% (p<0.01), 86.1% (p<0.001) and 90.8% (p<0.001), respectively; the inhibition ratios against the decrease of pulmonary dynamic compliance were 11.2% (p>0.05), 46.6% (p<0.001) and 50.0% (p<0.001), respectively. The inhibition ratios of the three dosage groups of the example compound 10 against the increase of airway resistance were 63.7% (p<0.01), 84.5% (p<0.001) and 91.3% (p<0.001), respectively; the inhibition ratios against the decrease of pulmonary dynamic compliance were 10.9% (p>0.05), 45.9% (p<0.001) and 49.8% (p<0.001), respectively. The inhibition ratios of the three dosage groups of the example compound 14 against the increase of airway resistance were 63.5% (p≤0.01), 85.4% (p≤0.001) and 90.5% (p<0.001), respectively; the inhibition ratios against the decrease of pulmonary dynamic compliance were 11.0% (p>0.05), 46.1% (p<0.001) and 49.5% (p<0.001), respectively. The inhibition ratios of the three dosage groups of the example compound 26 against the increase of airway resistance were 64.4% (p<0.01), 87.2% (p<0.001) and 92.1% (p<0.001), respectively; the inhibition ratios against the decrease of pulmonary dynamic compliance were 11.0% (p>0.05), 47.1% (p<0.001) and 49.9% (p<0.001), respectively.

Time-effect relationship: When 10 μg/kg of Mch was intravenously injected, the airway resistance of guinea pigs increased by 328%. After 0.25 h from the dropping of 10 μg/kg of [example compounds 4, 10, 14, and 26] in the airway, the inhibition ratio against the increase of airway resistance was 80% or more; and it could reached 90% or more of the maximum inhibition ratio immediately after 1 h. Over time, the inhibition ratio against the increase of airway resistance was still 85% or more after 24 h, and there were statistical differences as compared with the solvent control group (p<0.01~0.001). To confirm the correctness of the results, the dosage of the example compounds 4, 10, 14, and 26 was decreased to 5 μg/kg, the results of which showed that when 5 μg/kg of the example compounds 4, 10, 14, and 26 were dropped in the airway, the inhibition ratio against the airway resistance was 85% or more (p<0.001) after 12 h, and the inhibition ratio against the airway resistance was 65% or more (p<0.01) after 24 h. After 12 h from the dropping of 10 μg/kg and 5 μg/kg of the example compounds 4, 10, 14, and 26 in the airway, there were no significant difference in the inhibition ratio against the airway resistance between the dosages of 10 μg/kg and 5 μg/kg. However, after 24 h, there were significant differences in the inhibition ratio against the airway resistance (p<0.05) between 10 μg/kg and 5 μg/kg of example compounds 4, 10, 14, and 26. The above results indicated that: the action times of 10 μg/kg and 5 μg/kg of [example compounds 4, 10, 14, and 26] administered by dropping in the airway were more than 24 h, and these compounds were super long-lasting M receptor antagonists.

Compounds shown in Table 5 were further prepared according to the present invention, and their $IC_{50}$ (mM) of resistance to the contraction of tracheal smooth muscle from guinea pigs induced by a concentration of $3 \times 10^{-6}$ mol/L of CCh was determined.

TABLE 5

Optical rotation, and $IC_{50}$ (mM) of resistance in vitro to the contraction of tracheal smooth muscle from guinea pigs induced by a concentration of $3 \times 10^{-6}$ mol/L of CCh, of other compounds synthesized according to the present invention

| Example compounds No. | Structures of compounds | Resistance to the contraction of smooth muscle from guinea pigs in vitro, $IC_{50}$ (μM) |
|---|---|---|
| 34 | | 0.654 |

TABLE 5-continued

Optical rotation, and IC₅₀ (mM) of resistance in vitro to the contraction of tracheal smooth muscle from guinea pigs induced by a concentration of 3 × 10⁻⁶ mol/L of CCh, of other compounds synthesized according to the present invention

| Example compounds No. | Structures of compounds | Resistance to the contraction of smooth muscle from guinea pigs in vitro, IC₅₀ (μM) |
|---|---|---|
| 35 | | 0.102 |
| 36 | | 0.068 |
| 37 | | 0.0783 |
| 38 | | 0.0317 |
| 39 | | 0.045 |
| 40 | | 0.805 |
| 41 | | 0.0562 |

TABLE 5-continued

Optical rotation, and IC$_{50}$ (mM) of resistance in vitro to the contraction of tracheal smooth muscle from guinea pigs induced by a concentration of 3 × 10$^{-6}$ mol/L of CCh, of other compounds synthesized according to the present invention

| Example compounds No. | Structures of compounds | Resistance to the contraction of smooth muscle from guinea pigs in vitro, IC$_{50}$ (µM) |
|---|---|---|
| 42 | | 0.078 |
| 43 | | 0.0615 |
| 44 | | 0.147 |
| 45 | | 0.512 |
| 46 | | 1.227 |
| 47 | | 0.506 |

TABLE 5-continued

Optical rotation, and IC$_{50}$ (mM) of resistance in vitro to the contraction of tracheal smooth muscle from guinea pigs induced by a concentration of 3 × 10$^{-6}$ mol/L of CCh, of other compounds synthesized according to the present invention

| Example compounds No. | Structures of compounds | Resistance to the contraction of smooth muscle from guinea pigs in vitro, IC$_{50}$ (µM) |
|---|---|---|
| 48 | | 1.175 |
| 49 | | 0.045 |
| 50 | | 0.413 |
| 51 | | 0.791 |
| 51 | | 0.217 |
| 52 | | 0.513 |
| 53 | | 2.171 |

TABLE 5-continued

Optical rotation, and $IC_{50}$ (mM) of resistance in vitro to the contraction of tracheal smooth muscle from guinea pigs induced by a concentration of $3 \times 10^{-6}$ mol/L of CCh, of other compounds synthesized according to the present invention

| Example compounds No. | Structures of compounds | Resistance to the contraction of smooth muscle from guinea pigs in vitro, $IC_{50}$ (μM) |
|---|---|---|
| 54 | | 0.0376 |
| 55 | | 0.0359 |

Example 5

Compositions and Preparation Thereof

Preparation and Use of Naristillae, Nasal Spray, Aerosol, Powder Aerosol, Atomizing Inhalation and Tablets 1. Naristillae of Single Drug Prescription

| | |
|---|---|
| Example compound 16 | 3 mg |
| Benzalkonium chloride | 3 mg |
| $H_2O$ | 10 ml |

In the 100,000-grade production condition, the active ingredient of the example compound 10 and a bacteriostat (benzalkonium chloride) were dissolved in $H_2O$, and then filled into a brown vial equipped with a fusiform cap which could be used for nasal dropping.

For this naristillae of single drug prescription, 2.0-20 mg could be dissolved in each 10 ml of water, to be formulated into different concentrations of naristillae; and the amount of bacteriostat of benzalkonium chloride could range from 1-5 mg.

The dosage of the naristillae of single drug prescription was 2-3 droplets (0.1 ml-0.15 ml)/nostril, about 20-300 g/nostril every time.

2. Compound Naristillae

| | |
|---|---|
| Example compound 10 | 2.5 mg |
| Fenoterol | 10 mg |
| Benzalkonium chloride | 5 mg |
| $H_2O$ | 10 ml |

In the 100,000-grade production condition, active ingredients (example compound 10 and fenoterol) and a bacteriostat (benzalkonium chloride) were dissolved in $H_2O$, and then filled into a brown vial equipped with a fusiform cap which could be used for nasal dropping. The amount of bacteriostat of benzalkonium chloride could range from 1-5 mg. The dosage of the compound naristillae was 2-3 droplets (0.1 ml-0.15 ml)/nostril, about 25 μg/nostril every time.

3. Metering Pump Nasal Spray

| | |
|---|---|
| Example compound 4 | 3.33 mg |
| Benzalkonium chloride | 5.00 mg |
| 1N HCl | added to pH 4-6 |
| Pure $H_2O$ | 2.0 ml |

In the 100,000-grade production condition, the above components were dissolved in pure $H_2O$, and then filled into a bottle equipped with a metering pump suitable for nasal spray, and the volume sprayed from this pump every time was 70-90 μl. The dosage was 1-2 sprays/nostril, about 21-60 μg/nostril every time.

To obtain a larger dosage in treating serious patients, the amount of compound 4 could be increased.

4. Metered-dose Aerosol Containing a Propellant

| Component | weight |
|---|---|
| Example compound 4 | 10 mg |
| Ethanol | 2.4 g |
| Oleic acid | 7.0 mg |
| HFA-134a | 11.75 g |

After the example compound 4 was dissolved with ethanol and oleic acid, HFA-134a was filled by a one-step method. Then, in the 100,000-grade production condition, the resulting mixture was mixed with a surfactant and propellants of 1-fluro-3-chloromethane, 2-fluro-2-chloromethane and 4-fluro-2-chloroethane in proportion, and then encapsulated into a quantitative pressure vessel by a press-filling machine. 10 g was contained in each bottle, 100 mg was contained in each spray, and 20 μg of the example compound 4 was contained.

5. Capsule-type Powder Aerosol

An capsule-type powder aerosol was composed of the following ingredients:

| Example compound 4 | 0.05 g |
|---|---|
| Lactose | 98.95 g |
| Sodium benzoate | 1.0 g |

In the 100,000-grade production condition, the example compound 4 together with lactose and sodium benzoate were processed by micronization, with a particle diameter of 5 μm or less, and then mixed thoroughly and homogeneously, and finally encapsulated into a capsule. 40 mg was contained in each capsule, and 20 μg of the compound of the present invention was contained in each inhalation. In this pharmaceutical composition for treating a disease of respiratory system, lactose was a diluent which could further be selected from arabinose, glucan, mannitol, mannitol, xylitol, saccharose, fructose, sorbitol, maltose, amino acid or glucose or the like; sodium benzoate was a lubricant, and magnesium stearate could also be used as a lubricant.

6. Tablet

| Example compound 6 | 5 g |
|---|---|
| Lactose | 71.5 g |
| Microcrystalline cellulose | 22 g |
| Magnesium stearate | 1.5 g |

Example compound 6 was mixed homogeneously with lactose and microcrystalline cellulose, and further mixed homogeneously after magnesium stearate was added, and the resulting mixture was dry-pressed into tablets, with a tablet weight of 100 mg.

7. Inhalation Solution

| Example compound 10 | 100 mg |
|---|---|
| Normal saline | 1000 ml |

Example compound 10 was dissolved in 800 ml normal saline, and then transferred into a 1000 ml volumetric flask, and normal saline was supplemented to the scale mark, and then the resulting solution was divided and charged into ampoules, 1 ml/ampoule, and heated at 115° C. for 30 min.

What we claim is:

1. A compound of formula I:

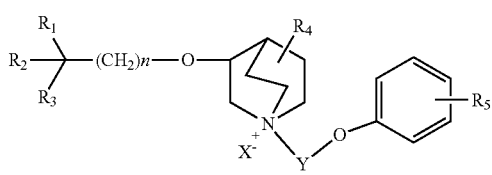

(I)

or a pharmaceutically acceptable salt, solvate or optical isomer thereof,
wherein in formula I:
n is from 1-7,
$R_1$ is a $C_3$-$C_7$ hydrocarbyl which can be unsubstituted or optionally substituted by halogen, alkoxy, alkoxyhydrocarbyl, heterocyclyl or aryl, $R_2$ is an aryl or a heteroaryl containing one or more heteroatoms which can be unsubstituted, or optionally substituted, $R_3$ is a hydroxyl, halogen, alkoxy or acyloxy, wherein the alkoxy or acyloxy can be unsubstituted or optionally substituted by halogen, hydroxyl, alkoxy, hydrocarbyl, alkoxyhydrocarbyl, heterocyclyl, or aryl;

$R_4$ and $R_5$ can be present or absent, and are independently selected from the group consisting of halogen, hydroxyl, alkoxy, hydrocarbyl, alkoxyhydrocarbyl, heterocyclyl or aryl, when present;

Y is a linear or branched $C_1$-$C_7$ alkyl or —($CH_2$—O—$CH_2$)$_m$—, which can be optionally substituted, wherein m is equal to 1-3, $X^-$ is an acid radical or hydroxyl.

2. The compound according to claim 1, wherein:
n is 1-3, $R_1$ is an unsubstituted cycloalkyl,
$R_2$ is a phenyl, naphthyl, or biphenyl, which can be unsubstituted or optionally substituted by one or more of halogen, hydroxyl, phenyl, —$OR_6$, —$SR_6$, —$NR_6R_7$, —$NHCOR_6$, —$CONR_6R_7$, —CN, —$NO_2$, —$COOR_6$, —$CF_3$ or linear or branched $C_1$-$C_4$ hydrocarbyl, $R_6$ and $R_7$ can be a hydrogen atom, a linear or branched $C_1$-$C_4$ hydrocarbyl, or can form a cyclohydrocarbyl together,
$R_3$ is a hydroxyl or methoxyl,
Y is a methyl, ethyl, propyl or —($CH_2$—O—$CH_2$)$_2$—.

3. The compound according to claim 1, wherein,
n is 1,
$R_1$ is a cyclopentyl or cyclohexyl,
$R_2$ is an unsubstituted phenyl, pyridyl, furyl or thienyl,
Y is an ethyl or propyl.

4. The compound according to claim 1, wherein $X^-$ is hydroxide or an acid radical of a pharmaceutically acceptable inorganic acid being selected from the group consisting of hydrochloric acid, bromic acid, iodic acid, nitric acid, carbonic acid, phosphoric acid, sulfuric acid or phosphorous acid, so that the compound of formula I is in the form of a quaternary ammonium base or a pharmaceutically acceptable salt being selected from the group consisting of hydrochloride, bromide, iodide, nitrate, carbonate, bicarbonate, phosphate, hydrophosphate, dihydric phosphate, sulfate, disulfate or phosphite.

5. The compound according to claim 1, wherein X– is an acid radical of a pharmaceutically acceptable organic acid, so that the compound of formula I is in the form of a salt of an organic acid, wherein said organic acid is acetic acid, propionic acid, isobutyric acid, malonic acid, benzoic acid, succinic acid, suberic acid, fumaric acid, mandelic acid, phthalic acid, benzenesulfonic acid, p-toluenesulfonic acid, citric acid, tartaric acid, methanesulfonic acid, glucuronic acid, galactonic acid or amino acid.

6. The compound according to claim 1, which is:
(2S,3R)-3-[(2-cyclopentyl-2-hydroxyl-2-phenyl)ethoxyl]-1-(3-phenoxypropyl)-1-azabicyclo[2,2,2]octane bromide;
(2S,3S)-3-[(2-cyclopentyl-2-hydroxyl-2-phenyl)ethoxyl]-1-(3-phenoxypropyl)-1-azabicyclo[2,2,2]octane bromide;
(2R,3R)-3-[(2-cyclopentyl-2-hydroxyl-2-phenyl)ethoxyl]-1-(3-phenoxypropyl)-1-azabicyclo[2,2,2]octane bromide;
(2R,3S)-3-[(2-cyclopentyl-2-hydroxyl-2-phenyl)ethoxyl]-1-(3-phenoxypropyl)-1-azabicyclo[2,2,2]octane bromide;

(2S,3R),(2R,3S)-3-[(2-cyclopentyl-2-hydroxyl-2-phenyl)ethoxyl]-1-(3-phenoxypropyl)-1-azabicyclo[2,2,2]octane bromide;

(2R,3R),(2S,3S)-3-[(2-cyclopentyl-2-hydroxyl-2-phenyl)ethoxyl]-1-(3-phenoxypropyl)-1-azabicyclo[2,2,2]octane bromide;

(2S,3R)-3-[(2-cyclohexyl-2-hydroxyl-2-phenyl)ethoxyl]-1-(3-phenoxypropyl)-1-azabicyclo[2,2,2]octane bromide;

(2S,3S)-3-[(2-cyclohexyl-2-hydroxyl-2-phenyl)ethoxyl]-1-(3-phenoxypropyl)-1-azabicyclo[2,2,2]octane bromide;

(2R,3R)-3-[(2-cyclohexyl-2-hydroxyl-2-phenyl)ethoxyl]-1-(3-phenoxypropyl)-1-azabicyclo[2,2,2]octane bromide;

(2R,3S)-3-[(2-cyclohexyl-2-hydroxyl-2-phenyl)ethoxyl]-1-(3-phenoxypropyl)-1-azabicyclo[2,2,2]octane bromide;

(2R,3S),(2S,3R)-3-[(2-cyclohexyl-2-hydroxyl-2-phenyl)ethoxyl]-1-(3-phenoxypropyl)-1-azabicyclo[2,2,2]octane bromide;

(2R,3R),(2S,3S)-3-[(2-cyclohexyl-2-hydroxyl-2-phenyl)ethoxyl]-1-(3-phenoxypropyl)-1-azabicyclo[2,2,2]octane bromide;

(2S,3R)-3-[(2-cyclobutyl-2-hydroxyl-2-phenyl)ethoxyl]-1-(3-phenoxypropyl)-1-azabicyclo[2,2,2]octane bromide;

(2S,3S)-3-[(2-cyclobutyl-2-hydroxyl-2-phenyl)ethoxyl]-1-(3-phenoxypropyl)-1-azabicyclo[2,2,2]octane bromide;

(2R,3S)-3-[(2-cyclobutyl-2-hydroxyl-2-phenyl)ethoxyl]-1-(3-phenoxypropyl)-1-azabicyclo[2,2,2]octane bromide;

(2R,3R)-3-[(2-cyclobutyl-2-hydroxyl-2-phenyl)ethoxyl]-1-(3-phenoxypropyl)-1-azabicyclo[2,2,2]octane bromide;

(2R,3S),(2S,3R)-3-[(2-cyclobutyl-2-hydroxyl-2-phenyl)ethoxyl]-1-(3-phenoxypropyl)-1-azabicyclo[2,2,2]octane bromide;

(2R,3R),(2S,3S)-3-[(2-cyclobutyl-2-hydroxyl-2-phenyl)ethoxyl]-1-(3-phenoxypropyl)-1-azabicyclo[2,2,2]octane bromide;

(2S,3R)-3-[(2-cyclopropyl-2-hydroxyl-2-phenyl)ethoxyl]-1-(3-phenoxypropyl)-1-azabicyclo[2,2,2]octane bromide;

(2R,3S)-3-[(2-cyclopropyl-2-hydroxyl-2-phenyl)ethoxyl]-1-(3-phenoxypropyl)-1-azabicyclo[2,2,2]octane bromide;

(2S,3S)-3-[(2-cyclopropyl-2-hydroxyl-2-phenyl)ethoxyl]-1-(3-phenoxypropyl)-1-azabicyclo[2,2,2]octane bromide;

(2R,3R)-3-[(2-cyclopropyl-2-hydroxyl-2-phenyl)ethoxyl]-1-(3-phenoxypropyl)-1-azabicyclo[2,2,2]octane bromide;

(2R,3S),(2S,3R)-3-[(2-cyclopropyl-2-hydroxyl-2-phenyl)ethoxyl]-1-(3-phenoxypropyl)-1-azabicyclo[2,2,2]octane bromide;

(2R,3R),(2S,3S)-3-[(2-cyclopropyl-2-hydroxyl-2-phenyl)ethoxyl]-1-(3-phenoxypropyl)-1-azabicyclo[2,2,2]octane bromide;

(2S,3R)-3-[(2-cyclopentyl-2-hydroxyl-2-phenyl)ethoxyl]-1-(2-phenoxyethyl)-1-azabicyclo[2,2,2]octane bromide;

(2R,3R)-3-[(2-cyclopentyl-2-hydroxyl-2-phenyl)ethoxyl]-1-(2-phenoxyethyl)-1-azabicyclo[2,2,2]octane bromide;

(2R,3R)-3-[(2-cyclopentyl-2-hydroxyl-2-phenyl)ethoxyl]-1-phenoxymethyl-1-azabicyclo[2,2,2]octane bromide;

(2R,3R)-3-[(2-cyclopentyl-2-hydroxyl-2-phenyl)ethoxyl]-1-phenoxymethoxymethyl-1-azabicyclo[2,2,2]octane chloride;

(2R 3R)-3-[(2-cyclopentyl-2-hydroxyl-2-naphthyl)ethoxyl]-1-(3-phenoxypropyl)-1-azabicyclo[2,2,2]octane bromide;

(2R,3R)-3-[(2-cyclopentyl-2-hydroxyl-2-(o-chlorophenyl))ethoxyl]-1-(3-phenoxypropyl)-1-azabicyclo[2,2,2]octane bromide;

(2R,3R)-3-[(2-cyclopentyl-2-hydroxyl-2-(3-pyridyl))ethoxyl]-1-(3-phenoxypropyl)-1-azabicyclo[2,2,2]octane bromide;

(2R,3R)-3-[(2-cyclopentyl-2-hydroxyl-2-(2-furyl))ethoxyl]-1-(3-phenoxypropyl)-1-azabicyclo[2,2,2]octane bromide; or (2R,3R)-3-[(2-cyclopentyl-2-methoxyl-2-(3-pyridyl))ethoxyl]-1-(3-phenoxypropyl)-1-azabicyclo[2,2,2]octane bromide.

7. A pharmaceutical composition comprising the compound according to claim 1 and a pharmaceutically acceptable carrier, wherein the composition can be any suitable dosage form; and the composition can further comprise or not comprise one or more of other drugs available for combined administration.

8. A method for the manufacture of the compound according to claim 1 comprising the steps of:

(1) reacting $R_2$—CN with $R_1$—Br to form

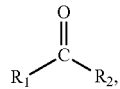

and reacting

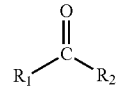

with NaH, dimethyl sulfide and dimethyl sulfate to form an intermediate 1 being formula

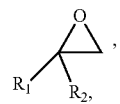

(2) reacting the intermediate 1 with

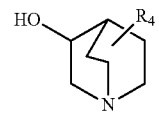

in the presence of NaH to form an intermediate 2 being formula

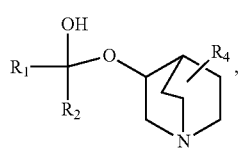

(3) reacting

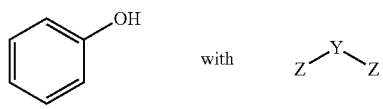

in the presence of NaOH to form an intermediate 4 being formula

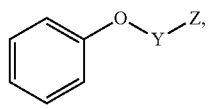

wherein Z is halogen atom, (4) reacting the intermediate 2 with the intermediate 4, to obtain the compound of formula (I).

9. The method according to claim 8, further comprising the step of purifying and separating the chemical isomers of intermediate 2 after the completion of step (2).

10. The method according to claim 8, wherein after the completion of step (4), the compound is reacted with $Ag_2O$ to replace halogen with hydroxide, which can be then converted into other acid radical by reacting with other acid.

11. A pharmaceutical composition comprising the compound of claim 1 for treating diseases associated with M receptors.

12. The pharmaceutical composition of claim 11, wherein the diseases associated with M receptors are selected from the group consisting of rhinitis, post-cold rhinitis, chronic trachitis, airway hyperresponsiveness, asthma, chronic obstructive pulmonary diseases, cough, urinary incontinence, frequent urination, unstable bladder syndrome, bladder spasms, bladder inflammation, gastrointestinal diseases, irritable bowel syndrome, spastic colitis, duodenal ulcers, and gastric ulcers.

13. The compound according to claim 2, wherein,
n is 1,
$R_1$ is a cyclopentyl or cyclohexyl,
$R_2$ is an unsubstituted phenyl, pyridyl, furyl or thienyl,
Y is an ethyl or propyl.

14. A pharmaceutical composition comprising the compound according to claim 2 and a pharmaceutically acceptable carrier, wherein the composition can be any suitable dosage form; and the composition can further comprise or not comprise one or more of other drugs available for combined administration.

15. A pharmaceutical composition comprising the compound according to claim 3 and a pharmaceutically acceptable carrier, wherein the composition can be any suitable dosage form; and the composition can further comprise or not comprise one or more of other drugs available for combined administration.

16. A pharmaceutical composition comprising the compound according to claim 4 and a pharmaceutically acceptable carrier, wherein the composition can be any suitable dosage form; and the composition can further comprise or not comprise one or more of other drugs available for combined administration.

17. The method according to claim 9, wherein after the completion of step (4), the compound is reacted with $Ag_2O$ to replace halogen with hydroxide, which can be then converted into other acid radical by reacting with other acid.

18. A pharmaceutical composition comprising the compound of claim 2 for treating diseases associated with M receptors.

19. A pharmaceutical composition comprising the compound of claim 3 for treating diseases associated with M receptors.

20. A pharmaceutical composition comprising the compound of claim 4 for treating diseases associated with M receptors.

21. A pharmaceutical composition comprising the compound according to claim 1 and a pharmaceutically acceptable carrier, wherein the composition can be the dosage form for inhalation administration or nasal administration; and the composition can further comprise or not comprise one or more of other drugs available for combined administration.

22. A pharmaceutical composition comprising the compound according to claim 2 and a pharmaceutically acceptable carrier, wherein the composition can be the dosage form for inhalation administration or nasal administration; and the composition can further comprise or not comprise one or more of other drugs available for combined administration.

23. A pharmaceutical composition comprising the compound according to claim 3 and a pharmaceutically acceptable carrier, wherein the composition can be the dosage form for inhalation administration or nasal administration; and the composition can further comprise or not comprise one or more of other drugs available for combined administration.

24. A pharmaceutical composition comprising the compound according to claim 4 and a pharmaceutically acceptable carrier, wherein the composition can be the dosage form for inhalation administration or nasal administration; and the composition can further comprise or not comprise one or more of other drugs available for combined administration.

\* \* \* \* \*